United States Patent
Shendure et al.

(10) Patent No.: US 11,694,764 B2
(45) Date of Patent: Jul. 4, 2023

(54) METHOD FOR LARGE SCALE SCAFFOLDING OF GENOME ASSEMBLIES

(71) Applicant: UNIVERSITY OF WASHINGTON, Seattle, WA (US)

(72) Inventors: Jay Shendure, Seattle, WA (US); Andrew Adey, Seattle, WA (US); Joshua Burton, Seattle, WA (US); Jacob Kitzman, Seattle, WA (US); Maitreya J. Dunham, Seattle, WA (US); Ivan Liachko, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 539 days.

(21) Appl. No.: 15/024,990

(22) PCT Filed: Sep. 27, 2014

(86) PCT No.: PCT/US2014/057930
§ 371 (c)(1),
(2) Date: Mar. 25, 2016

(87) PCT Pub. No.: WO2015/048595
PCT Pub. Date: Apr. 2, 2015

(65) Prior Publication Data
US 2016/0239602 A1    Aug. 18, 2016

Related U.S. Application Data

(60) Provisional application No. 61/883,446, filed on Sep. 27, 2013.

(51) Int. Cl.
| | | |
|---|---|---|
| G16B 5/00 | (2019.01) | |
| G16B 30/00 | (2019.01) | |
| G16B 20/00 | (2019.01) | |
| G16B 20/20 | (2019.01) | |
| G16B 30/20 | (2019.01) | |
| G16B 30/10 | (2019.01) | |
| G16B 40/00 | (2019.01) | |

(52) U.S. Cl.
CPC ............ *G16B 5/00* (2019.02); *G16B 20/00* (2019.02); *G16B 20/20* (2019.02); *G16B 30/00* (2019.02); *G16B 30/10* (2019.02); *G16B 30/20* (2019.02); *G16B 40/00* (2019.02)

(58) Field of Classification Search
None
See application file for complete search history.

(56) References Cited

U.S. PATENT DOCUMENTS

| | | | |
|---|---|---|---|
| 6,714,874 B1 | 3/2004 | Myers | |
| 8,642,295 B2 | 2/2014 | De Laat et al. | |
| 2003/0224384 A1 | 12/2003 | Sayood et al. | |
| 2011/0195406 A1 | 8/2011 | Sorenson et al. | |
| 2011/0257889 A1 | 10/2011 | Klammer et al. | |
| 2012/0330559 A1 | 12/2012 | Jiang et al. | |
| 2013/0096009 A1 | 4/2013 | Dekker et al. | |
| 2013/0183672 A1 | 7/2013 | De Laat et al. | |
| 2014/0136121 A1 | 5/2014 | Xu et al. | |

FOREIGN PATENT DOCUMENTS

| | | |
|---|---|---|
| WO | 2013004005 A1 | 1/2013 |
| WO | 2014019164 A1 | 2/2014 |

OTHER PUBLICATIONS

Dostie et al. (Genome Res. Oct. 2006; 16(10): 1299-1309) (Year: 2006).*
Gondon et al. (Nat. Protoc. 2008;3(2):303-13) (Year: 2008).*
Korbel et al. (Nature Biotechnology, 2013, vol. 31, pp. 1099-1101) (Year: 2013).*
Adey, et al., "The haplotype-resolved genome and epigenome of the aneuploid HeLa cancer cell line," Nature, vol. 500, pp. 207-212, Aug. 8, 2013.
Albertsen, et al., "Genome sequences of rare, uncultured bacteria obtained by differential coverage binning of multiple metagenomes," Nature Biotechnol. vol. 31, No. 6, pp. 533-541, Jun. 2013.
Altschul, et al., "Basic Local Alignment Search Tool," J. Mol. Biol. No. 215, pp. 403-410, 1990.
Baird, et al., "Rapid SNP Discovery and Genetic Mapping Using Sequenced RAD Markers," PLoS One, vol. 3, Issue 10, pp. 1-7, Oct. 2008.
Baker, et al., "Extensive DNA-binding specificity divergence of a conserved transcription Yegulator," PNAS, vol. 108, No. 18, pp. 7493-7498, May 3, 2011.
Beitel, et al., "Strain- and plasmid-level deconvolution of a synthetic metagenome by sequencing proximity ligation products," PeerJ, pp. 1-19, May 27, 2014.
Belloch, et al., "Inter- and Intraspecific Chromosome Pattern Variation in the Yeast Genus *Kluyveromyces*," Yeast, vol. 14, pp. 1341-1354, 1998.

(Continued)

*Primary Examiner* — Pablo S Whaley
(74) *Attorney, Agent, or Firm* — Perkins Coie LLP

(57) ABSTRACT

Computational methods used for large scale scaffolding of a genome assembly are provided. Such methods may include a step of applying a location clustering model to a test set of contigs to form two or more location cluster groups, each location cluster group comprising one or more location-clustered contigs; a step of applying an ordering model to each of the two or more location cluster groups to form an ordered set of one or more location-clustered contigs within each cluster group; and a step of applying an orienting model to each ordered set of one or more location-clustered contigs to assign a relative orientation to each of the location-clustered contigs within each location cluster group. In some aspects, the test set of contigs are generated from aligning a set of reads generated by a chromosome conformation analysis technique (e.g., Hi-C) with a draft assembly, a reference assembly, or both.

4 Claims, 66 Drawing Sheets

(56) References Cited

OTHER PUBLICATIONS

Burton, et al., "Chromosome-scale scaffolding of de novo genome assemblies based on chromatin interactions," Nature Biotechol., vol. 31, No. 12, pp. 1119-1127, Dec. 2013.

Carr, et al., "Reconstructing the Genomic Content of Microbiome Taxa through Shotgun Metagenomic Deconvolution," PLoS Computational Biol., vol. 9, Issue 10, pp. 1-15, Oct. 2013.

Compeau, et al., "How to apply de Bruijn graphs to genome assembly," Nature Biotechnol., vol. 29, No. 11, 987-991, Nov. 2011.

David, et al., Diet rapidly and reproducibly alters the human gut microbiome, Nature, vol. 505, 559-576, Jan. 23, 2014.

Dekker, et al., "Exploring the three-dimensional organization of genomes: interpreting chromatin interaction data," Nat. Rev. Genet., vol. 14, No. 6, pp. 390-403, Jun. 2013.

Dick, et al., "Community-wide analysis of microbial genome sequence signatures," Genome Biology, vol. 10, Issue 8, pp. R.85.1-R.85.16, Aug. 10, 2009.

Dixon, et al., "Topological domains in mammalian genomes identified by analysis of chromatin interactions," Nature, vol. 485, pp. 376-380, May 17, 2012.

Dong, et al., "Sequencing and automated whole-genome optical mapping of the genome of a domestic goat (*Capra hircus*)," Nature Biotechnol., vol. 31, No. 2, pp. 135-143, Feb. 2013.

Duan, et al., "A three-dimensional model of the yeast genome," Nature, vol. 465, pp. 363-367, May 20, 2010.

Eisen, et al., "Cluster analysis and display of genome-wide expression patterns," Proc. Natl. Acad. Sci. USA, Genetics, vol. 95, pp. 14863-14868, Dec. 1998.

European Patent Office, Extended European Search Report, EP App. 14846949.7, 13 pp., dated May 17, 2017.

Fraley, et al., "How Many clusters? Which Clustering Method? Answers via Model-Based Cluster Analysis," The Computer Journal, vol. 41, No. 8, pp. 578-588, 1988.

Frias-Lopez, et al., "Microbial community gene expression in ocean surface waters," PNAS, vol. 105, No. 10, pp. 3805-3810, Mar. 11, 2008.

Genome 10K Community of Scientists, "Genome 10K: a Proposal to Obtain Whole-Genome Sequence for 10 000 Vertebrate Species," Journal of Heredity, vol. 100, No. 6, pp. 659-674, Nov. 5, 2009.

Gnerre, et al., "High-quality draft assemblies of mammalian genomes from massively parallel sequence data," PNAS, vol. 108, No. 4, pp. 1513-1518, Jan. 25, 2011.

Gordon, et al., "Mechanisms of Chromosome Number Evolution in Yeast," PLoS Genetics, vol. 7, Issue 7, pp. 1-13, Jul. 21, 2011.

Howe, et al., "Tackling soil diversity with the assembly of large, complex metagenomes," PNAS, vol. 111, No. 13, pp. 4904-4909, Apr. 1, 2014.

Hug, et al., "Community genomic analyses constrain the distribution of metabolic traits across the Chloroflexi phylum and indicate roles in sediment carbon cycling," Microbiome, vol. 1, No. 22, pp. 1-17, Aug. 5, 2013.

Human Microbiome Project Consortium, the, "Structure, function and diversity of the healthy human microbiome," Nature, vol. 486, pp. 207-214, Jun. 14, 2012.

International Human Genome Sequencing Consortium, "Initial sequencing and analysis of the human genome," Nature, vol. 409, pp. 860-921, Feb. 15, 2001.

International Human Genome Sequencing Consortium, "Finishing the euchromatic sequence of the human genome," Nature, vol. 431, pp. 931-945, Oct. 21, 2004.

Iverson, et al., "Untangling Genomes from Metagenomes: Revealing an Uncultured Class of Marine Euryarchaeota," Science, vol. 335, pp. 587-590, Feb. 3, 2012.

Jarvis, et al., "Clustering Using a Similarity Measure Based on Shared Near Neighbors," IEEE Trans on Computers, vol. C-22, No. 11, pp. 1025-1034, Nov. 1973.

Jeffrries, et al., "Genome sequence of the lignocellulose-bioconverting and xylose-fermenting yeast *Pichia stipites*", Nature Biotechn., vol. 25, No. 3, pp. 319-326, Mar. 2007.

Jung, et al., "A Decision Criterion for the Optimal Number of Clusters in Hierarchical Clustering," Journal of Global Optimization, vol. 25, pp. 91-111, 2003.

Kaplan, et al., High-throughput genome scaffolding from in vivo DNA interaction frequency, Nature Biotechnol., vol. 31, No. 12, pp. 1143-1149, Dec. 2013.

Kim, et al., "A Scaffold Analysis Tool Using Mate-pair Information in Genome Sequencing," J Biomed Biotechnol, pp. 1-8, 2008.

Kitzman, et al., "Haplotype-resolved genome sequencing of a Gujarati Indian individual," Nat Biotechnol, vol. 29, No. 1, pp. 59-63, Jul. 1, 2011.

Lam, et al., "Genome mapping on nanochannel arrays for structural variation analysis and sequence assembly," Nat Biotechnol, vol. 30, No. 8, pp. 771-777, Aug. 2012.

Landry, et al., The Genomic and Transcriptomic Landscape of a HeLa Cell Line, G3 Genes Genomes Genetics, vol. 3, pp. 1213-1224, Aug. 2013.

Le, et al., "High-Resolution Mapping of the Spatial Organization of a Bacterial Chromosome," Science, vol. 342, pp. 731-734, Nov. 8, 2013.

Li, et al., "Fast and accurate long-read alignment with Burrows-Wheeler transform," Bioinformatics, vol. 26, No. 5, pp. 589-595, Jan. 15, 2010.

Li, et al., "De novo assembly of human genomes with massively parallel short read sequencing," Cold Spring Harbor Laboratory Press, pp. 1-9, May 19, 2016.

Li, et al., Fast and accurate short read alignment with Burrows-Wheeler transformation, Bioinformatics, vol. 25, No. 14, pp. 1754-1760, 2009.

Lieberman-Aiden, et al., "Comprehensive Mapping of Long-Range Interactions Reveals Folding Principles of the Human Genome," Science, American Association for the Advancement of Science, vol. 326, No. 5950, pp. 289-293, Oct. 9, 2009.

MacKay, et al., "The *Drosphila melanogaster* Genetic Reference Panel," Nature, vol. 482, pp. 173-178, Feb. 9, 2012.

MacVille, et al., "Comprehensive and Definitive Molecular Cytogenic Characterization of HeLa Cells by Spectral Karyotyping," Cancer Research, No. 59, pp. 141-150, Jan. 1, 1999.

Mitra, et al., "Analysis of the intestinal microbiota using SOLiD 16S rRNA gene sequencing and SOLiD shotgun sequencing," BMC Genomics, vol. 14 (supp'l 5), pp. 1-11, 2013.

Moissiard, et al., "MORC Family ATPases Required for Heterochromatin Condensation and Gene Silencing#," Science, pp. 1449-1451, Jun. 15, 2012.

Mouse Genome Sequencing Consortium, "Initial sequencing and comparative analysis of the mouse genome," Nature, vol. 420, pp. 520-562, Dec. 5, 2002.

Moustafa, et al., Transcriptome Profiling of a Toxic Dinaflagellate Reveals a Gene-Rich Protist and a Potential Impact on Gene Expression Due to Bacterial Presence, PLoS ONE, vol. 5, Issue 3, pp. 1-10, Mar. 2010.

Namiki, et al., "MetaVelvet: an extension of Velvet assembler to de novo metagenome assembly from short sequence reads," Nucleic Acids Research, vol. 40, No. 20, pp. 1-12, Jul. 19, 2012.

Narasingarao, et al., "De novo metagenomic assembly reveals abundant novel major lineage of Archaea in hypersaline microbial communities," The ISME Journal, vol. 6, pp. 81-93, 2012.

Peng, et al., "IDBA-UD: a de novo assembler for single-cell and metagenomic sequencing data with highly uneven depth," Bioinformatices, vol. 28, No. 11, pp. 1420-1428, 2012.

Prabhakara, et al., "Unsupervised Two-way Clustering of Metagenomic Sequences," J Biomed Biotechnol ePub, pp. 1-12, Apr. 5, 2012.

Qin, et al., "A human gut microbial gene catalog established by metagenomic sequencing," Nature, vol. 464, pp. 59-65, Mar. 4, 2010.

Renouf, et al., "Inventory and monitoring of wine microbial consortia," Appl Microbio Biotechnol, vol. 75, pp. 149-164, Jan. 19, 2017.

Rinke, et al., Insights into the phylogeny and coding potential of microbial dark matter, Nature, vol. 499, pp. 431-437, Jul. 25, 2013.

Saeed, et al., "Unsupervised discovery of microbial population structure within metagenomes using nucleotide base composition," Nucleic Acids Research, pp. 1-14, 2011.

(56) References Cited

OTHER PUBLICATIONS

Schwartz, et al., "Ordered Restriction Maps of *Saccharomyces cerevisiae* Chromosomes Constructed by Optical Mapping," Science, vol. 262, pp. 110-114, Jan. 10, 1993.
Sexton, et al., "Three-Dimensional Folding and Functional Organization Principles of the *Drosophilia* Genome," Cell, vol. 148, pp. 458-472, Feb. 3, 2012.
Sharon, et al., "Time series community genomics analysis reveals rapid shifts in bacterial species, strains, and phage during infant gut colonization," Genome Reesearch, vol. 23, pp. 111-120, 2013.
Shendure, et al., "The expanding scope of DNA sequencing," Nature Biotechnology, vol. 30, No. 11, pp. 1084-1094, Nov. 2012.
Shendure, et al., "Next-generation DNA sequencing," Nature Biotechnology, vol. 26, No. 10, Oct. 2008.
Sievers, et al., "Fast, scalable generation of high-quality protein multiple sequence alignments using Clustal Omega," Molecular Systems Biology, vol. 7, No. 539, pp. 1-6, 2011.
Simonis, et al., High-resolution identification of balanced and complex chromosomal rearrangements by 4C technology, Nature Methods, vol. 6, No. 11, pp. 837-844, Nov. 2009.
Umbarger, et al., "The Three-Dimensional Architecture of a Bacterial Genome," Mo Cell., vol. 44, No. 2, pp. 1-25, Oct. 21, 2011.
Van Berkum, et al., "Hi-C: a Method to Study the Three-dimensional Architecture of Genomes.," Journal of Visualized Experiments, vol. 39, pp. 1-7, May 2010.
Venter, et al., "Environmental Genome Shotgun Sequencing of the Sargasso Sea," Science, vol. 304, pp. 66-75, Apr. 2, 2004.
USPTO, International Search Report and Written Opinion, PCT/US2014/057930, 11 pp., dated Dec. 16, 2014.
Wood, et al., "Kraken: ultrafast metagenomic sequence classification using exact alignments," Gnome Biology, vol. 14, pp. 1-12, 2014.
WIPO, International Preliminary Report on Patentability, PCT/US2014/057930, 10 pp., dated Apr. 7, 2016.
Xin, et al., "Characterization of three endophytic, indole-3-acetic acid-producing yeasts occurring in *Populus* trees," Mycological Research, vol. 113, pp. 973-980, 2009.
Yaffee, et al., "Probabilistic modeling of Hi-C contact maps eliminates systematic biases to characterize global chromosomal architecture," Nature Genetics, vol. 43, No. 11, pp. 1059-1067, Nov. 2011.
Zhang, et al., "The oyster genome reveals stress adaptation and complexity of shell formation," Nature, vol. 490, pp. 49-54, Oct. 4, 2012.
Zhang, et al., "The genome of *Prunus mume*,"Nature Communications, vol. 3, pp. 1-8, Dec. 27, 2012.
Chen, K. et al. "Bioinformatics for Whole-Genome Shotgun Sequencing of Microbial Communities" PLoS Computational Biology, Jul. 2005, vol. 1, Issue 2, 7 pages.
Burton, J. et al. "Species-Level Deconvolution of Metagenome Assemblies with Hi-C-Based Contact Probability Maps" Genes, Genomes, Genetics, Jul. 2014, vol. 4, pp. 1339-1346.
EPO, Examination Report for European Patent Application No. 14846949.7. dated Nov. 8, 2019. 5 pages.

\* cited by examiner

FIG. 5
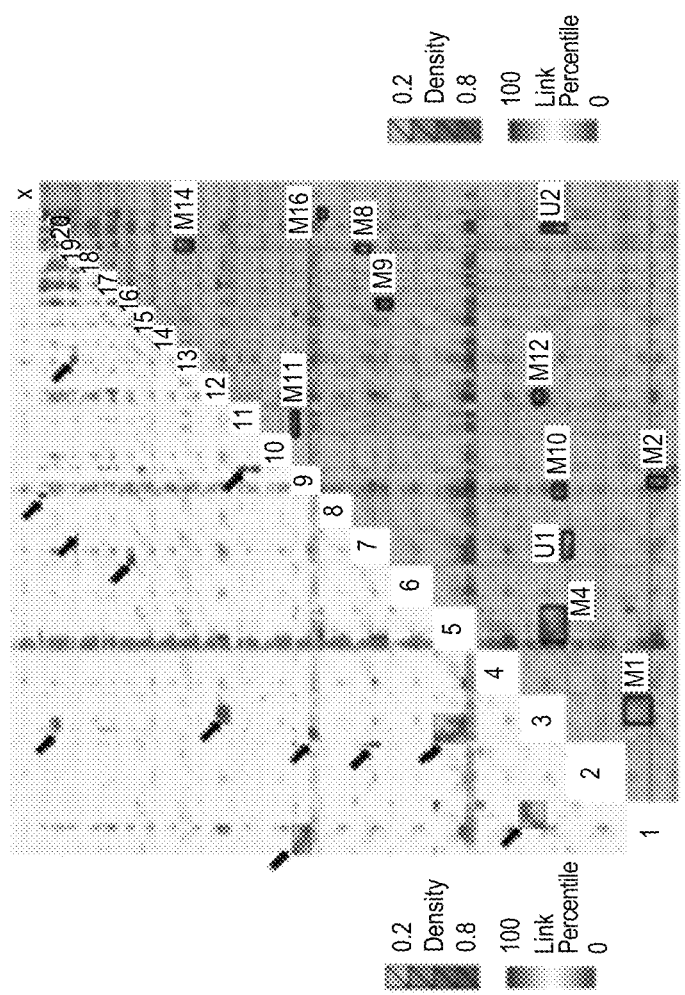
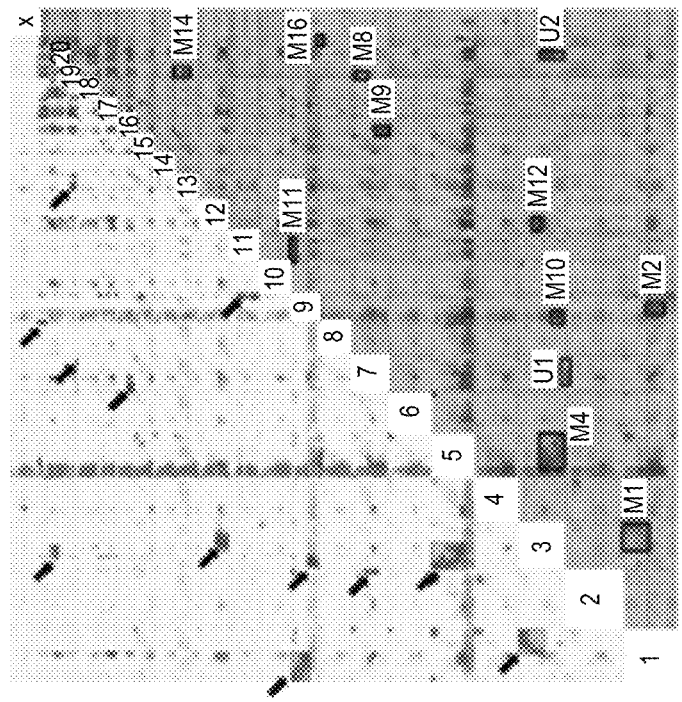

| | Metric | De novo assemblies | | | |
|---|---|---|---|---|---|
| | | Human | Human hi-contiguity, from ref. 6 | Mouse | *Drosophila* |
| Assembly metrics | Total assembly length (Mb) | 2,739 | 2,773 | 2,370 | 127.2 |
| | Length / reference length | 93.0% | 94.1% | 87.0% | 75.4% |
| | N. contigs or scaffolds | 18,921 | 3,811 | 25,964 | 7,109 |
| | N50 contig or N50 scaffold size (Kb) | 437 | 11,547 | 224 | 68 |
| | % sequence (% contigs) clustered into groups | 98.2% (71.5%) | 99.0% (53.3%) | 98.0% (87.8%) | 81.2% (64.3%) |
| | % clustered sequence (% contigs) mis-clustered | 0.14% (1.4%) | 4.7% (7.9%) | 0.24% (0.5%) | 3.4% (10.5%) |
| Full orders | % clustered seq. (% contigs) ordered | 94.4% (55.3%) | 99.4% (28.6%) | 86.7% (42.7%) | 82.0% (24.5%) |
| | % ordered seq. (% contigs) w/ ordering errors | 0.5% (0.8%) | 8.4% (9.5%) | 0.5% (1.1%) | 4.6% (5.2%) |
| | % ordered seq. (% contigs) w/ orientation errors | 1.2% (2.5%) | 6.4% (10.3%) | 1.9% (4.6%) | 4.1% (6.1%) |
| | % ordered seq. (% contigs) w/ high quality | 92.8% (79.0%) | 88.4% (51.6%) | 93.3% (82.9%) | 94.1% (88.1%) |
| | % high-quality seq. (% contigs) w/ ordering errors | 0.3% (0.4%) | 4.7% (3.7%) | 0.3% (0.7%) | 3.3% (3.4%) |
| | % high-quality seq. (% contigs) w/ orientation errors | 0.4% (0.5%) | 3.4% (3.3%) | 0.5% (1.0%) | 2.5% (2.7%) |
| Trunks | % ordered seq. (% contigs) in trunks | 88.4% (88.5%) | 82.4% (76.2%) | 90.4% (88.4%) | 70.7% (70.6%) |
| | % seq. in trunks (% contigs) w/ ordering errors | 0.2% (0.4%) | 5.3% (7.5%) | 0.2% (0.4%) | 3.0% (4.0%) |
| | % seq. in trunks (% contigs) w/ orientation errors | 1.1% (2.3%) | 2.8% (7.5%) | 1.7% (4.2%) | 1.9% (3.5%) |
| | % seq. in trunks (% contigs) w/ high quality | 93.0% (79.4%) | 92.4% (56.8%) | 93.6% (83.5%) | 94.7% (89.6%) |
| | % high-quality seq. in trunks (% contigs) w/ ordering errors | 0.1% (0.2%) | 3.0% (2.0%) | 0.1% (0.2%) | 2.1% (2.5%) |
| | % high-quality seq. in trunks (% contigs) w/ orientation errors | 0.3% (0.3%) | 1.0% (0.8%) | 0.4% (0.8%) | 1.1% (1.6%) |

FIG. 41

| Figure | Dominant chrom(s) | Sequence length in proximal contigs | | | | Sequence length in distal contigs | | | |
|---|---|---|---|---|---|---|---|---|---|
| | | Total (Mb) | Percent aligning to... | | | Total (Mb) | Percent aligning to... | | |
| | | | Dominant chrom(s) | Other chroms | None | | Dominant chrom(s) | Other chroms | None |
| 3a | chr1 | 210.9 | 99.9% | 0.01% | 0.07% | 202.6 | 100% | - | - |
| 3b | chr2 | 224.4 | 99.9% | 0.02% | 0.05% | 216.8 | 100% | - | - |
| 3c | chr3 | 190.6 | 99.3% | 0.6% | 0.02% | 182.8 | 99.3% | 0.7% | - |
| 3d | chr4 | 181.0 | 99.98% | 0.01% | 0.01% | 173.6 | 100% | - | - |
| 3e | chr5 | 170.5 | 99.9% | 0.01% | 0.09% | 162.1 | 100% | - | - |
| 3f | chr6 | 164.9 | 99.2% | 0.8% | 0.02% | 156.8 | 99.2% | 0.8% | - |
| 3g | chr7 | 143.9 | 99.8% | 0.03% | 0.18% | 134.8 | 100% | - | - |
| 3h | chr8 | 136.7 | 99.8% | 0.15% | 0.01% | 131.3 | 99.9% | 0.1% | - |
| 3i | chr9 | 106.7 | 99.9% | 0.03% | 0.09% | 101.0 | 100% | - | - |
| 3j | chr10 | 125.9 | 99.6% | 0.3% | 0.09% | 119.8 | 99.8% | 0.2% | - |
| 3k | chr11 | 125.7 | 99.9% | 0.01% | 0.10% | 118.3 | 99.99% | 0.01% | - |
| 3l | chr12 | 126.0 | 99.9% | 0.1% | 0.4% | 119.8 | 99.9% | 0.1% | - |
| 3m | chr13 | 93.9 | 99.96% | 0.007% | 0.03% | 92.2 | 100% | - | - |
| 3n | chr14 | 84.8 | 99.7% | 0.2% | 0.05% | 81.4 | 99.8% | 0.2% | - |
| 3o | chr15 | 75.5 | 99.8% | 0.01% | 0.2% | 71.0 | 100% | - | - |
| 3p | chr16 | 68.3 | 99.6% | 0.06% | 0.3% | 64.3 | 100% | - | - |
| 3q | chr17 | 73.4 | 99.7% | 0.1% | 0.2% | 65.9 | 100% | - | - |
| 3r | chr18 | 72.4 | 99.95% | 0.02% | 0.04% | 70.8 | 100% | - | - |
| 3s | chr19, chr22 | 62.8 | 99.9% | 0.1% | 0.03% | 67.9 | 57.6%, 42.4% | - | - |
| 3t | chr20, chr21 | 91.2 | 99.8% | 0.2% | 0.01% | 88.0 | 63.2%, 36.6% | 0.2% | - |
| 3u | chrX | 36.7 | 99.9% | 0.03% | 0.05% | 34.8 | 100% | - | - |
| 3v | chrX | 104.5 | 99.5% | 0.01% | 0.4% | 90.9 | 100% | - | - |
| Supp. Figure 4w | chr16 | 6.5 | 23.5% | 47.6% | 29.0% | 2.3 | 42.8% | 54.2% | 3.0% |

FIG. 42

| Repeat type | UCSC Genome Browser track name | Enrichment near the edges of mis-ordered scaffolds |
|---|---|---|
| Segmental duplications (>1 Kb length, >90% similarity) | Segmental Dups | 6.38 |
| Microsatellite repeats (dinucleotide, trinucleotide) | Microsatellite | 1.24 |
| Simple tandem repeats (4 or more nucleotides) | Simple Repeats | 2.87 |
| RepeatMasked regions | RepeatMasker | 0.93 |
| Interrupted repeats called by RepeatMasker | Interrupted Rpts | 0.94 |

FIG. 43

| Supp Figure | Dominant chrom(s) | Sequence length in grouped scaffolds | | | | Sequence length in ordered scaffolds | | | |
|---|---|---|---|---|---|---|---|---|---|
| | | Total (Mb) | Percent aligning to... | | | Total (Mb) | Percent aligning to... | | |
| | | | Dominant chrom(s) | Other chroms | None | | Dominant chrom(s) | Other chroms | None |
| 7a | chr1 | 176.5 | 99.7% | 0.3% | 0.02% | 150.8 | 99.7% | 0.3% | - |
| 7b | chr2 | 167.3 | 99.3% | 0.6% | 0.1% | 149.4 | 99.4% | 0.6% | - |
| 7c | chr3 | 142.0 | 99.8% | 0.2% | 0.04% | 119.8 | 99.9% | 0.1% | - |
| 7d | chr4 | 136.2 | 99.9% | 0.008% | 0.1% | 118.0 | 100% | - | - |
| 7e | chr5 | 136.2 | 99.93% | 0.02% | 0.05% | 119.1 | 100% | - | - |
| 7f | chr6 | 134.6 | 99.7% | 0.2% | 0.1% | 114.1 | 99.8% | 0.2% | - |
| 7g | chr7 | 120.2 | 99.8% | 0.01% | 0.2% | 102.4 | 100% | - | - |
| 7h | chr8 | 119.6 | 97.8% | 2.2% | 0.04% | 106.5 | 97.6% | 2.4% | - |
| 7i | chr9 | 113.9 | 99.93% | 0.01% | 0.06% | 103.1 | 100% | - | - |
| 7j | chr10 | 116.5 | 99.8% | 0.1% | 0.1% | 101.0 | 99.9% | 0.1% | - |
| 7k | chr11 | 113.8 | 99.5% | 0.4% | 0.06% | 106.8 | 99.5% | 0.5% | - |
| 7l | chr12 | 104.7 | 99.9% | 0.02% | 0.1% | 89.9 | 100% | - | - |
| 7m | chr13 | 106.1 | 99.8% | 0.02% | 0.2% | 91.9 | 100% | - | - |
| 7n | chr14 | 106.2 | 99.8% | 0.002% | 0.2% | 92.1 | 100% | - | - |
| 7o | chr15 | 95.2 | 99.96% | 0.03% | 0.02% | 83.7 | 100% | - | - |
| 7p | chr16 | 89.6 | 99.99% | 0.003% | 0.004% | 79.0 | 100% | - | - |
| 7q | chr17 | 84.3 | 99.7% | 0.06% | 0.2% | 73.1 | 100% | - | - |
| 7r | chr18 | 82.3 | 99.93% | 0.06% | 0.003% | 73.1 | 100% | - | - |
| 7s | chr19 | 55.6 | 99.94% | 0.01% | 0.04% | 50.3 | 100% | - | - |
| 7t | chrX | 122.4 | 99.7% | 0.1% | 0.2% | 90.9 | 99.9% | 0.1% | - |

FIG. 44

| Sub-Figure | Dominant chrom | Sequence length in grouped contigs | | | | Sequence length in ordered contigs | | | |
|---|---|---|---|---|---|---|---|---|---|
| | | Total (Mb) | Percent aligning to... | | | Total (Mb) | Percent aligning to... | | |
| | | | Dominant chrom | Other chroms | No euchromatic sequence | | Dominant chrom | Other chroms | No euchromatic sequence |
| 9b | X | 18.4 | 75.8% | 2.3% | 21.9% | 12.9 | 85.0% | 2.7% | 12.3% |
| 9c | 4 | 2.5 | 46.5% | 21.9% | 31.7% | 0.74 | 93.2% | 4.0% | 2.8% |
| 9d | 2 | 41.1 | 58.4% | 1.9% | 39.7% | 32.6 | 71.1% | 2.2% | 26.7% |
| 9e | 3 | 40.4 | 82.6% | 2.0% | 15.4% | 37.5 | 85.2% | 1.9% | 12.8% |

FIG. 45

| Number of Hi-C pairs, before filtering | Percent of total Hi-C coverage | % (by length) of sequence clustered | Clustering error rate, excluding fusions | % (by length) of sequence ordered | Ordering error rate | Orienting error rate |
|---|---|---|---|---|---|---|
| 51,493,359 | 7.0% | 96.22% | 1.92% | 92.67% | 14.85% | 12.53% |
| 113,961,921 | 15.5% | 97.14% | 1.86% | 92.68% | 6.28% | 6.38% |
| 175,873,230 | 24.0% | 97.08% | 0.52% | 92.81% | 4.55% | 5.02% |
| 237,662,270 | 32.4% | 97.13% | 0.57% | 92.79% | 4.02% | 4.59% |
| 404,341,129 | 55.1% | 98.11% | 0.73% | 93.02% | 0.96% | 1.72% |
| 568,435,079 | 77.4% | 98.24% | 0.73% | 93.02% | 0.84% | 1.41% |
| 734,185,216 | 100% | 98.22% | 0.15% | 93.06% | 0.51% | 1.23% |

FIG. 46

| Genus | Species | In sample | | | | Reference | | | |
|---|---|---|---|---|---|---|---|---|---|
| | | Strain | Source | Ploidy | Optical density | Strain | Size (Mb) | Download source | Finished? |
| Saccharomyces | cerevisiae | FY4H | M. Dunham | 1 | 0.079088 | FY | 12.2 | downloads.yeastgenome.org | Yes |
| Saccharomyces | cerevisiae | CEN.PK | P. Kotter | 1 | 0.071645 | CEN.PK | 12.5 | downloads.yeastgenome.org | No |
| Saccharomyces | cerevisiae | RM11-1A | L. Kruglyak | 1 | 0.084903 | RM11-1A | 11.7 | www.broadinstitute.org | Yes |
| Saccharomyces | cerevisiae | SK1 | A. Deutschbauer | 2 | 0.075366 | SK1 | 11.9 | cbio.mskcc.org/public/SK1_MvO/ | Yes |
| Saccharomyces | paradoxus | YDG613 | D. Greig | 2 | 0.076762 | | 11.7 | saccharomycessensustricto.org | Yes |
| Saccharomyces | mikatae | FM356 | M. Johnston | 2 | 0.08188 | IFO 1815 | 11.5 | saccharomycessensustricto.org | Yes |
| Saccharomyces | kudriavzevii | FM527 | M. Johnston | 2 | 0.008141 | IFO 1802 | 11.5 | saccharomycessensustricto.org | Yes |
| Saccharomyces bayanus var. uvarum | | YZ85-113 | Y. Zhang | 1 | 0.055827 | CBS 7001 | 11.5 | saccharomycessensustricto.org | Yes |
| Naumovozyma (Saccharomyces) | castellii | 4310 | D. Bartel | 1 | 0.082577 | NRRL Y-12630 | 11.2 | downloads.yeastgenome.org | No |
| Lachancea | waltii | kwaltiura3 | B. Brewer | 1 | 0.086067 | NRRL Y-8285 | 10.2 | fangman-brewer-gbrowse.gs.washington.edu | Mostly |
| Lachancea (Saccharomyces) | kluyveri | FM628 | M. Johnston | 1 | 0.096534 | CBS 3082 | 11.3 | genolevures.org/sakl.html | Yes |
| Kluyveromyces | lactis | MW98-8C | C. Newlon | 1 | 0.055827 | NRRL Y-1140 | 10.7 | genolevures.org/klla.html | Yes |
| Kluyveromyces | wickerhamii | Y-8286 | USDA/ARS | 1 | 0.062805 | UCD 54-210 | 9.81 | www.ncbi.nlm.nih.gov | No |
| Ashbya (Eremothecium) | gossypii | WT | S. Jaspersen | 1 | Can't measure | ATCC 10895 | 8.74 | genolevures.org/ergo.html | Yes |
| Scheffersomyces (Pichia) | stipitis | Y-11545 | USDA/ARS | 1 | 0.080251 | CBS 6054 | 15.4 | www.ncbi.nlm.nih.gov | Yes |
| Pichia (Komagataella) | pastoris | JC308 | J. Cregg | 1 | 0.002326 | GS115 | 9.21 | www.ncbi.nlm.nih.gov | Yes |

FIG. 47

| Domain | Genus | Species | In sample | | | Reference | | | Finished? |
|---|---|---|---|---|---|---|---|---|---|
| | | | Strain | Source | Optical density | Strain | Size (Mb) | Download source | |
| Eukaryota | Saccharomyces | cerevisiae | FY4H | M. Dunham | 1.02 | FY | 12.2 | downloads.yeastgenome.org | Yes |
| Eukaryota | Zygosaccharomyces | rouxii | Y-229 | USDA/ARS | 0.66 | CBS 732 | 9.76 | genolevures.org/zyro.html | Yes |
| Eukaryota | Lachancea (Kluyveromyces) | thermotolerans | Y-8284 | USDA/ARS | 0.98 | CBS 6340 | 9.39 | genolevures.org/klth.html | Yes |
| Eukaryota | Kluyveromyces | aestuarii | YB-4510 | USDA/ARS | 1.04 | ATCC 18862 | 9.95 | www.ncbi.nlm.nih.gov | No |
| Eukaryota | Hansenula (Ogataea) | polymorpha | Y-5445 | USDA/ARS | 1.21 | DL-1 | 8.86 | www.ncbi.nlm.nih.gov | Yes |
| Eukaryota | Pichia (Komagataella) | pastoris | JC 308 | J. Cregg | 0.61 | GS115 | 9.32 | www.ncbi.nlm.nih.gov | Yes |
| Eukaryota | Schizosaccharomyces | pombe | YFS 105 | N. Rhind | 0.52 | ASM294 | 12.6 | www.pombase.org | Yes |
| Eukaryota | Schizosaccharomyces | japonicus | YFS 760 | N. Rhind | 0.19 | yFS275 | 11.7 | www.broadinstitute.org | No |
| Archaea | Methanococcus | maripaludis | S2 | J. Leigh | ~0.1 | S2 | 1.67 | www.ncbi.nlm.nih.gov | Yes |
| Bacteria | Escherichia | coli | AG 111 | H. Merrikh | 0.26 | K-12 | 4.69 | www.ncbi.nlm.nih.gov | Yes |
| Bacteria | Vibrio (Aliivibrio) | fischeri | ES114 | P. Greenberg | 0.25 | ES114 | 4.27 | www.ncbi.nlm.nih.gov | Yes |
| Bacteria | Pseudomonas | fluorescens | Pf-5 | C. Harwood | 0.4 | Pf5-1 | 6.44 | www.ncbi.nlm.nih.gov | Yes |
| Bacteria | Acinetobacter | baylyi | ADP1 | C. Harwood | 0.12 | ADP1 | 3.60 | www.ncbi.nlm.nih.gov | Yes |
| Bacteria | Burkholderia | thailandensis | E264 | C. Harwood | 0.6 | E264 | 6.72 | www.ncbi.nlm.nih.gov | Yes |
| Bacteria | Agrobacterium | tumefaciens | P4 | C. Quetsch | 0.37 | P4 | 6.33 | www.ncbi.nlm.nih.gov | Mostly |
| Bacteria | Rhodopseudomonas | palustris | CGA009 | C. Harwood | 0.32 | CGA 009 | 5.47 | www.ncbi.nlm.nih.gov | Yes |
| Bacteria | Flavobacterium | johnsoniae | UW 101 | C. Harwood | 0.55 | UW 101 | 6.10 | www.ncbi.nlm.nih.gov | Yes |
| Bacteria | Bacillus | subtilis | HM1/168 | H. Merrikh | 0.35 | 168 | 4.22 | www.ncbi.nlm.nih.gov | Yes |

FIG. 48

| | M-Y (total sequence length = 135206617) | | | |
|---|---|---|---|---|
| | Sequence clustered | % clustered | Seq misclustered | % misclustered |
| Main result | 111112059 | 82.18% | 922932 | 0.83% |
| Bootstrap 1 | 111136126 | 82.20% | 4146798 | 3.73% |
| Bootstrap 2 | 111102736 | 82.17% | 4500167 | 4.05% |
| Bootstrap 3 | 111106339 | 82.18% | 4655083 | 4.19% |
| Bootstrap 4 | 111101816 | 82.17% | 4389061 | 3.95% |
| Bootstrap 5 | 111106542 | 82.18% | 4425448 | 3.98% |
| Bootstrap 6 | 111158559 | 82.21% | 4356095 | 3.92% |
| Bootstrap 7 | 111089140 | 82.16% | 4173561 | 3.76% |
| Bootstrap 8 | 110777343 | 81.93% | 1294345 | 1.17% |

| | M-PE (total sequence length = 133169811) | | | |
|---|---|---|---|---|
| | Sequence clustered | % clustered | Seq misclustered | % misclustered |
| Main result | 118841530 | 89.24% | 461626 | 0.39% |
| Bootstrap 1 | 117677687 | 88.37% | 1748183 | 1.49% |
| Bootstrap 2 | 117818421 | 88.47% | 737953 | 0.63% |
| Bootstrap 3 | 117636660 | 88.34% | 1834184 | 1.56% |
| Bootstrap 4 | 117604654 | 88.31% | 497732 | 0.42% |
| Bootstrap 5 | 117695244 | 88.38% | 509778 | 0.43% |
| Bootstrap 6 | 117566728 | 88.28% | 1600895 | 1.36% |
| Bootstrap 7 | 117679867 | 88.37% | 1870031 | 1.59% |
| Bootstrap 8 | 117760573 | 88.43% | 1748183 | 1.48% |

METHOD FOR LARGE SCALE SCAFFOLDING OF GENOME ASSEMBLIES

PRIORITY CLAIM

This application claims priority to U.S. Provisional Application No. 61/883,446, filed Sep. 27, 2013, the subject matter of which is hereby incorporated by reference as if fully set forth herein.

STATEMENT OF GOVERNMENT INTEREST

This invention was made with government support under grant nos. 5R01 HG006283 and T32HG000035, awarded by the National Institutes of Health and grant no. 1243710, awarded by the National Science Foundation. The government has certain rights in the invention.

BACKGROUND

The Human Genome Project (HGP) defined and achieved high standards for the de novo assembly of reference genomes for *H. sapiens* and key model organisms. For example, the public draft human genome, reported in 2001, contained 90% of the euchromatic sequence with an N50 of 81 kilobases (Kb) (International Human Genome Sequencing Consortium, 2001; International Human Genome Sequencing Consortium, 2004). The finished human genome, reported in 2004, contained 99% of the euchromatic sequence with an N50 of 38.5 megabases (Mb) and an error rate of 1 event per 100,000 bases (International Human Genome Sequencing Consortium, 2004). At both stages, nearly all sequences were assigned, ordered, and oriented to chromosomes, although many errors were corrected during finishing (International Human Genome Sequencing Consortium, 2004).

Next-generation DNA sequencing technologies produce billions of short reads per instrument run at a very low cost per sequenced base, empowering a wide range of experiments (Shendure & Ji 2008; Shendure & Lieberman-Aiden 2012). However, although extensive progress has been made in developing algorithms for de novo genome assembly from short reads (Compeau et al. 2011), current sequencing technologies remain remarkably distant from routinely assembling genomes to the standards set by the HGP. For example, the human genome was assembled with less than 40 gigabases (Gb) of Sanger sequencing, but next-generation de novo assemblies relying on 5- to 10-fold more sequence are highly fragmented relative to the finished chromosomes of the *H. sapiens* reference build (Gnerre et al. 2011; Li et al. 2010).

It is important to recognize that the high quality of the HGP's genome assemblies is not solely attributable to the length and accuracy of Sanger sequencing reads. Rather, a diversity of approaches was brought to bear to achieve long-range contiguity. For the human genome, this included dense genetic maps, dense physical maps, and hierarchical shotgun sequencing of a tiling path of long insert clones (International Human Genome Sequencing Consortium, 2001; International Human Genome Sequencing Consortium, 2004). Whole-genome shotgun assemblies—typically based on end sequencing of both short and long insert clones—also relied on dense genetic and physical maps to assign, order, and orient sequence contigs or scaffolds to chromosomes (Mouse Genome Sequencing Consortium, 2002).

Diverse strategies have been developed to boost the contiguity of next-generation de novo genome assemblies. These include end sequencing of fosmid clones (6), fosmid clone dilution pool sequencing (Kitzman et al. 2011; Zhang et al. 2012a), optical mapping (Schwartz et al. 1993; Zhang et al 2012b; Dong et al. 2013; Lam et al. 2012), and genetic mapping with restriction site associated DNA (RAD) tags (Baird et al. 2008). However, each of these strategies has important limitations. Fosmid libraries and optical mapping are technically challenging and provide only mid-range contiguity. Genetic maps are more powerful but are costly or impractical to generate for many species. Particularly as initiatives such as the 10K Genome Project (Genome 10K Community of Scientists, 2009) gain momentum, the genomics field is in need of scalable, broadly accessible methods enabling chromosome-scale de novo genome assembly. Therefore, it would be desirable to develop cost-effective and high quality methods to generate meaningful data for establishing long range and chromosome-scale contiguity.

SUMMARY

In some embodiments, a computational method that may be performed by a computing system is provided, wherein the method is used for large scale scaffolding of a genome assembly. Such methods may include a step of applying a location clustering model to a test set of contigs to form two or more location cluster groups, each location cluster group comprising one or more location-clustered contigs; a step of applying an ordering model to each of the two or more location cluster groups to form an ordered set of one or more location-clustered contigs within each cluster group; and a step of applying an orienting model to each ordered set of one or more location-clustered contigs to assign a relative orientation to each of the location-clustered contigs within each location cluster group. In some aspects, the test set of contigs are generated from aligning a set of reads generated by a chromosome conformation analysis technique (e.g., Hi-C) with a draft assembly, a reference assembly, or both.

In some aspects, the computational model may also include a step prior to applying a location clustering model that includes applying a species clustering model to a heterogeneous set of contigs to form two or more species cluster groups, each species cluster group comprising one or more species-clustered contigs from a single species wherein the heterogeneous set of contigs are generated from aligning a set of reads generated by a chromosome conformation analysis technique with a metagenome assembly, and wherein the one or more species-clustered contigs are used as the test set of contigs.

In other embodiments, a system for performing large scale scaffolding of a genome assembly is provided. In some aspects, the system includes a computer readable storage medium which stores computer-executable instructions that include instructions for applying a location clustering model to a test set of contigs to form two or more location cluster groups, each location cluster group comprising one or more location-clustered contigs; instructions for applying an ordering model to each of the two or more location cluster groups to form an ordered set of one or more location-clustered contigs within each cluster group; and instructions for applying an orienting model to each ordered set of one or more location-clustered contigs to assign a relative orientation to each of the location-clustered contigs within each location cluster group; wherein the test set of contigs are generated from aligning a set of reads generated by a chromosome conformation analysis technique (e.g., Hi-C) with a draft assembly, a reference assembly, or both. In some aspects, the system may also include a processor which is configured to perform steps of receiving a set of input files and executing the computer-executable instructions stored in the computer-readable storage medium. In some aspects, the input files may include a file comprising the set of reads generated by a chromosome conformation analysis technique (e.g., Hi-C); and the draft assembly, reference assembly, or both.

In another embodiment, a computer readable storage medium which stores computer-executable instructions is provided. In some embodiments, the instructions may include instructions for applying a location clustering model to a test set of contigs to form two or more location cluster groups, each location cluster group comprising one or more location-clustered contigs; instructions for applying an ordering model to each of the two or more location cluster groups to form an ordered set of one or more location-clustered contigs within each cluster group; and instructions for applying an orienting model to each ordered set of one or more location-clustered contigs to assign a relative orientation to each of the location-clustered contigs within each location cluster group; wherein the test set of contigs are generated from aligning a set of reads generated by a chromosome conformation analysis technique with a draft assembly, a reference assembly, or both.

In some aspects, the computer-executable instructions in the embodiments above further comprise instructions for applying a species clustering model to a heterogeneous set of contigs to form two or more species cluster groups, each species cluster group comprising one or more species-clustered contigs from a single species; wherein the heterogeneous set of contigs are generated from aligning a set of reads generated by a chromosome conformation analysis technique with a metagenome assembly, and wherein the one or more species-clustered contigs are used as the test set of contigs in the instructions for applying a location clustering model.

BRIEF DESCRIPTION OF THE DRAWINGS

FIG. 1a. The input is a set of contigs (or scaffolds) from a draft assembly and a set of genome-wide chromosome interaction data, e.g., Hi-C links. FIG. 1b. Contigs on the same chromosome tend to have more Hi-C links between them, relative to contigs on different chromosomes. LACHESIS exploits this to cluster the contigs into groups that largely correspond to individual chromosomes. FIG. 1c. Within a chromosome, contigs in close proximity tend to have more links than contigs that are distant. LACHESIS exploits this to order the contigs within each chromosome group. FIG. 1d. Lastly, LACHESIS uses the exact position of links between adjacent contigs to predict the relative orientation of each contig.

FIG. 2a. An assembly having five contigs, which in truth belong to two chromosomes (green and blue). Hi-C links between the contigs are shown as black dotted lines, with thicker lines indicating higher normalized link density. FIG. 2b. The agglomerative hierarchical clustering algorithm begins. The two contigs sharing the highest normalized link density are merged together to create a cluster (gray oval). The new link densities between this cluster and each other contig (orange dotted lines) are calculated as the average (normalized) linkage between the two contigs in this cluster and the other contig. FIG. 2c. Again, the two contigs sharing the highest normalized link density are merged to create a cluster. New average link densities are calculated (magenta dotted lines); note that the link density between the two multi-contig clusters is the average of four original link densities. FIG. 2d. Another merge. The user-specified limit of two clusters has been reached, so the algorithm is complete. It has correctly found groups for each chromosome.

FIG. 3a. A group of contigs depicted as a graph. Each blue vertex indicates a contig, and the edges between vertices indicate normalized Hi-C link densities (for clarity, edges are not shown between all pairs of contigs). FIG. 3b. A spanning tree (a set of edges that connects all vertices with no loops) is found (green edges). The edges of the spanning tree are chosen to have the maximum possible link densities. Short contigs (dark brown dots) are not included in the spanning tree. FIG. 3c. The longest path in the spanning tree (magenta dots, orange edges) is found. This path constitutes the "trunk", an initial contig ordering with high accuracy but low completeness. FIG. 3d. The trunk is removed from the spanning tree, leaving a set of vertices and edges called "branches", many of which have a single isolated vertex. FIG. 3e. Lastly, the branches are considered for reinsertion into the trunk at all possible positions and orientations. Each possible reinsertion site is given a "score" equal to the sum of the reciprocals of all link distances. Very short branches are not reinserted. f. The final contig ordering.

FIG. 4a. A pair of contigs connected by several Hi-C links, with the exact location of the aligned Hi-C reads shown (orange dotted lines). All of the reads in these links are localized to one end of each contig, which suggests that the contigs should be placed in the orientation shown; any other orientation would increase the perceived length of the links. Note that this is the first time LACHESIS uses the exact location of the reads in a Hi-C link, as opposed to the mere fact of a link between two contigs. b. An ordering of four contigs A,B,C,D, with arbitrary initial orientations. The exact locations of the Hi-C read alignments between adjacent contigs shown (for clarity, only one link per adjacency is shown). c. A weighted directed acyclic graph (WDAG) describing all possible ways in which these four contigs could be ordered. The edges exiting the start node and entering the end note all have the same weight. The edge weights between each pair of contigs (arrows) are set to the log-likelihoods of observing the Hi-C links between those two contigs in the two orientations, given that longer links are less likely; larger numbers (thicker arrows) indicate more likely orientations. The likeliest path through the WDAG (magenta arrows) is shown. The orientation quality score is calculated as the differential to the log-likelihood caused by choosing a particular orientation; for example, for contig B, the log-likelihood is the difference between the weights of the magenta arrows entering and leaving node Bfw and the weights of the alternative nodes entering and leaving Brc (dark green arrows). d. The contig orientations corresponding to the likeliest path found in c.

FIG. 5 illustrates the use of Hi-C to detect interchromosomal rearrangements in HeLa with high sensitivity according to some embodiments. In the top left half of each image, blue horizontal lines represent outlying stretches of link scores with ≥10 windows, of which ≥80% of windows are ≥1 standard deviation above the mean of the row. Likewise, vertical red lines represent similar outlying stretches with respect to columns. Windows called as both row and column outliers are designated "outlier windows". Regions with excessive outlier stretch calls (e.g., chromosome 5p) are only called as rows or columns and not likely both, thus reducing noise due to globally high scoring regions of the genome. Outlier window points are then clustered and called as potential fusions (purple boxes) and scored according to the density of outlier points within the window. a. An inclusive approach yields 100% sensitivity for detecting previously identified marker chromosomes, yet only 8% specificity (assuming no additional marker chromosomes beyond those previously identified). False positive calls are largely due to increased chromosomal contact between the smaller, gene-rich chromosomes naturally present in healthy cells. b. Specificity can be increased by filtering based on cluster area. Specificity increases to 31% but sensitivity drops to 92%, with a bias towards rearrangements involving larger chromosomes or large regions of chromosomes.

FIG. 6a. The results of LACHESIS clustering on the de novo human assembly. Shown on the x-axis are the 7,083 scaffolds (total length: 2.49 Gb) that are large (≥25 AAGCTT restriction sites) and not repetitive (Hi-C link density less than 2 times average), which LACHESIS uses as informative for clustering. The y-axis shows the 23 groups created by LACHESIS, with the order chosen for the purposes of clarity. The color scheme is the standard SKY (spectral karyotyping) color scheme for human. FIG. 6b. The results of LACHESIS ordering and orienting on the group of 913 scaffolds from a (total length: 211 Mb) that corresponds to human chromosome 1. On the x-axis are the scaffolds that have been clustered into this group, in true chromosomal order. On the y-axis is the order in which LACHESIS has placed these scaffolds. Also listed in the panel are the chromosome name, the number of scaffolds in the derived ordering, and the reference length of this chromosome. FIG. 6c. The results of LACHESIS clustering on the de novo mouse assembly. Shown on the x-axis are the 8,594 scaffolds (total length: 1.94 Gb) that are large and not repetitive, which LACHESIS uses as informative for clustering. The y-axis shows the 20 groups created by LACHESIS, with the order chosen for the purposes of clarity. The color scheme is as in FIG. 6a. FIG. 6d. The results of LACHESIS ordering and orienting on the group of 1,772 scaffolds from FIG. 6c (total length: 177 Mb) that correspond to mouse chromosome 1. The plotting is as in FIG. 6c.

FIGS. 7a-7v show the results of LACHESIS ordering and orienting on 22 of the 23 chromosome groups in the de novo human assembly. For each ordering, only the scaffolds on the "dominant chromosome" (the chromosome containing the plurality of aligned sequence) are shown. The exceptions are two groups that correspond to fusions of small chromosomes (19 and 22 (FIG. 7s); 20 and 21 (FIG. 7t)) (see FIG. 44). Within each of these fused groups, the two chromosomes were well separated by ordering (FIG. 7s, FIG. 7t). The arms of the X chromosome clustered to two groups (FIG. 7u, FIG. 7v). Not shown is one very small chimeric group (length=6.5 Mb; see FIG. 8w). Also listed in each panel are the identity of the dominant chromosome, the number of scaffolds in the derived ordering, and the reference length of the dominant chromosome.

where $f_{species}$(library) is the fraction of reads from a sequencing library that align to the given species' reference genome. These efficiency rates were log-scaled and then normalized to create an average of 0 over all species.

Figure 27:
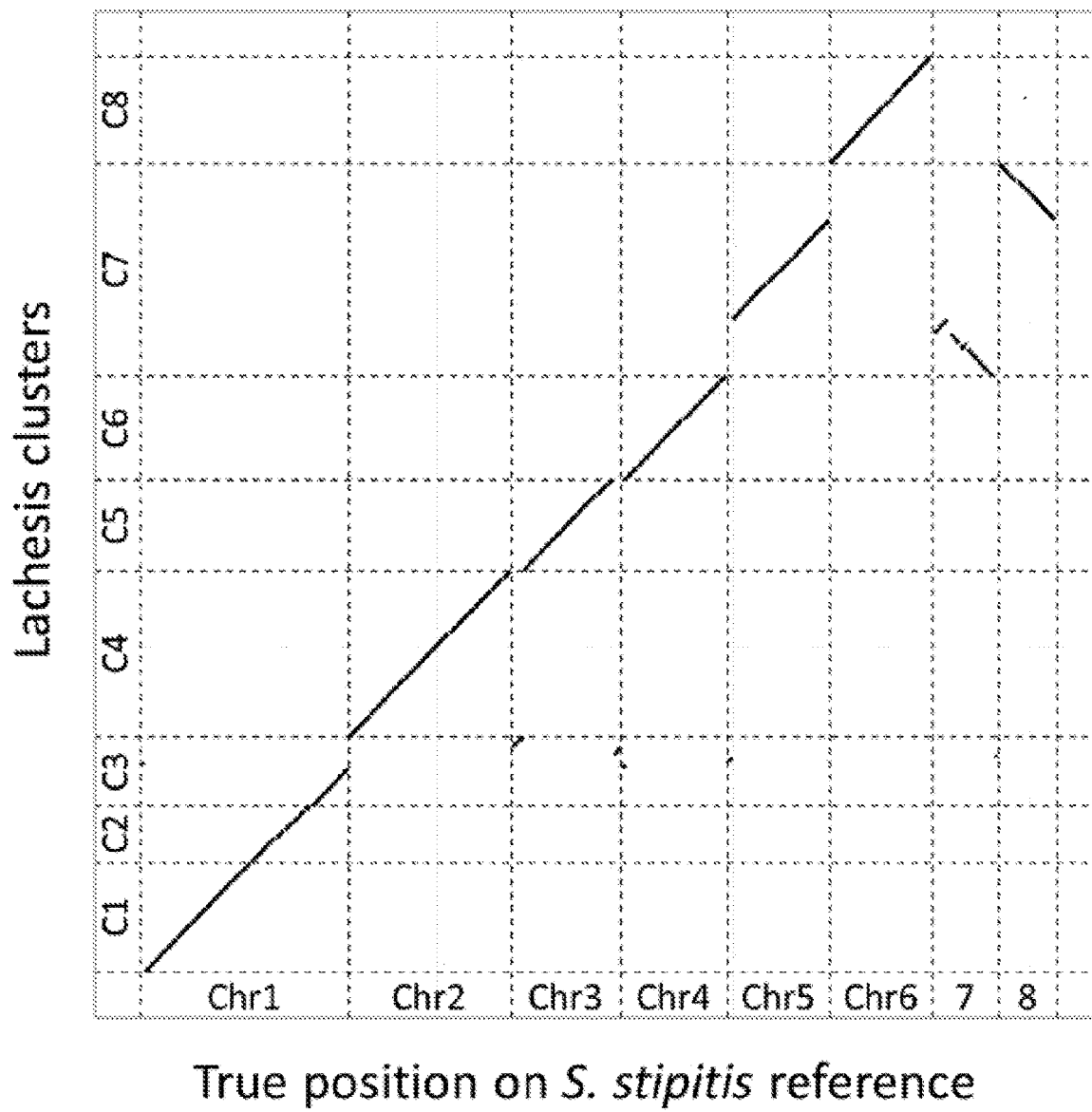

FIG. 27 shows the accuracy of Lachesis assembly of *Scheffersomyces stipitis* according to some embodiments. The contigs in the MetaPhase cluster corresponding to *S. stipitis* were clustered, ordered, and oriented with Lachesis (Burton et al. 2013) (FIG. 20C). Shown here is a validation of the Lachesis assembly. Every contig that is placed by Lachesis and which aligns to the *S. stipitis* reference genome is shown. x-axis: the contig's true position in the *S. stipitis* reference. y-axis: the contig's placement in the Lachesis assembly (note that both the order of the clusters on the y-axis and the overall orientation of each cluster are arbitrary; they are chosen here for visual clarity and are not the same as in FIG. 20C.)

Figure 28:
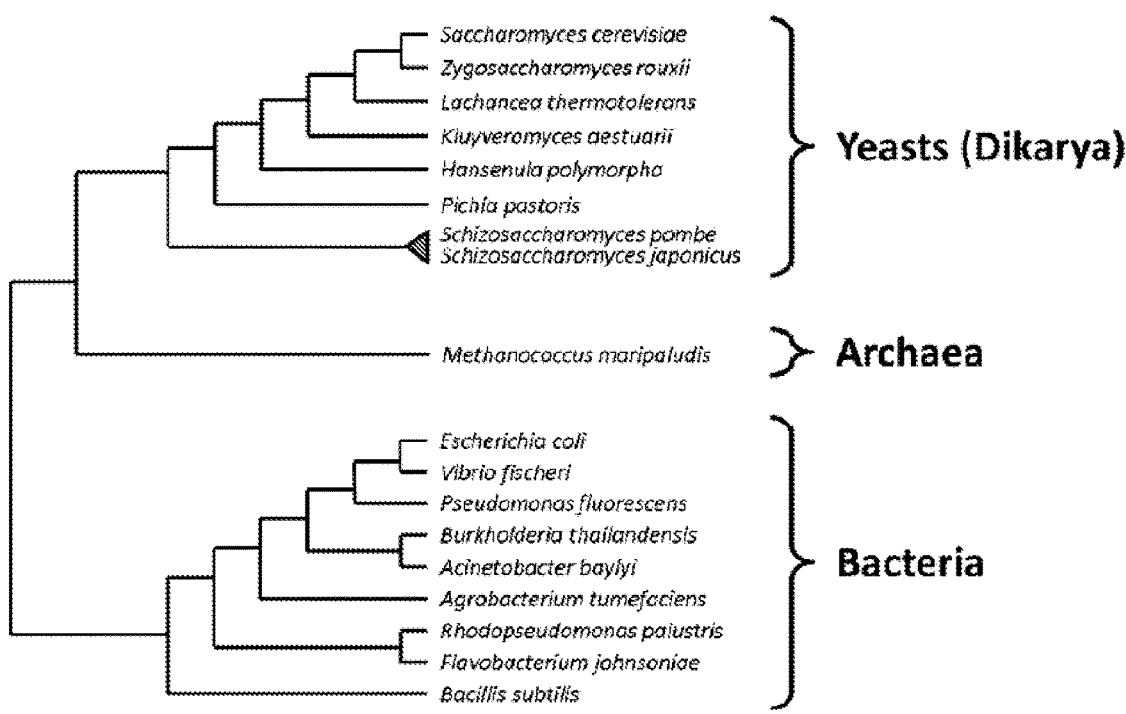

FIG. 28 shows M-3D species phylogeny. Phylogenetic tree of the 18 yeast, archaeal, and bacterial strains used in the M-3D sample (FIG. 47) according to some embodiments.

Figure 29:
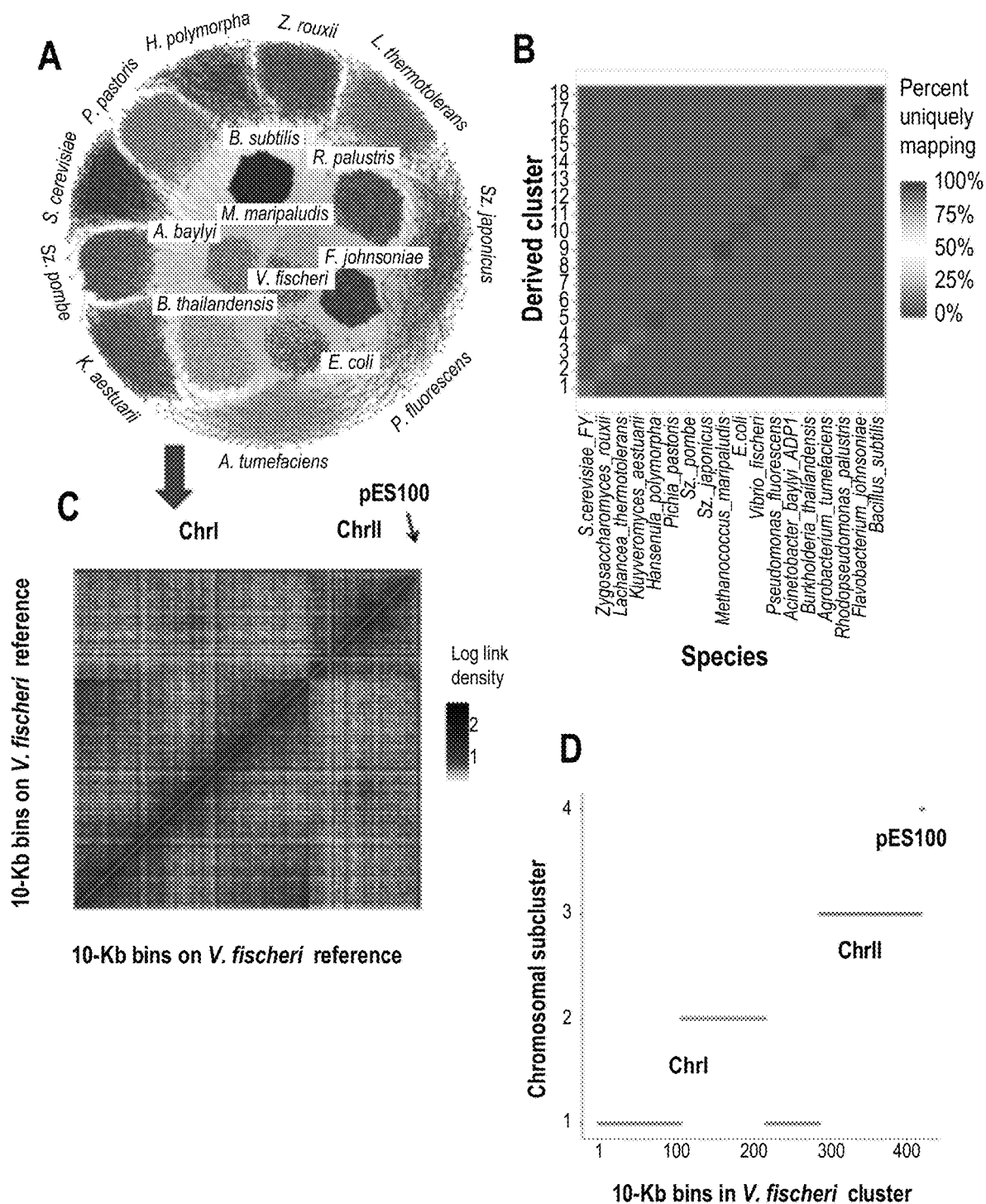

FIG. 29 shows MetaPhase clustering results on the M-3D simulated contig assembly according to some embodiments. (A) The reference genomes of the 18 species from the M-3D sample were split into 10-Kb bins. Hi-C links from the metagenome sample were then used to divide the bins into 18 clusters, one for every species. The contigs are illustrated as in FIG. 20A. Blue and green colors are yeast species; yellow is archaea; red and orange are bacteria. (B) Validation. This heatmap has the same key as FIG. 20B. (C) Heatmap of the M-3D Hi-C links aligned to the reference genome of *Vibrio fischeri*, one of the bacteria in the sample. The *V. fischeri* genome contains two chromosomes and a 46-Kb plasmid, pES100 (demarcated by dotted black lines.) This heatmap has a resolution of 10 Kb. (D) Applying Lachesis' clustering algorithm to the *V. fischeri* clustered genome to deconvolute the pES100 plasmid from the *V. fischeri* chromosomes. x-axis: the 424 simulated contigs in the *V. fischeri* cluster derived in (A,B). y-axis: the four clusters derived by Lachesis. Due to the presence of strong chromatin domains on chromosome I, Lachesis was unable to merge this chromosome into a single cluster and required an input of N=4.

Figure 30:
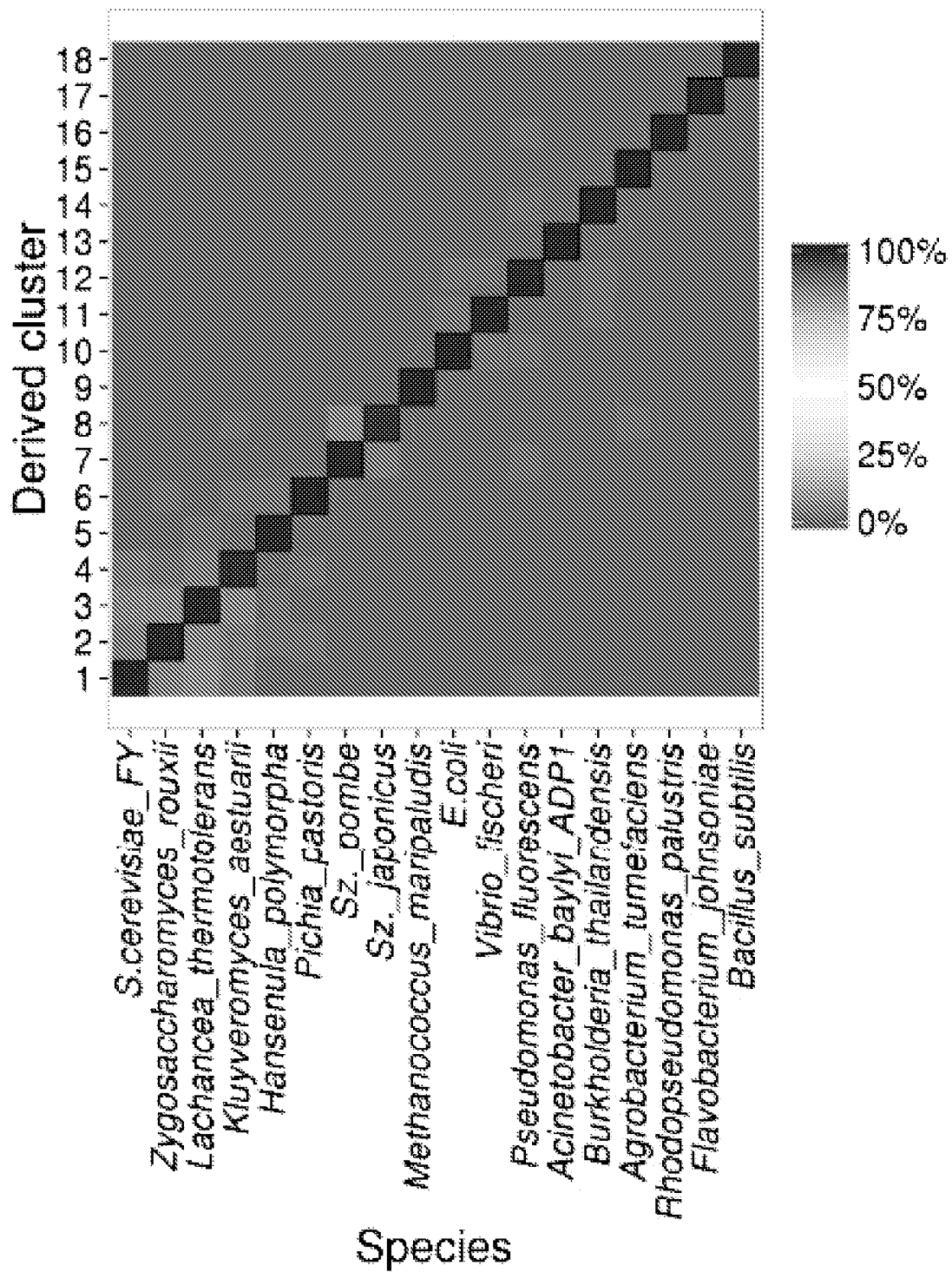

FIG. 30 is a heatmap of non-unique reference alignments of contigs in each M-3D cluster according to some embodiments. This is identical to FIG. 29B, except that all contig alignments to all genomes are shown here, whereas in FIG. 29B only contigs that align uniquely to a single reference genome are shown.

Figure 31:
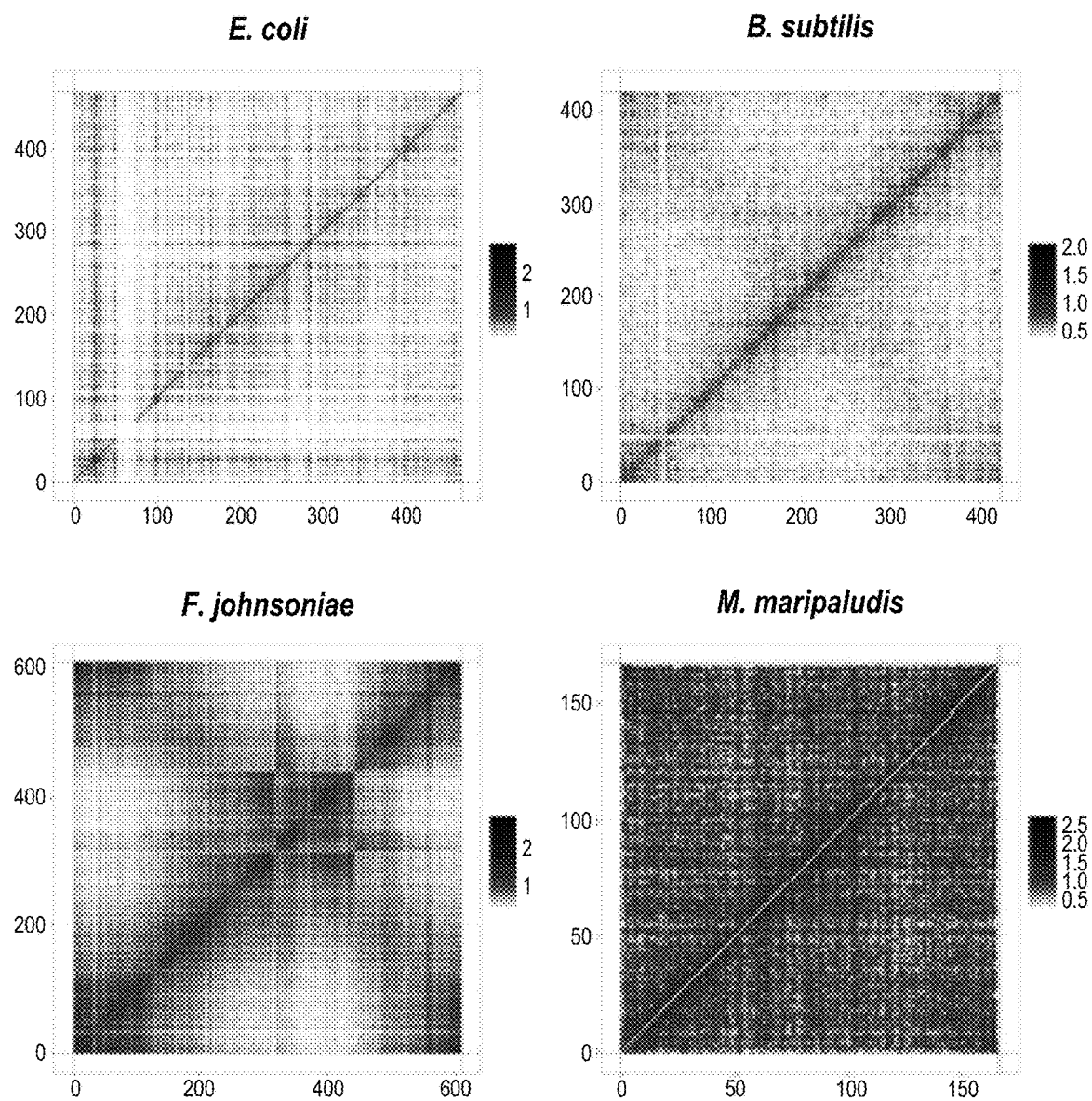

FIG. 31 are heatmaps of M-3D Hi-C links aligned to prokaryotic reference genomes according to some embodiments. Reads from the M-3D HindIII nonresuspended library (FIG. 48) were aligned to the draft assemblies of four prokaryotic species present in the M-3D sample. Each heatmap has a resolution of 10 Kb, and the legend indicates the log 10 of link density.

Figure 32:
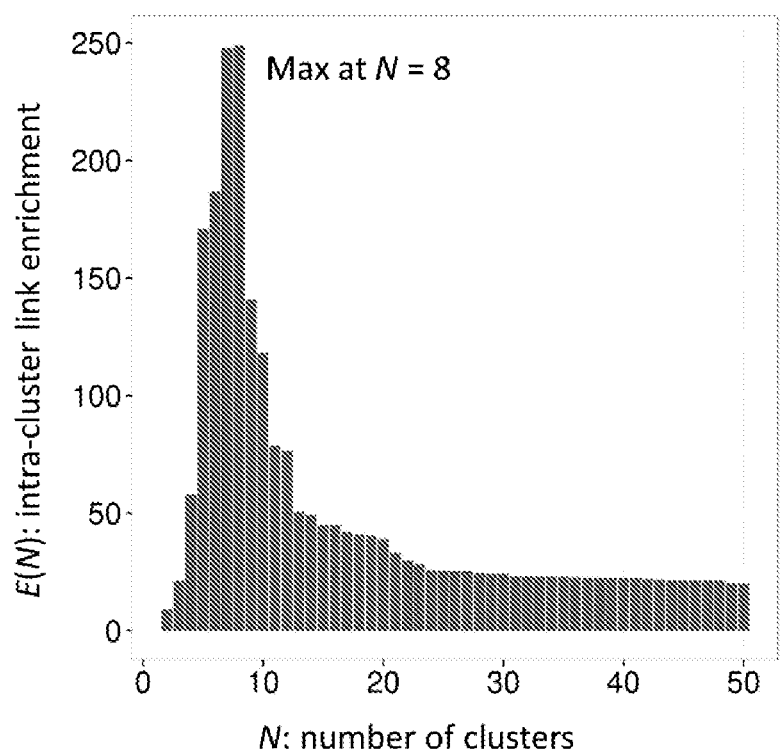

FIG. 32 is an intra-cluster enrichment curve E(N) which suggests 8 species are present in the sample according to some embodiments.

Figure 33:
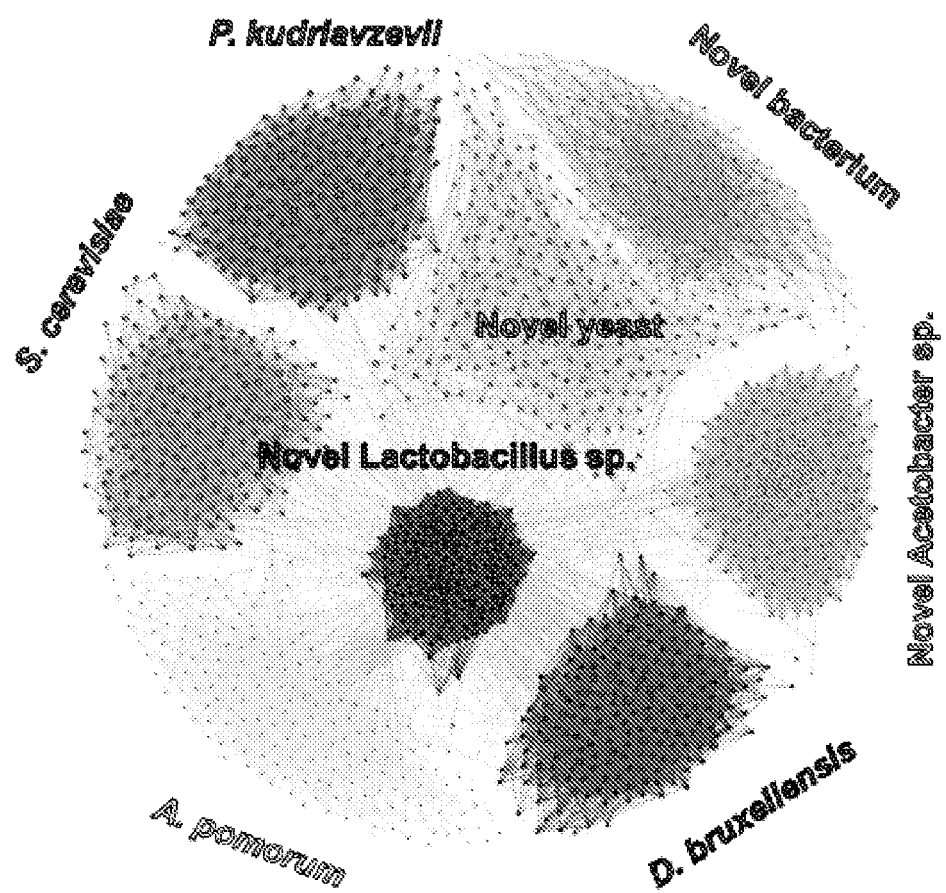

FIG. 33 shows the clustering of contigs using Hi-C interaction data generates 8 discrete clusters corresponding to 4 yeast and 4 bacterial species according to some embodiments.

Figure 34:
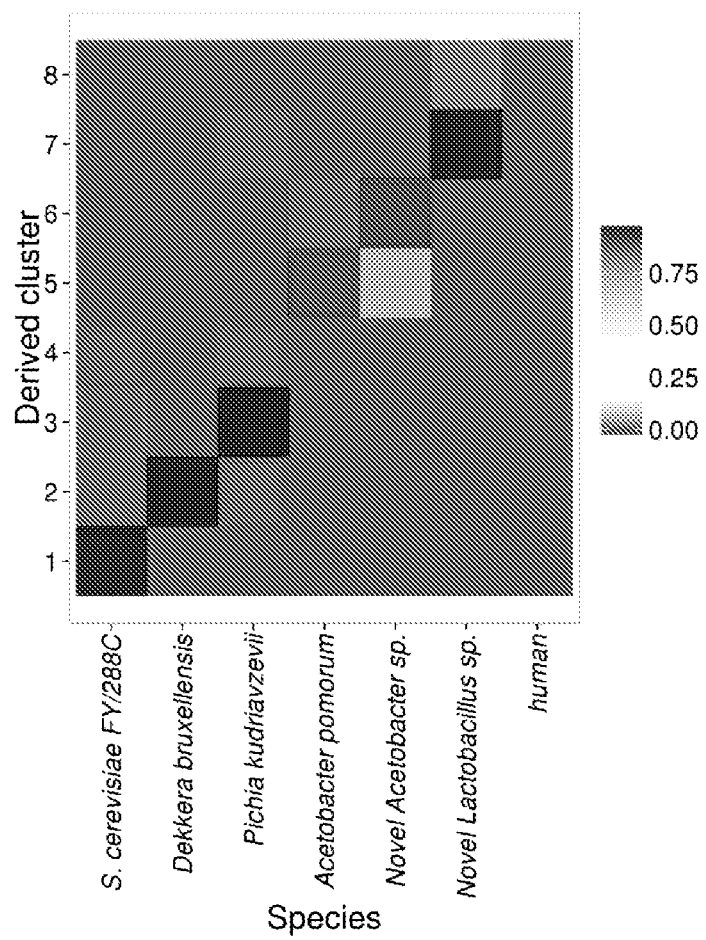

FIG. 34 shows the alignment of draft contigs in the MetaPhase clusters to the species' reference genomes according to some embodiments (including two novel draft genomes that were sequenced).

Figure 35:
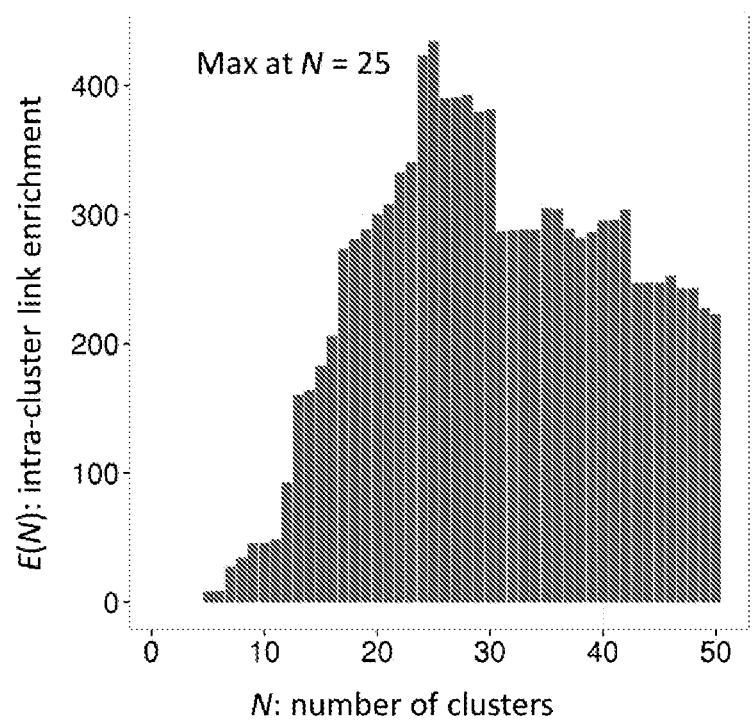

FIG. 35 is an intra-cluster enrichment curve E(N) which suggests 25 species are present in the sample according to some embodiments.

Figure 36:
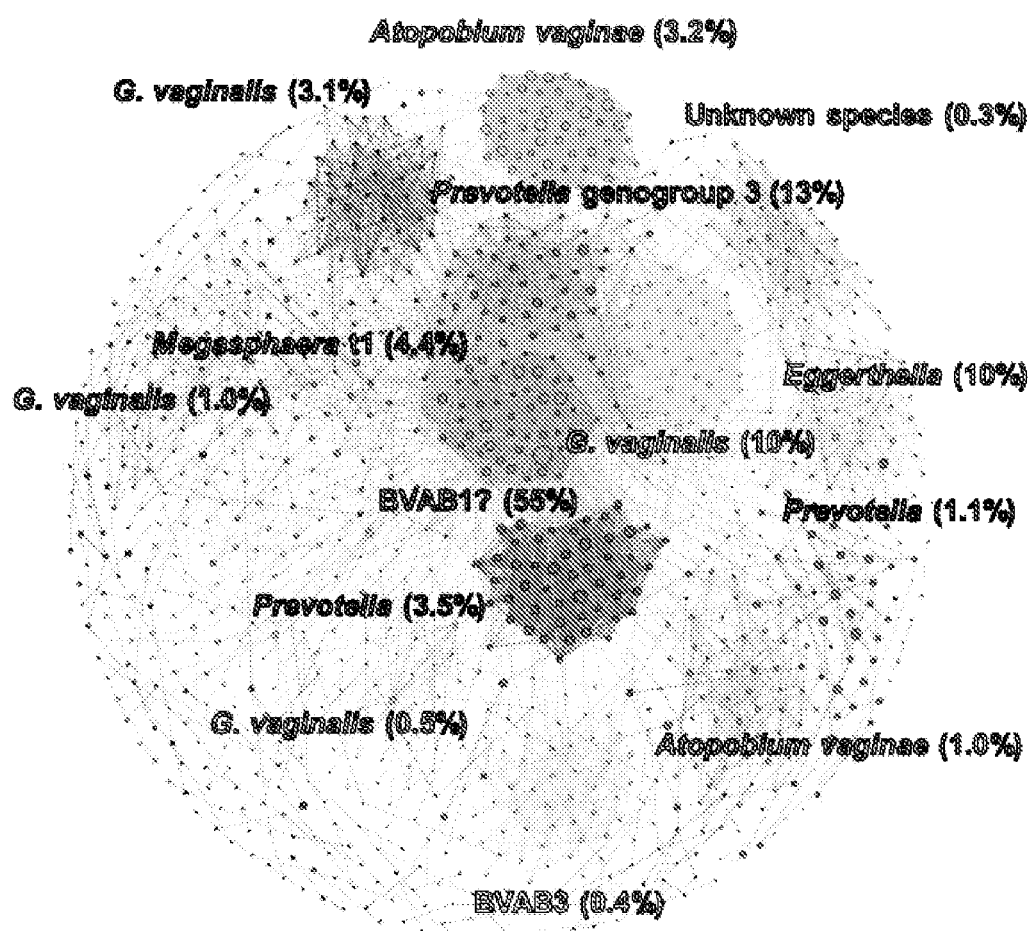

FIG. 36 shows the clustering of contigs using Hi-C interaction data creates 25 distinct clusters according to some embodiments.

Figure 37:
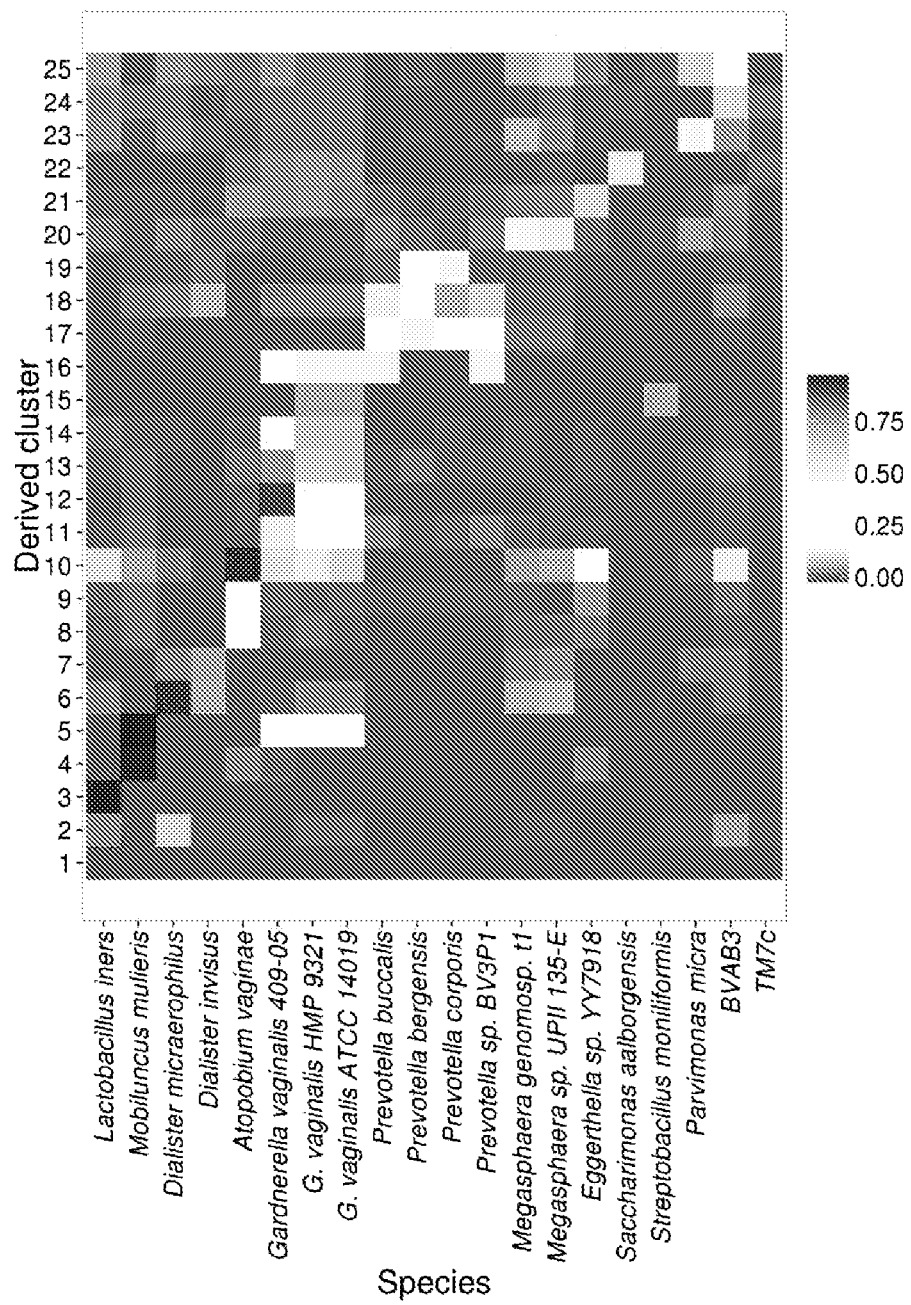

FIG. 37 shows the alignment of draft contigs in the MetaPhase clusters to the reference genomes of many species suspected to be in the sample according to some embodiments.

Figure 38:

FIG. 38 is a table showing metrics for the LACHESIS scaffolding results on de novo assemblies according to some embodiments. The human and mouse de novo assemblies were created by assembling short-insert and ~2.5 Kb jumping libraries with the ALLPATHS-LG assembler (Gnerre et al. 2011). In the human and mouse assemblies, the input contigs are scaffolds; the N50 reported is ungapped. The *Drosophila* shotgun assembly is made up of contigs created from a single short-read library sequenced by the *Drosophila* Genetic Reference Panel (DGRP). LACHESIS places scaffolds or contigs into groups and then orders and orients them within each group. An ordering error means that a contig or scaffold's position is out of the expected order with respect to its neighbors. An orientation error means that its orientation is not the orientation implied by its position with respect to its immediate predecessor. "High-quality prediction" refers to a subset of contigs or scaffolds whose position and orientation in their ordering is deemed more certain; the threshold for high quality is chosen for convenience for each assembly.

Figure 39:
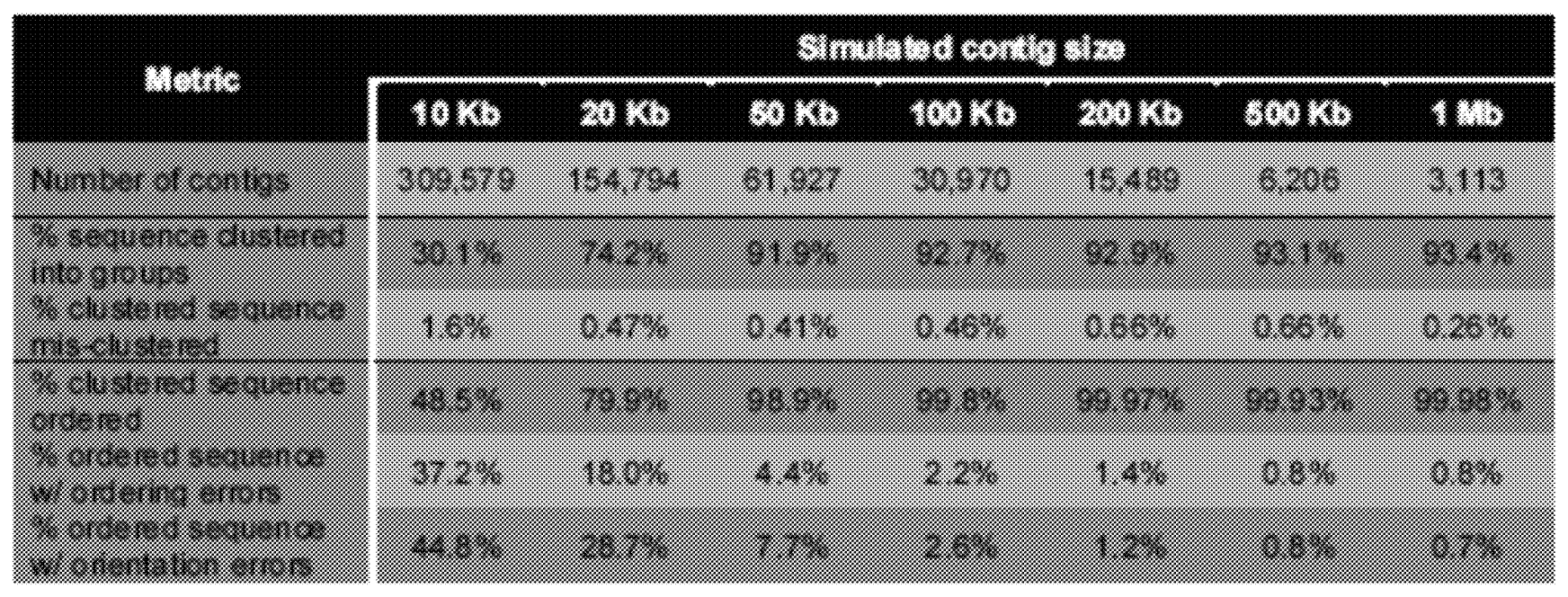

FIG. 39 is a table showing metrics for the LACHESIS scaffolding results on simulated assemblies according to some embodiments. Simulated assemblies were created by breaking up the human reference genome into simulated contigs of varying sizes, and then using LACHESIS to cluster, order, and orient the simulated contigs. The simulated contigs' expected order and orientation are derived from their true position in the reference genome. Ordering and orientation errors are defined as in FIG. 38.

FIG. 40 is a table showing metrics for the LACHESIS scaffolding results according to some embodiments. This is a more detailed version of FIG. 38. Results for the human de novo assembly exclude the chimeric group not shown in FIG. 7.

FIG. 41 is a table showing contents of LACHESIS' orderings in the human de novo assembly (FIG. 7) according to some embodiments. For each of the 23 groups, there is a "dominant chromosome" in the reference genome to which the plurality of alignable sequence aligns. This chart shows what fraction of the scaffold length in each ordering aligns to the dominant chromosome, to other chromosomes, or to no chromosomes. The last row corresponds to the small, chimeric chromosome group described in the main text.

FIG. 42 is a table showing enrichment of repetitive sequences in error-prone regions according to some embodiments. Human genomic regions corresponding to several different types of repetitive sequence elements were downloaded from the UCSC Genome Browser (genome.ucsc.edu). For each scaffold in the human de novo assembly created by LACHESIS, a 5-Kb region was extracted around each of its ends. These edge regions were then overlapped with the repeat elements. The enrichment shown for each type of repeat element is the ratio of the frequency with which that element co-occurs with the ends of one of the 61 scaffolds marked with ordering errors, divided by the frequency with which it co-occurs with the ends of one of the 7,604 scaffolds not marked with ordering errors.

FIG. 43 is a table showing contents of LACHESIS' orderings in the mouse de novo assembly (FIG. 11) according to some embodiments. For each of the 20 groups, there is a "dominant chromosome" in the reference genome to which the majority of alignable sequence aligns. This chart shows what fraction of the scaffold length in each ordering aligns to the dominant chromosome, to other chromosomes, or to no chromosomes.

FIG. 44 is a table showing contents of LACHESIS' orderings in the D. melanogaster de novo assembly (FIG. 13) according to some embodiments. For each of the four groups, there is a "dominant chromosome" in the reference genome to which the majority of euchromatic sequence aligns. This chart shows what fraction of the contig length in each ordering aligns to the dominant chromosome, to other chromosomes, or to no euchromatic chromosome. Note that a substantial fraction of the D. melanogaster assembly may include heterochromatic sequences as it does not align to the four euchromatic chromosomes of the reference assembly.

FIG. 45 is a table showing the effect of Hi-C downsampling on LACHESIS assembly quality according to some embodiments. LACHESIS was provided with varying quantities of Hi-C read coverage with which to scaffold the shotgun human assembly. As read coverage increased, the total amount of sequence placed by LACHESIS increased slightly, while error rates decreased significantly. The bottom row describes the same assembly as in FIGS. 6a, 6b and FIG. 41.

FIG. 46 is a table showing the M-Y species list and abundancies in a sample according to some embodiments.

FIG. 47 is a table showing the M-3D species list and abundancies in a sample according to some embodiments.

FIG. 48 is a table showing clustering results on bootstrapped Hi-C link datasets according to some embodiments. The MetaPhase clustering algorithm was run on the M-Y and M-PE datasets, producing the results given in Example 3 below. The clustering algorithm was also re-run in each of these cases and randomized bootstrapping (re-sampling with replacement of N data points) to the Hi-C link data was applied. Shown are the results of eight bootstrapping runs for each sample.

DETAILED DESCRIPTION

Computational methods and systems for large scale scaffolding of genomes are provided herein. Next-generation de novo assemblies are highly fragmented relative to the finished chromosomes of H. sapiens and key model organisms generated by the Human Genome Project. To cost-effectively generate high-quality de novo assemblies, scalable, broadly accessible methods enabling chromosome-scale contiguity are needed. As illustrated in the Examples below, genome-wide chromatin interaction datasets such as those generated by chromosome conformation analysis techniques (like Hi-C) are shown to be a novel and rich source of long-range information for assigning, ordering, and orienting genomic sequences to chromosomes, including across centromeres. To exploit this novel use of data generated by chromosome conformation analysis techniques (e.g., Hi-C), the methods referred to herein as LACHESIS (Ligating Adjacent CHromatin Enables Scaffolding In Situ) were developed for ultra-long-range scaffolding of de novo genome assemblies. The effectiveness of this approach is demonstrated by combining shotgun fragment and short jump mate-pair sequences with data generated by chromosome conformation analysis techniques (e.g., Hi-C) to generate chromosome-scale de novo assemblies of the human, mouse and Drosophila genomes, achieving as high as 98% accuracy in assigning scaffolds to chromosome groups (human) and 99% accuracy in ordering and orienting scaffolds within chromosome groups. Chromosome conformation analysis data may also be used to validate chromosomal translocations in cancer genomes.

Scaffolding of Genome Assemblies

According to some embodiments, the computational methods described herein may include a step of applying a location clustering model to a test set of contigs to form two or more location cluster groups, each of which includes one or more location-clustered contigs. In some aspects, the test set of contigs used in the methods described herein may be generated by aligning a set of reads from a genome, chromosome or other genetic molecule or molecules of interest with a draft assembly, a reference assembly, or both a draft assembly and a reference assembly. The genome, chromosome or other genetic molecule or molecules of interest may be from any species of interest, including, but not limited to, humans and other mammals, and any vertebrate, invertebrate, eukaryote, or prokaryote.

In some aspects, the set of reads may form part of an input file used by a system to carry out the methods described herein. The set of reads may be generated by any suitable method based on chromatin interaction techniques or chromosome conformation analysis techniques. Chromosome conformation analysis techniques that may be used in accordance with the embodiments described herein may include, but are not limited to, Chromatin Conformation Capture (3C), Circularized Chromatin Conformation Capture (4C), Carbon Copy Chromosome Conformation Capture (5C), Chromatin Immunoprecipitation (ChIP; e.g., cross-linked ChIP (XChIP), native ChIP (NChIP)), ChIP-Loop, genome conformation capture (GCC) (e.g., Hi-C, 6C), Capture-C. In some embodiments, the dataset is generated using a genome-wide chromatin interaction method, such as Hi-C.

According to some embodiments, a draft assembly to which the set of reads is aligned may be a de novo assembly that is assembled using any suitable sequence assembler known in the art including, but not limited to, ABySS, ALLPATHS-LG, AMOS, Arapan-M, Arapan-S, Celera WGA Assembler/CABOG, CLC Genomics Workbench & CLC Assembly Cell, Cortex, DNA Baser, DNA Dragon, DNAnexus, Edena, Euler, Euler-sr, Forge, Geneious, Graph Constructor, IDBA, IDBA-UD, LIGR Assembler, MaSuRCA, MIRA, NextGENe, Newbler, PADENA, PASHA, Phrap, TIGR Assembler, Ray, Sequecher, SeqMan NGen, SGA, SGARCGS, SOPRA, SparseAssembler, SSAKE, SOAPdenovo, SPAdes, Staden gap4 package, Taipan, VCAKE, Phusion assembler, QSRA, and Velvet.

The set of reads may be aligned with the draft assembly, reference assembly, or both, by any suitable alignment method, algorithm or software package known in the art. Suitable short read sequence alignment software that may be used to align the set of reads with an assembly include, but are not limited to, BarraCUDA, BBMap, BFAST, BLASTN, BLAT, Bowtie, HIVE-hexagon, BWA, BWA-PSSM, CASHX, Cloudburst, CUDA-EC, CUSHAW, CUSHAW2, CUSHAW2-GPU, CUSHAW3, drFAST, ELAND, ERNE, GASSST, GEM, Genalice MAP, Geneious Assembler, GensearchNGS, GMAP and GSNAP, GNUMAP, iSAAC, LAST, MAQ, mrFAST and mrsFAST, MOM, MOSAIK, Novoalign & NovoalignCS, NextGENe, NextGenMap, Omixon, PALMapper, Partek, PASS, PerM, PRIMEX, QPalma, RazerS, REAL, cREAL, RMAP, rNA, RTG Investigator, Segemehl, SeqMap, Shrec, SHRiMP, SLIDER, SOAP, SOAP2, SOAP3, SOAP3-dp, SOCS, SSAHA, SSAHA2, Stampy, SToRM, subread and Subjunc, Taipan, UGENE, VelociMapper, XpressAlign, and Zoom.

The two or more location cluster groups formed by applying the location clustering model to the test set of contigs may be associated with any physical location of the genome, chromosome or other genetic molecule of interest. For example, the two or more location cluster groups may be chromosome groups, wherein each group includes one or more contigs derived from or located on the same chromosome. Thus, in certain aspects, the number of location cluster groups is designed to correspond to the number of chromosomes in the sample genome of interest. (e.g., 23 X chromosomes and 23 Y chromosomes for human, examples of other species are shown below and are known in the art). In some cases, the number of location cluster groups is predetermined based on known number of chromosomes in a sample species' genome of interest.

In some embodiments, the location clustering model includes a step of building a graph. As referred to herein, the term "graph" refers to a graph that is an ordered pair G=(V, E) that includes a set of vertices or nodes (V) together with a set of edges or lines (E), which are 2-element subsets of V (e.g., an edge is related with two vertices, and re relation is represented as an unordered pair of the vertices with respect to the particular edge) (e.g., undirected or simple graph). Alternatively, E may be a set together with a relation of incidence that associates with each edge two vertices; or E may be a multiset of unordered pairs of vertices which are not necessarily distinct (e.g., a multigraph or pseudograph). In certain embodiments, each node is represented by a single contig of the test set of contigs, and each edge between nodes has a weight equal to the number of read-pairs (e.g., Hi-C read pairs) linking the two contigs.

In certain embodiments, the location clustering model includes a step of applying a clustering algorithm. Clustering algorithms that may be used in accordance with the embodiments described herein include, but are not limited to, connectivity model algorithms (e.g., hierarchical clustering models), centroid model algorithms (e.g., k-means algorithm), distribution model algorithms (e.g., multivariate normal distributions), density model algorithms (e.g., DBSCAN and OPTICS), subspace model algorithms (e.g., biclustering, co-clustering, two-mode-clustering), group model algorithms, graph-based model algorithms (e.g., a clique). In certain embodiments, the clustering algorithm is a connectivity based clustering algorithm, also known as a hierarchical clustering algorithm or a hierarchical agglomerative clustering algorithm. This algorithm connects "objects" to form "clusters" based on their distance. Each cluster can be described largely by the maximum distance needed to connect parts of the cluster. At different distances, different clusters will form, which can be represented using a dendrogram, which explains where the common name "hierarchical clustering" comes from: these algorithms do not provide a single partitioning of the data set, but instead provide an extensive hierarchy of clusters that merge with each other at certain distances. In a dendrogram, the y-axis marks the distance at which the clusters merge, while the objects are placed along the x-axis such that the clusters don't mix.

Connectivity based clustering is a whole family of methods that differ by the way distances are computed. Apart from the usual choice of distance functions, a user also needs to decide on the linkage criterion or metric (since a cluster is made up of multiple objects, there are multiple candidates to compute the distance to) to use. In some aspects, the linkage metric may be, but is not limited to, single-linkage clustering (the minimum of object distances), complete linkage clustering (the maximum of object distances) or UPGMA ("Unweighted Pair Group Method with Arithmetic Mean", also known as average linkage clustering). Furthermore, hierarchical clustering can be agglomerative (starting with single elements and aggregating them into clusters) or divisive (starting with the complete data set and dividing it into partitions). According to some embodiments, the location clustering algorithm is a hierarchical agglomerative clustering algorithm. In certain aspects, the hierarchical agglomerative clustering algorithm is applied with an average-linkage metric to calculate the link density between each contig of the test set (see Example 1 below).

According to some embodiments, the methods described herein may also include a step of applying an ordering model to each of the two or more location cluster groups to form an ordered set of one or more location-clustered contigs within each location cluster group. In some embodiments, the ordering model includes a step of building a graph. In certain aspects, the graph is built with vertices representing contigs and edge weights corresponding to the inverse of the normalized linkage density between pairs of contigs.

In certain embodiments, the ordering model includes a step of calculating a minimum spanning tree. Given a connected graph such as that built in the step above, a spanning tree of that graph is a subgraph that is a tree that connects all the vertices together. A single graph can have many different spanning trees. A weight may be assigned to each edge, which is a number representing how unfavorable it is. This weight may be used to assign a weight to a spanning tree by computing the sum of the weights of the edges in that spanning tree. A minimum spanning tree (MST) or minimum weight spanning tree is then a spanning tree with weight less than or equal to the weight of every other spanning tree. To find or calculate a minimum spanning tree, any suitable algorithm may be applied including, but not limited to, greedy algorithms (e.g., Boruvka's algorithm, Prim's algorithm, reverse-delete algorithm, and Kruskal's algorithm), deterministic algorithms, parallel algorithms, or other specialized algorithms designed for computing minimum spanning trees of a graph. Some of these algorithms are so large that most of it must be stored on a computer-readable storage medium at all times.

According to some embodiments, the methods described herein may also include a step of applying an orienting model to each ordered set of one or more location-clustered contigs to assign a relative orientation to each of the location-clustered contigs within each location cluster group. In some embodiments, the orienting model includes a step of building a graph. In certain aspects, the graph is a weighted directed acyclic graph (WDAG).

In certain embodiments, the orienting model includes a step of calculating an orientation quality score for each location-clustered contig. In some aspects, the orientation quality score is calculated as follows: the log-likelihood of the observed set of chromatin interaction links (e.g., Hi-C links) between one contig (in its current orientation), and its neighbors is found; then the contig was flipped and the log-likelihood was calculated again. The difference between the log-likelihoods is taken as the quality score.

Species-Level Deconvolution of Metagenome Assemblies

In certain embodiments, computational methods for separating or deconvoluting individual species from a sample that includes two or more species (i.e., a metagenome) are provided herein. Microbial communities are made up of mixed populations of organisms, including unknown species in unknown abundances. These communities are often studied through metagenomic shotgun sequencing, but standard library construction methods remove long-range contiguity information; thus shotgun sequencing and de novo assembly of a metagenome typically yields a collection of contigs that cannot readily be grouped by species. Methods for generating chromatin-level contact probability maps, e.g., as generated by the Hi-C method, provide a signal of contiguity that is completely intracellular and contains both intra- and interchromosomal information. As shown in the Examples below, it is demonstrated how this signal can be exploited to reconstruct the individual genomes of microbial species present within a mixed sample. This approach was applied to two synthetic metagenome samples, successfully clustering the genome content of fungal, bacterial, and archaeal species with over 99% agreement with published reference genomes. Further, it was shown that the Hi-C signal can secondarily be used to create scaffolded genome assemblies of individual eukaryotic species present within the microbial community, with higher levels of contiguity than some of the species' published reference genomes.

Such methods (which may be referred to herein as "MetaPhase") may include a step of applying a species clustering model to a heterogeneous set of contigs to form two or more species cluster groups, each of which includes one or more species-clustered contigs from a single species. In some aspects, the heterogeneous set of contigs used in the methods described herein may be generated by aligning a set of reads from a heterogeneous species mixture with a draft metagenome assembly, a set of reference species genome assemblies, or both.

In some aspects, the set of reads may form part of an input file used by a system to carry out the methods described herein. The set of reads may be generated by any suitable method based on chromatin interaction techniques or chromosome conformation analysis techniques. Chromosome conformation analysis techniques that may be used in accordance with the embodiments described herein may include, but are not limited to, Chromatin Conformation Capture (3C), Circularized Chromatin Conformation Capture (4C), Carbon Copy Chromosome Conformation Capture (5C), Chromatin Immunoprecipitation (ChIP; e.g., cross-linked ChIP (XChIP), native ChIP (NChIP)), ChIP-Loop, genome conformation capture (GCC) (e.g., Hi-C, 6C), Capture-C. In some embodiments, the dataset is generated using a genome-wide chromatin interaction method, such as Hi-C.

According to some embodiments, a draft metagenome assembly to which the set of reads is aligned may be a de novo assembly that is assembled using any suitable sequence assembler known in the art including, but not limited to, ABySS, ALLPATHS-LG, AMOS, Arapan-M, Arapan-S, Celera WGA Assembler/CABOG, CLC Genomics Workbench & CLC Assembly Cell, Cortex, DNA Baser, DNA Dragon, DNAnexus, Edena, Euler, Euler-sr, Forge, Geneious, Graph Constructor, IDBA, IDBA-UD, LIGR Assembler, MaSuRCA, MIRA, NextGENe, Newbler, PADENA, PASHA, Phrap, TIGR Assembler, Ray, Sequecher, SeqMan NGen, SGA, SGARCGS, SOPRA, SparseAssembler, SSAKE, SOAPdenovo, SPAdes, Staden gap4 package, Taipan, VCAKE, Phusion assembler, QSRA, and Velvet.

The set of reads may be aligned with the draft metagenome assembly, the set of reference species genome assemblies, or both, by any suitable alignment method, algorithm or software package known in the art. Suitable short read sequence alignment software that may be used to align the set of reads with an assembly include, but are not limited to, BarraCUDA, BBMap, BFAST, BLASTN, BLAT, Bowtie, HIVE-hexagon, BWA, BWA-PSSM, CASHX, Cloudburst, CUDA-EC, CUSHAW, CUSHAW2, CUSHAW2-GPU, CUSHAW3, drFAST, ELAND, ERNE, GASSST, GEM, Genalice MAP, Geneious Assembler, GensearchNGS, GMAP and GSNAP, GNUMAP, IDBA-UD, iSAAC, LAST, MAQ, mrFAST and mrsFAST, MOM, MOSAIK, Novoalign & NovoalignCS, NextGENe, NextGenMap, Omixon, PALMapper, Partek, PASS, PerM, PRIMEX, QPalma, RazerS, REAL, cREAL, RMAP, rNA, RTG Investigator, Segemehl, SeqMap, Shrec, SHRiMP, SLIDER, SOAP, SOAP2, SOAP3, SOAP3-dp, SOCS, SSAHA, SSAHA2, Stampy, SToRM, subread and Subjunc, Taipan, UGENE, VelociMapper, XpressAlign, and Zoom.

The two or more species cluster groups formed by applying the location clustering model to the test set of contigs may be associated with each species that is or is suspected of being in a heterogeneous sample that includes 2 or more species.

In some embodiments, the location clustering model includes a step of building a graph. In certain embodiments, each node of the graph is represented by a single contig of the heterogeneous set of contigs, and each edge between nodes has a weight equal to the number of read-pairs (e.g., Hi-C read pairs) linking the two contigs, normalized by the number of restriction sites on the contigs.

In certain embodiments, the location clustering model includes a step of applying a clustering algorithm. Clustering algorithms that may be used in accordance with the embodiments described herein include, but are not limited to, connectivity model algorithms (e.g., hierarchical clustering models), centroid model algorithms (e.g., k-means algorithm), distribution model algorithms (e.g., multivariate normal distributions), density model algorithms (e.g., DBSCAN and OPTICS), subspace model algorithms (e.g., biclustering, co-clustering, two-mode-clustering), group model algorithms, graph-based model algorithms (e.g., a clique). In certain embodiments, the clustering algorithm is a hybrid clustering algorithm, wherein the hybrid clustering algorithm includes (1) application of the Jarvis-Patric nearest-neighbor clustering algorithm with k=100, removing some edges and reweighting all other edge weights by the frequency of their nodes' shared nearest neighbors; and (2) application of a hierarchical agglomerative clustering algorithm with an average-linkage metric. The application of the location clustering model results in separation of genetic material from each species present in a sample into a set of species-clustered contigs. The species-clustered contigs from a particular species may then be used as a test set of contigs in the scaffolding methods described above.

Computer Systems and Software

The methods described herein may be used in the context of a computer system or as part of software or computer-executable instructions that are stored in a computer-readable storage medium.

In some embodiments, a system (e.g., a computer system) may be used to implement certain features of some of the embodiments of the invention. For example, in certain embodiments, a system (e.g., a computer system) for large scale scaffolding of a genome assembly and/or for separating or deconvoluting individual species from a sample is provided. The scaffolding and deconvolution performed by the system may be used to establish long range and chromosome-scale contiguity in accordance with the features of the embodiments described above.

In certain embodiments, the system may include one or more memory and/or storage devices. The memory and storage devices may be one or more computer-readable storage media that may store computer-executable instructions that implement at least portions of the various embodiments of the invention. In one embodiment, the system may include a computer-readable storage medium which stores computer-executable instructions that include, but are not limited to, one or both of the following: (i) instructions for applying a location clustering model to a test set of contigs to form two or more location cluster groups, each location cluster group comprising one or more location-clustered contigs; (ii) instructions for applying an ordering model to each of the two or more location cluster groups to form an ordered set of one or more location-clustered contigs within each cluster group; and (iii) instructions for applying an orienting model to each ordered set of one or more location-clustered contigs to assign a relative orientation to each of the location-clustered contigs within each location cluster group. Such instructions may be carried out in accordance with the methods described in the embodiments above.

In certain embodiments, the system may include a processor configured to perform one or more steps including, but not limited to, (i) receiving a set of input files, and (ii) executing the computer-executable instructions stored in the computer-readable storage medium. The set of input files may include, but is not limited to, a file that includes a set of reads generated by a chromosome conformation analysis technique (e.g., Hi-C, described above); one or more files that include a draft assembly, a reference assembly, or both. The steps may be performed in accordance with the methods described in the embodiments above.

The computer system may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, wearable device, or any machine capable of executing a set of instructions, sequential or otherwise, that specify actions to be taken by that machine.

The computing system may include one or more central processing units ("processors"), memory, input/output devices, e.g. keyboard and pointing devices, touch devices, display devices, storage devices, e.g. disk drives, and network adapters, e.g. network interfaces, that are connected to an interconnect.

According to some aspects, the interconnect is an abstraction that represents any one or more separate physical buses, point-to-point connections, or both, connected by appropriate bridges, adapters, or controllers. The interconnect, therefore, may include, for example a system bus, a peripheral component interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also referred to as Firewire.

In addition, data structures and message structures may be stored or transmitted via a data transmission medium, e.g. a signal on a communications link. Various communications links may be used, e.g. the Internet, a local area network, a wide area network, or a point-to-point dial-up connection. Thus, computer readable media can include computer-readable storage media, e.g. non-transitory media, and computer-readable transmission media.

The instructions stored in memory can be implemented as software and/or firmware to program one or more processors to carry out the actions described above. In some embodiments of the invention, such software or firmware may be initially provided to the processing system by downloading it from a remote system through the computing system, e.g. via the network adapter.

The various embodiments of the invention introduced herein can be implemented by, for example, programmable circuitry, e.g. one or more microprocessors, programmed with software and/or firmware, entirely in special-purpose hardwired, i.e. non-programmable, circuitry, or in a combination of such forms. Special purpose hardwired circuitry may be in the form of, for example, one or more ASICs, PLDs, FPGAs, etc.

Some portions of the detailed description may be presented in terms of algorithms, which may be symbolic representations of operations on data bits within a computer memory. These algorithmic descriptions and representations are those methods used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage)

media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Chromosome-Scale Scaffolding of De Novo Genome Assemblies Based on Chromatin Interactions Chromosome-scale scaffolding of de novo genome assemblies based on chromatin interactions. Hi-C and related protocols that generate chromosome conformation information use proximity ligation and massively parallel sequencing to probe the three-dimensional architecture of chromosomes within the nucleus, with interacting regions captured to paired-end reads (Lieberman-Aiden et al. 2009; Duan et al. 2010). In the resulting datasets, the probability of intrachromosomal contacts is on average much higher than that of interchromosomal contacts, as expected if chromosomes occupy distinct territories. Moreover, although the probability of interaction decays rapidly with linear distance, even loci separated by >200 Mb on the same chromosome are more likely to interact than loci on different chromosomes (Lieberman-Aiden et al. 2009). These types of chromatin interaction datasets have not previously been used to provide long range information for scaffolding de novo assemblies.

Figure 1:
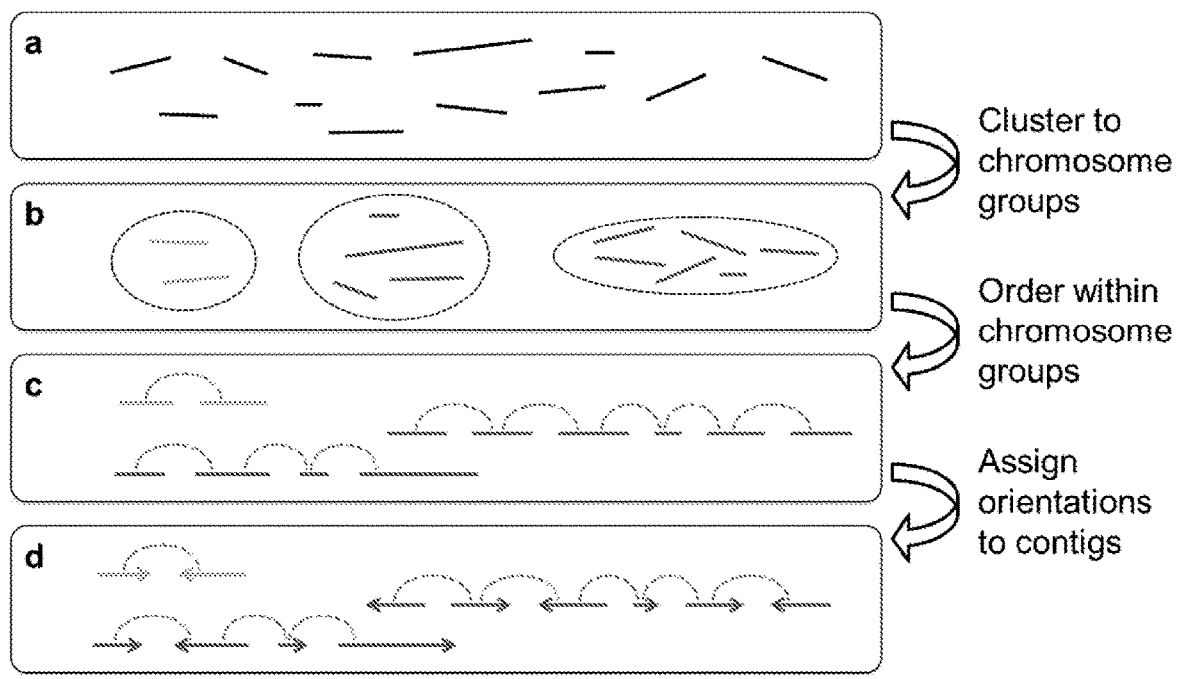
FIG. 1 is a schematic of the LACHESIS scaffolding method according to some embodiments.

Therefore, genome-wide chromatin interaction datasets such as those generated by Hi-C were used in the examples below to provide long-range information about the grouping and linear organization of sequences along entire chromosomes. These datasets were subjected to a new computational method, which exploits the signal of genomic proximity in Hi-C datasets for ultralong-range scaffolding of de novo genome assemblies. This method is referred to herein as LACHESIS (Ligating Adjacent CHromatin Enables Scaffolding In Situ). LACHESIS works in three steps, as illustrated in FIG. 1. First, clustering contigs or scaffolds to chromosome groups; second, ordering contigs or scaffolds within each chromosome group; and finally, assigning relative orientations to individual contigs or scaffolds. The effectiveness of this approach is demonstrated by combining shotgun fragment and short insert mate-pair (<3 Kb) sequences with Hi-C data to generate reasonably accurate chromosome-scale assemblies of the *H. sapiens, M. musculus,* and *D. melanogaster* genomes. It is also shown that Hi-C data can be used to validate chromosomal rearrangements in cancer genomes.

Materials and Methods

Input Datasets.

The procedure of Hi-C is outlined in Lieberman-Aiden et al. (2009) (Lieberman-Aiden et al. 2009, the subject matter of which is hereby incorporated by reference). Briefly, DNA in a nucleus is crosslinked, then cut with a restriction enzyme, leaving pairs of distally located but physically associated DNA molecules attached to one another. The sticky ends of these fragments are biotinylated and then ligated to each other to form chimeric circles. Biotinylated circles are enriched for, sheared again, and then processed to sequencing libraries in which individual templates are chimeras of the physically associated DNA molecules from the original cross-linking.

Four Hi-C datasets were used, corresponding to human cells, mouse cells, *Drosophila melanogaster* tissue, and HeLa cells. The human dataset was produced from human embryonic stem cells (hESCs) (Dixon et al. 2012). The hESC replicates 1 and 2 were used (NCBI SRA accessions: GSM862723, GSM892306) for a total of 734 M read-pairs. The mouse dataset was produced from mouse embryonic stem cells (mESCs) (Dixon et al. 2012). The mESC replicates 1 and 2 were used (NCBI SRA accessions: GSM862720, GSM862721) for a total of 806 M read-pairs. The *D. melanogaster* dataset was produced from embryos (Sexton et al. 2012) and includes 363 M read-pairs (NCBI SRA accession: SRX111555). The HeLa Hi-C dataset was produced as part of this study (see "Chromosome Fusion Detection in HeLa", below) and includes 305 M read-pairs.

Two types of shotgun assemblies were created as inputs to LACHESIS. First, shotgun assemblies for human, mouse, and *Drosophila melanogaster* were created by downloading the appropriate sequence libraries from SRA and assembling them with ALLPATHS-LG. FIG. 38 shows statistics for these three assemblies. Second, simulated shotgun assemblies were made by breaking up the human reference assembly into contigs of varying sizes, ranging from 10 Kb to 1 Mb. FIG. 39 shows statistics for these assemblies.

Shotgun Assemblies.

To create the human shotgun assembly, the sequence files corresponding to the fragment library and two short jumping libraries for individual NA12878 specified in Gnerre et al. 2011 (the subject matter of which is hereby incorporated by reference) were downloaded from the NCBI Short Read Archive (NCBI SRA accession SRA024407). The files were converted from sra to fastq format, and formatted as required by the ALLPATHS-LG assembler using the PrepareAllPathsInputs.pl script included with the ALLPATHS-LG distribution. The reads were assembled using the ALLPATHS-LG assembler (Gnerre et al. 2011) (version r41985) with the following parameters (the rest being default): HAPLOIDIFY=TRUE, MAX_MEMORY_GB=400, THREADS=32, EVALUATION=STANDARD. Insert size estimates (mean and standard deviation) for each library were specified based on the values provided in Gnerre et al. Scaffolds in this assembly were treated as contigs by LACHESIS. Because fosmid end sequencing data was intentionally excluded, this assembly had far less mid-range contiguity than the full de novo assembly produced in Gnerre et al. (N50 scaffold length 437 Kb vs. 11.5 Mb) and thus it more closely represents a more typical de novo assembly created exclusively from in vitro libraries.

To create the mouse shotgun assembly, the sequence files corresponding to the fragment and three short jumping libraries specified in Gnerre et al. 2011 (the subject matter of which is hereby incorporated by reference) were downloaded from the NCBI Short Read Archive (NCBI SRA accession SRA009956). The libraries were assembled using the ALLPATHS-LG assembler (Gnerre et al. 2011) (version r41985) with the following parameters (the rest being default): HAPLOIDIFY=TRUE, MAX_MEMORY_GB=500, THREADS=32. Insert size estimates (mean and standard deviation) for each library were specified based on the values provided in Gnerre et al.

To create the *Drosophila melanogaster* shotgun assembly, the sequence files for *D. melanogaster* (*Drosophila* Genomic Reference Panel (Mackay et al. 2012, the subject matter of which is hereby incorporated by reference) corresponding to sequencing runs SRR516038 (Sample DGRP-348) and SRR516001 (Sample DGRP-821) were downloaded from the NCBI Short Read Archive. SRR516038 served as the "fragment" library as per ALLPATHS-LG terminology. The ALLPATHS-LG assembler also requires a "jumping" library. A jumping library for *D. melanogaster* that was previously sequenced was not found. Instead, a standard shotgun library with a slightly higher insert size (SRR516001) was used and artificially converted it into a jumping library by flipping the orientation of reads. All files were first converted from sra to fastq format, then formatted as required by the ALLPATHS-LG assembler using the PrepareAllPathsInputs.pl script included with the ALLPATHS-LG distribution. Insert size distributions for these libraries (mean=205 bp, standard deviation=25 bp for fragment library; mean=320 bp, standard deviation=52 bp for jumping library) were obtained by aligning a subset of reads to the *D. melanogaster* reference genome using BWA (Li & Durbin 2010, the subject matter of which is hereby incorporated by reference). The reads were assembled using the ALLPATHS-LG assembler6 (version r41985) with the following parameters (the rest being default): HAPLOIDIFY=TRUE, MAX_MEMORY_GB=300, THREADS=16, VAPI_WARN_ONLY=True.

Aligning Hi-C Reads.

Hi-C reads were aligned to shotgun assemblies or reference genomes using BWA (Li & Durbin 2010, the subject matter of which is hereby incorporated by reference) with default parameters. Reads were considered artifactual if they did not align within 500 bp of a restriction site (Yaffe & Tanay 2011). Non-uniquely aligning reads were assigned a mapping quality of 0 by BWA and were excluded from subsequent analysis. Additionally, read-pairs were considered for downstream analysis only if both reads in the pair aligned to contigs from the assembly.

Clustering Contigs or Scaffolds into Chromosome Groups.

Figure 2:
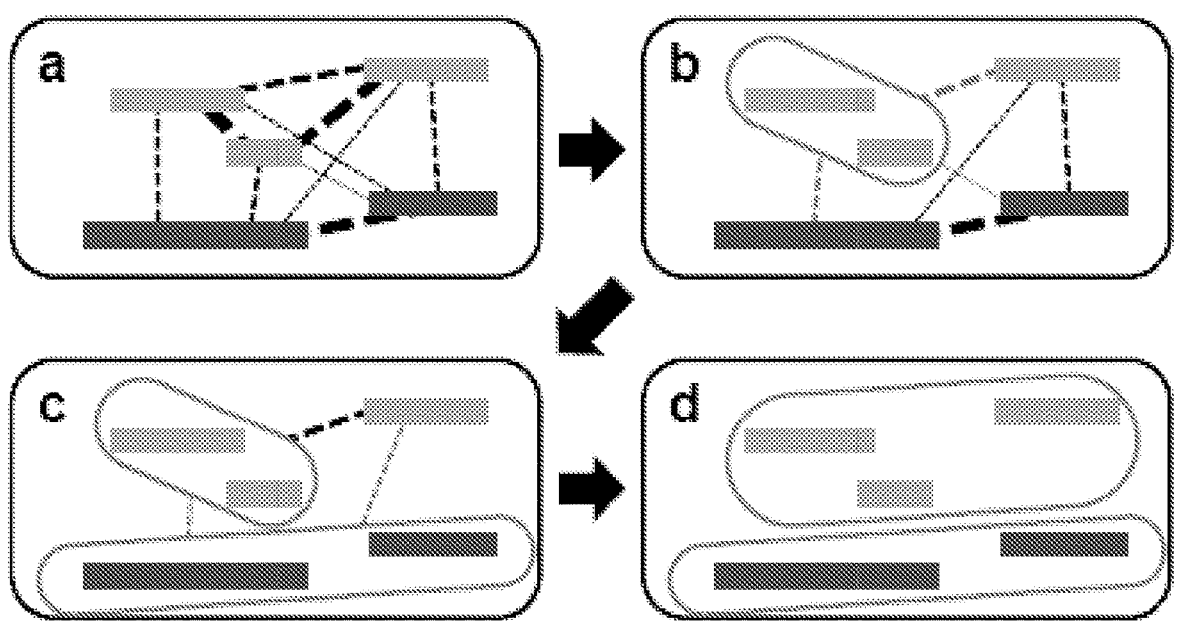
FIG. 2 is an illustrated overview of the LACHESIS clustering algorithm according to some embodiments.

Contigs or scaffolds (the term 'contig' is used in this description of the method to indicate both possibilities) were placed into groups using hierarchical clustering (FIG. 2). A graph was built, with each node initially representing one contig, and each edge between nodes having a weight equal to the number of Hi-C read-pairs linking the two contigs. The contigs were merged together using hierarchical agglomerative clustering with an average-linkage metric (Eisen et al. 1998, the subject matter of which is hereby incorporated by reference), which was applied until the number of groups was reduced to the expected number of distinct chromosomes (counting only groups with more than one contig). Repetitive contigs (contigs whose average link density with other contigs, normalized by number of restriction fragment sites, was greater than 2 times average) and contigs with too few restriction fragment sites (<5 for the simulated human assembly; <25 for the human and mouse de novo assemblies; <250 for the *D. melanogaster* assembly) were not used during the agglomerative clustering. After clustering, each of these contigs was assigned to a group if its average link density with that group was greater than four times its average link densities with any other group.

Ordering Contigs or Scaffolds within Chromosome Groups.

Each group of contigs or scaffolds (the term 'contig' is used in this description of the method to indicate both possibilities) was ordered using the following algorithm (FIG. 3): First, a graph was built as in the clustering step, but with the edge weights between nodes equal to the inverse of the number of Hi-C links between the contigs, normalized by the number of restriction fragment sites per contig. Short contigs (<5 restriction fragment sites for the simulated human assemblies; <20 sites for the human and mouse de novo assemblies; <20 Kb for the *Drosophila* de novo assembly) were excluded from this graph. A minimum spanning tree was calculated for this graph. The longest path in this tree, the "trunk", was found. The spanning tree was then modified so as to lengthen the trunk by adding contigs adjacent to the trunk to the trunk, in ways that kept the total edge weight heuristically low.

After a lengthened trunk was found for each group, it was converted into a full ordering, as follows: The trunk was removed from the spanning tree, leaving a set of "branches" containing all contigs not in the trunk. These branches were reinserted into the trunk, the longest branches first, with the insertion sites chosen so as to maximize the number of links between adjacent contigs in the ordering. Short fragments (<5 restriction fragment sites for the simulated human assemblies; <20 sites for the human and mouse de novo assemblies; <40 Kb for the *Drosophila* de novo assembly) were not reinserted; as a result, many small contigs that were clustered were left out of the final LACHESIS assembly.

Orienting Contigs or Scaffolds.

Figure 4:
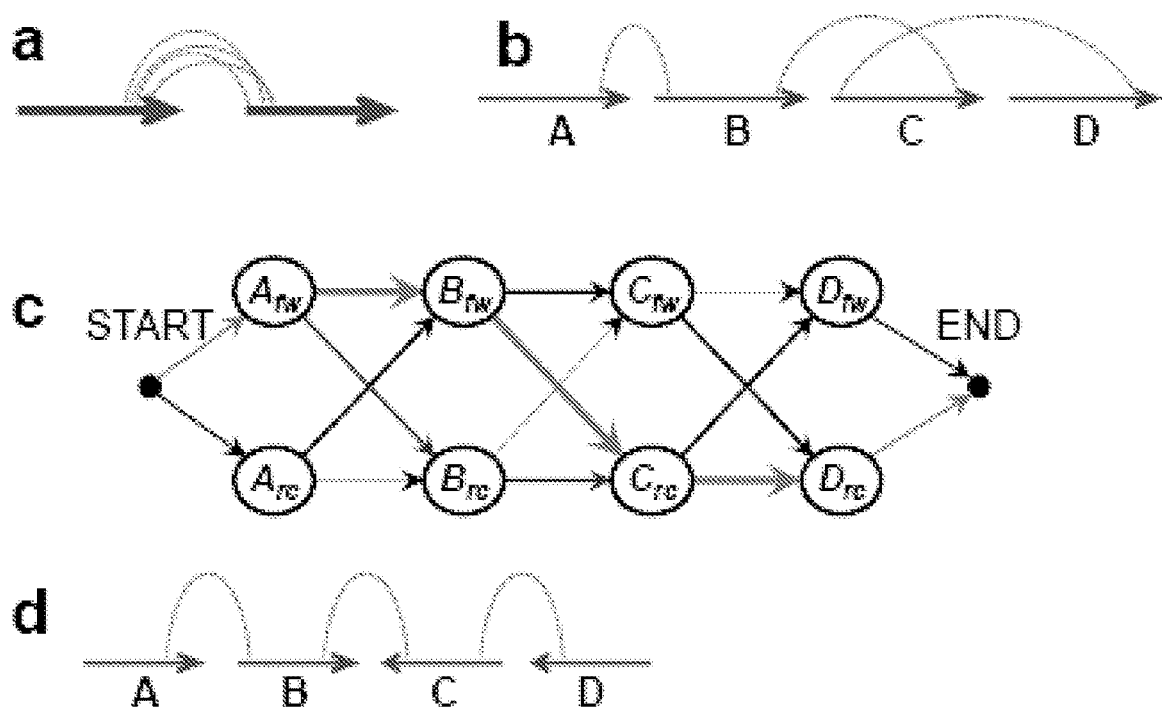
FIG. 4 is an illustrated overview of the LACHESIS orienting algorithm according to some embodiments.

The orientation of each contig or scaffold (the term 'contig' is used in this description of the method to indicate both possibilities) within its ordering was determined by taking into account the exact position of the Hi-C link alignments on each contig (FIG. 4). It was assumed that, as demonstrated in previous Hi-C studies (Lieberman-Aiden et al. 2009), the likelihood of a Hi-C link connecting two reads at a genomic distance of x is roughly $1/x$ for $x \geq \sim 100$ Kb. A weighted directed acyclic graph (WDAG) was built representing all possible ways to orient the contigs in the given order. Each edge in the WDAG corresponded to a pair of adjacent contigs in one of their four possible combined orientations, and the edge weight was set to the log-likelihood of observing the set of Hi-C link distances between the two contigs, assuming they were immediately adjacent with the given orientation.

For each contig, a quality score for its orientation was calculated as follows: The log-likelihood of the observed set of Hi-C links between this contig, in its current orientation, and its neighbors, was found. Then the contig was flipped and the log-likelihood was calculated again. The first log-likelihood was guaranteed to be higher because of how the orientations were calculated. The difference between the log-likelihoods was taken as a quality score.

Validation.

To determine the true position of the contigs or scaffolds in the shotgun assemblies, they were aligned to the human, mouse, or *D. melanogaster* reference genome using BLASTn32 with parameters '-perc_identity 99- evalue 100 -word_size 50'. For each contig, a "truth placement" on reference was derived as follows: First, the chromosome was chosen containing the plurality of aligned sequence from the contig. Second, the single best alignment to this chromosome (measured by E-value) was used to "seed" a chromosomal region. Third, the other alignments to this chromosome were considered by descending E-value, and the region was extended to include as many of them as possible without exceeding the total length of the assembly contig.

Chromosome Fusion Detection in HeLa.

A single, complex Hi-C library was constructed for the HeLa S3 cancer cell line (ATCC CCL2.2; grown in DMEM with 10% FBS and 1× Pen. Strep.) according to the protocol in van Berkum et al. (van Berkum et al. 2010, the subject matter of which is hereby incorporated by reference). The library was then sequenced on 2 lanes of Illumina HiSeq 2000, followed by read trimming to 50 bp to eliminate ligation-spanning reads that confound alignment. Reads were then aligned to the human reference genome using BWA (Li & Durbin 2010, the subject matter of which is hereby incorporated by reference) with default parameters, followed by removal of PCR duplicates. Reads were then assigned to genomic windows containing approximately one megabase of sequence (mean=955,176 bp) that were determined by bases of unique mappability to the genome. Links between windows were normalized first to the number of HindIII restriction sites present in the window to account for biases inherent to restriction based library preparation, then to the total count of short pairs within the window (defined as pairs with an insert size ≤1 Kb) to account for the underlying copy number of the window.

Rearrangements were called by first identifying stretches of ≥10 consecutive windows within a row where ≥80% of windows have a link score ≥1 standard deviation above the mean of the entire row. Stretches of windows present in columns were called using the same parameters. Windows present in outlier stretches for both rows and columns were defined as outlier windows. These windows were then clustered with all proximal windows ≤2 windows away and the outlier window count and density within the outer borders of the cluster determined. Outlier spans and clusters are shown in FIG. 5.

Results

The input to LACHESIS is a set of contigs or scaffolds (the term 'contig' is used in this description of the method to indicate both possibilities), such as are generated by de Bruijn graph-based de novo assemblers (Compeau et al. 2011; Gnerre et al. 2011), and a genome-wide chromatin interaction dataset, such as is generated by the Hi-C method (Lieberman-Aiden et al. 2009; Duan et al. 2010) (FIG. 1*a*). In a first step, LACHESIS uses hierarchical agglomerative clustering to group contigs that are likely to derive from the same chromosome, exploiting the fact that intrachromosomal contacts are on average more probable than interchromosomal contacts in Hi-C datasets (Lieberman-Aiden et al. 2009) (FIG. 1*b*; FIG. 2). An average-linkage metric (Eisen et al. 1998) is used for this clustering, with linkage defined as the normalized density of Hi-C read pairs linking any given pair of contigs. The final number of groups is pre-specified, ideally set to the expected number of chromosomes.

Figure 3:
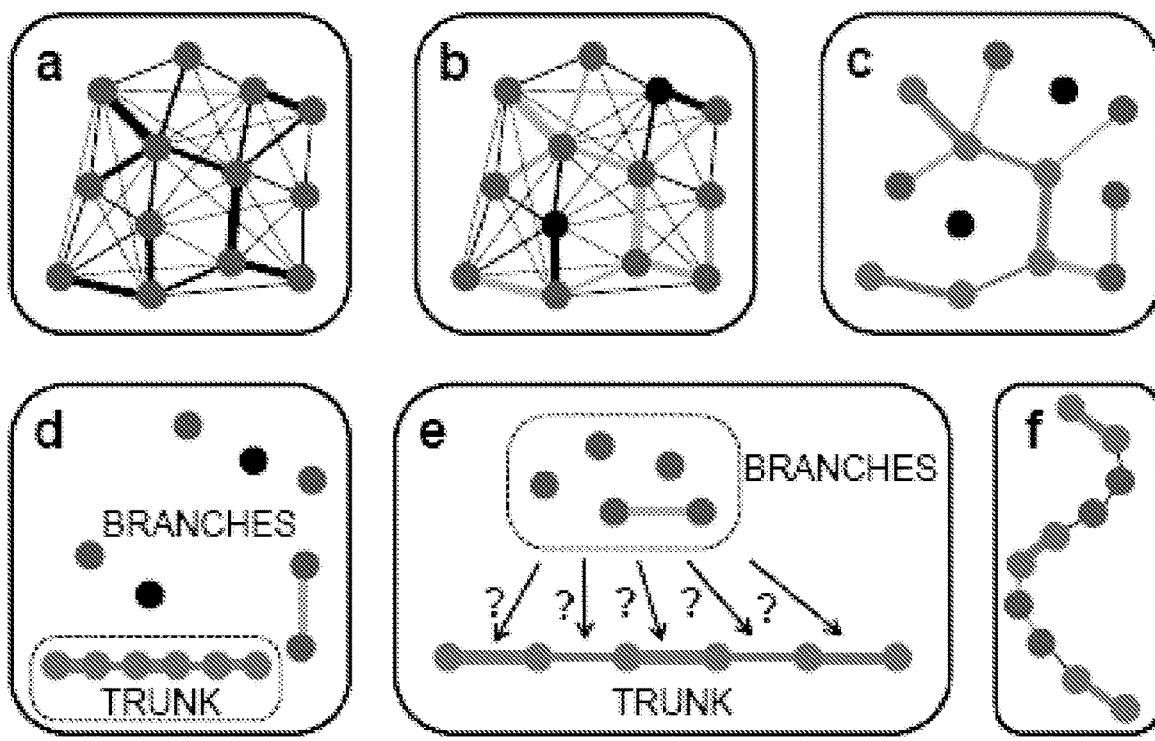
FIG. 3 is an illustrated overview of the LACHESIS ordering algorithm according to some embodiments.

In a second step, LACHESIS orders contigs linearly within each chromosome group by taking advantage of the higher Hi-C linkage densities expected between closely located contigs (FIG. 1*c*; FIG. 3). For each chromosome group, a graph is built with vertices representing contigs and edge weights corresponding to the inverse of the normalized Hi-C linkage density between pairs of contigs. A minimum spanning tree (MST) is found in this graph, and the longest path in the MST is extracted as the "trunk". To generate a full ordering, "branches" excluded from the trunk are reinserted into it at sites that maximize the amount of linkage between adjacent contigs.

In a third step, the ordered contigs are oriented with respect to one another by taking into account precisely where the Hi-C reads map on each contig (FIG. 1*d*; FIG. 4). For each chromosome group, a weighted directed acyclic graph (WDAG) is built representing all possible ways to orient the contigs, given the predicted order. The weights are calculated as the log-likelihood of the observed Hi-C links between adjacent contigs in a given combined orientation, assuming that the probability of a link connecting two reads at a genomic distance of x decays as $1/x$ for $x \geq \sim 100$ Kb (Lieberman-Aiden et al. 2009). The maximum likelihood path through this graph yields a predicted orientation for each contig.

Chromosome-scale de novo assembly of mammalian genomes. The effectiveness of this approach for the chromosome-scale de novo assembly of mammalian genomes was evaluated. Human and mouse were focused on as test cases because of the availability of the necessary datasets and the high quality of these reference genomes as gold standards for comparison. For human, ALLPATHS-LG was used to assemble only shotgun fragment and short jump (~2.5 Kb) mate-pair sequences (Gnerre et al. 2011) to an N50 scaffold length of 437 Kb and a total length of 2.74 Gb. This is referred to below as the "shotgun assembly". Fosmid end sequencing data was intentionally excluded because libraries of this type require cloning and are laborious to generate. Furthermore, as described below, the chromatin interaction data would effectively substitute for the ~40 Kb fosmid links while also providing even longer-range contiguity.

Figure 6:
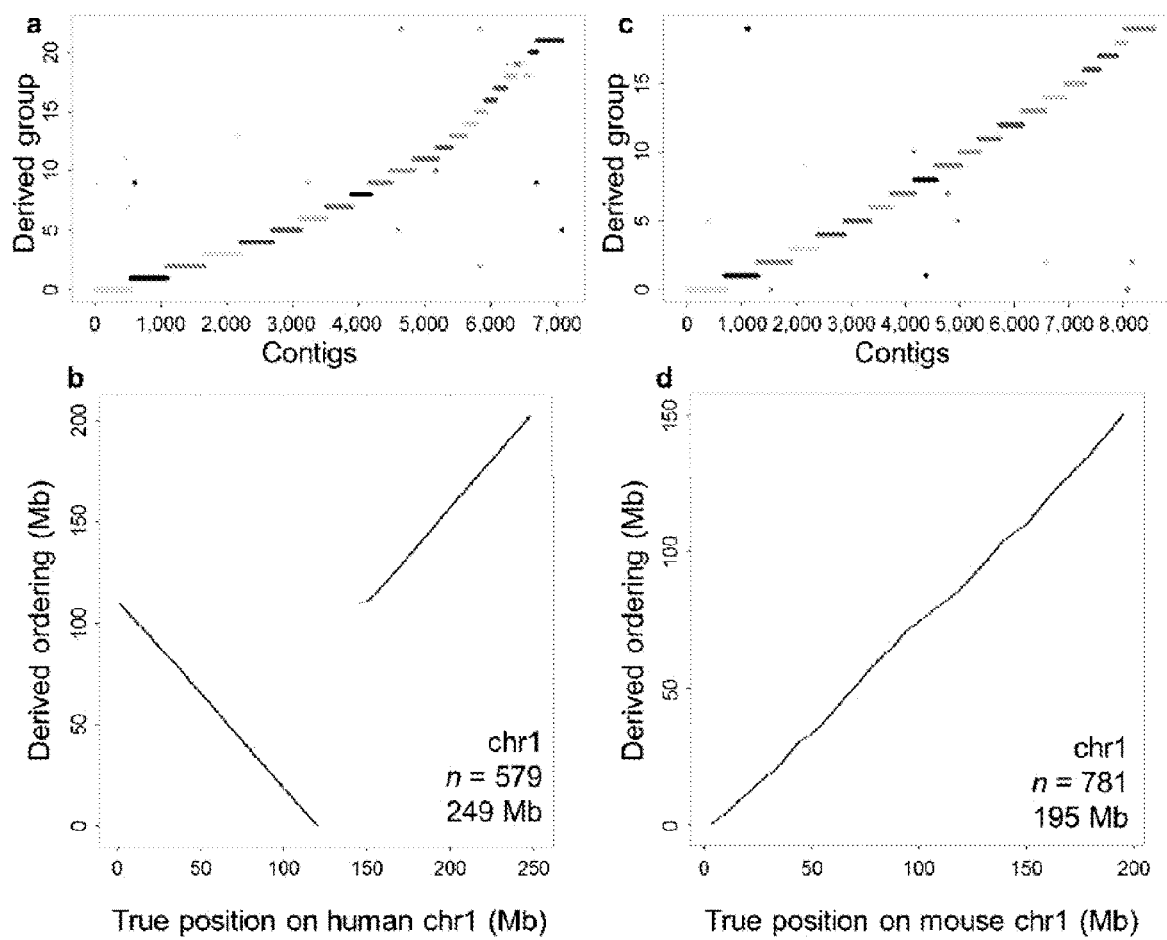
FIG. 6 shows clustering and ordering mammalian sequences with LACHESIS according to some embodiments.
Figure 7:
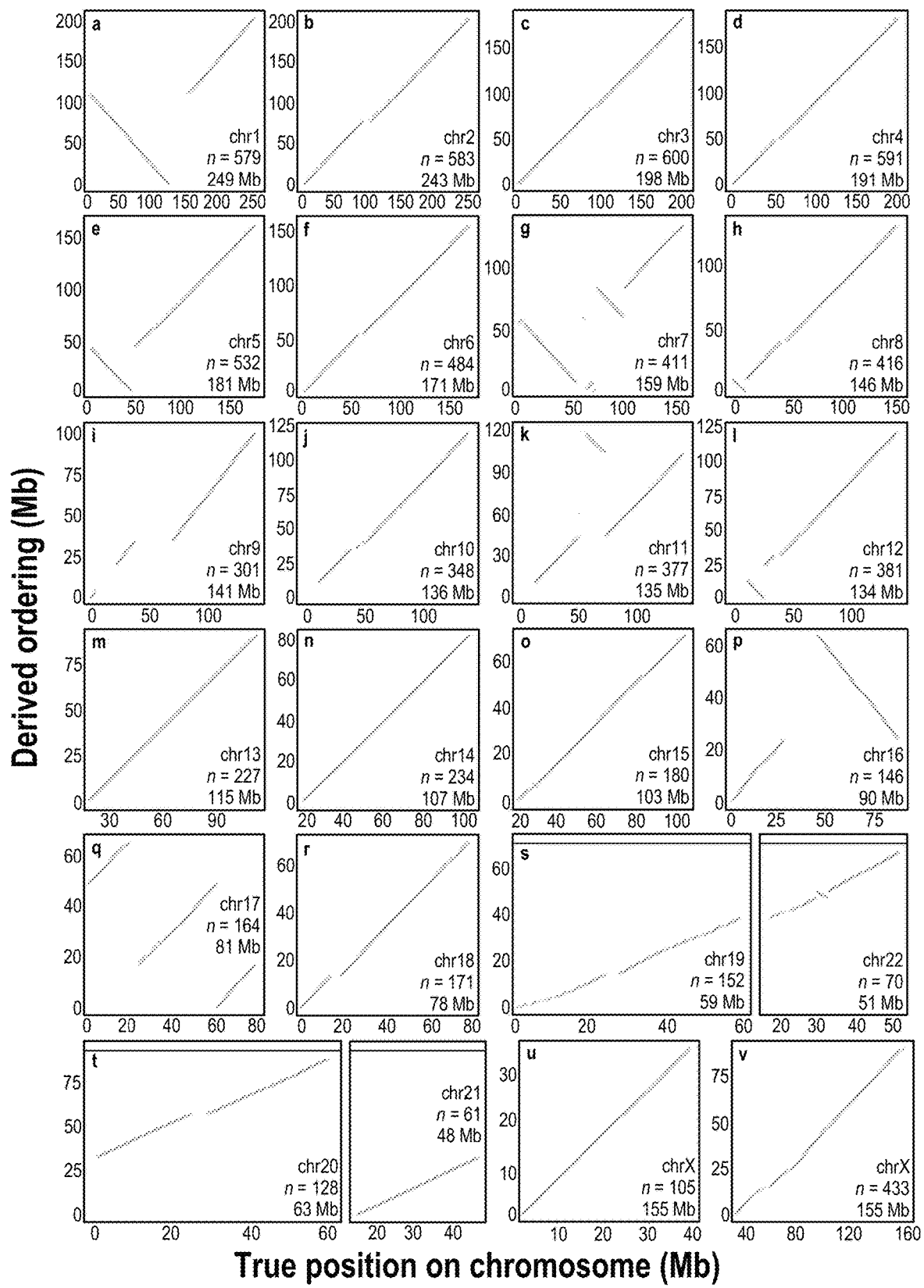
FIG. 7 shows a series of panels illustrating LACHESIS ordering of scaffolds in a de novo human assembly according to some embodiments.

After aligning Hi-C read-pairs from a human male ESC line (Dixon et al. 2012) to this shotgun assembly, LACHESIS was applied to cluster the scaffolds into 23 chromosome groups (the libraries used to generate the shotgun assembly were derived from female DNA; Gnerre et al. 2011), and then to order and orient the scaffolds within each chromosome group (FIGS. 6-8; FIGS. 38. 40-41). Most scaffolds (n=13,528, comprising 98.2% of the length of the shotgun assembly) were clustered into one of the 23 groups (FIG. 6*a*). Nearly all of these groups corresponded to individual chromosomes, with the exceptions of the X chromosome, whose two arms were split in separate groups (FIG. 7*u,v*); one chimeric group containing very little sequence from many chromosomes (FIG. 8*w*); chromosomes 19 and 22, which were "fused" into a single group (FIG. 3*s*); and chromosomes 20 and 21, also fused into a single group (FIG. 7*t*). The fusions are probably due to the greater density of intrachromosomal links observed between short chromosomes in Hi-C data (Lieberman-Aiden et al. 2009; Yaffe & Tanay 2011). Apart from these errors, 98.6% of clustered scaffolds (comprising 99.86% of their sum length) were correctly grouped (FIG. 38), suggesting that Hi-C data are highly informative for the clustering of sequences derived from individual chromosomes, including across centromeres.

Figure 8:
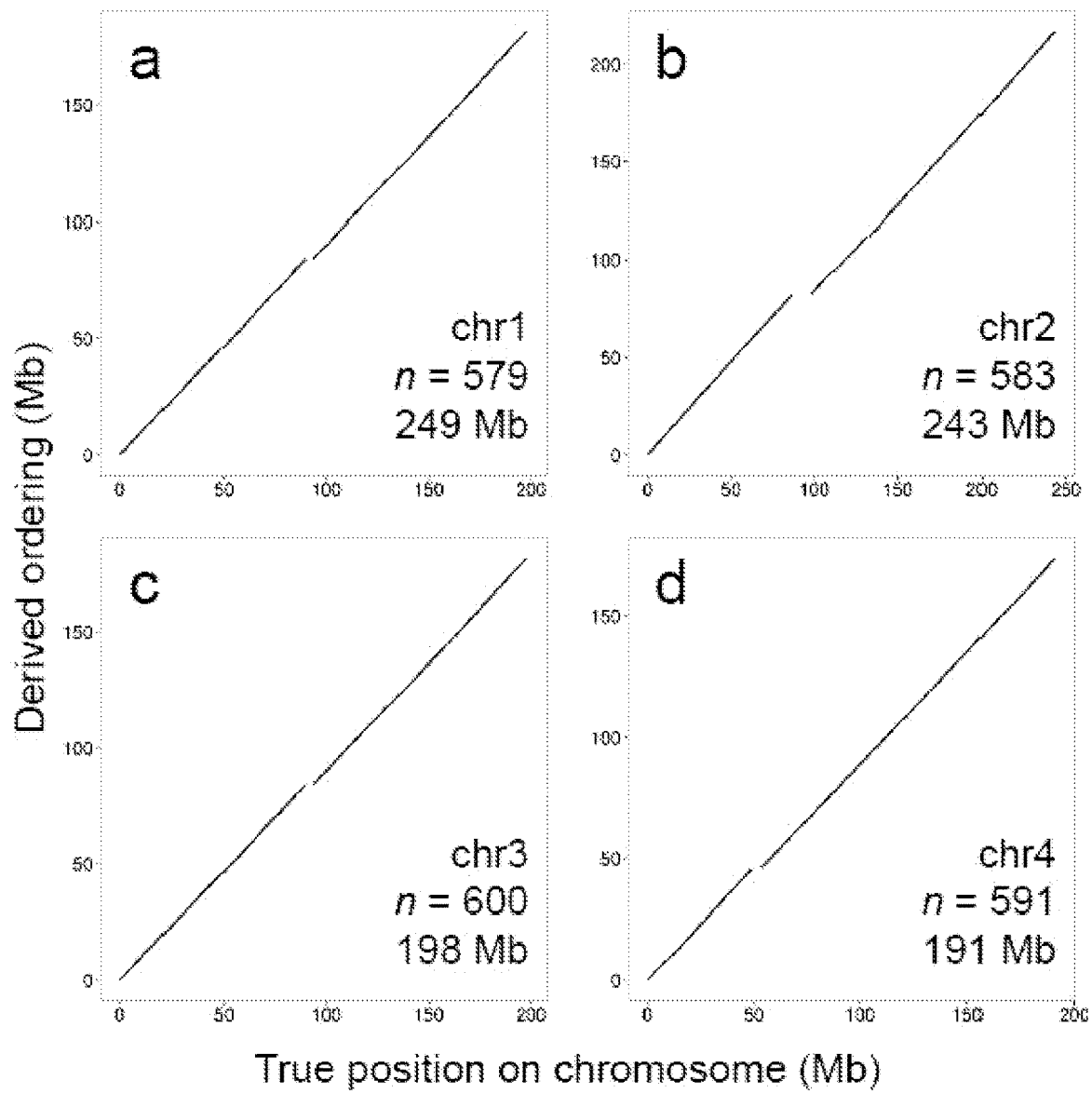
FIG. 8 shows LACHESIS ordering and orienting results on the 23 groups of scaffolds in the human de novo assembly according to some embodiments. Listed in each panel are the identity of the dominant chromosome, the number of scaffolds in the derived ordering, and the reference length of the dominant chromosome. These plots are larger versions of the plots for the very small chimeric group (length=6.5 Mb) not shown in FIG. 7, showing the small region on chromosome 16 that constitutes the dominant chromosome for this group.
Figure 8:
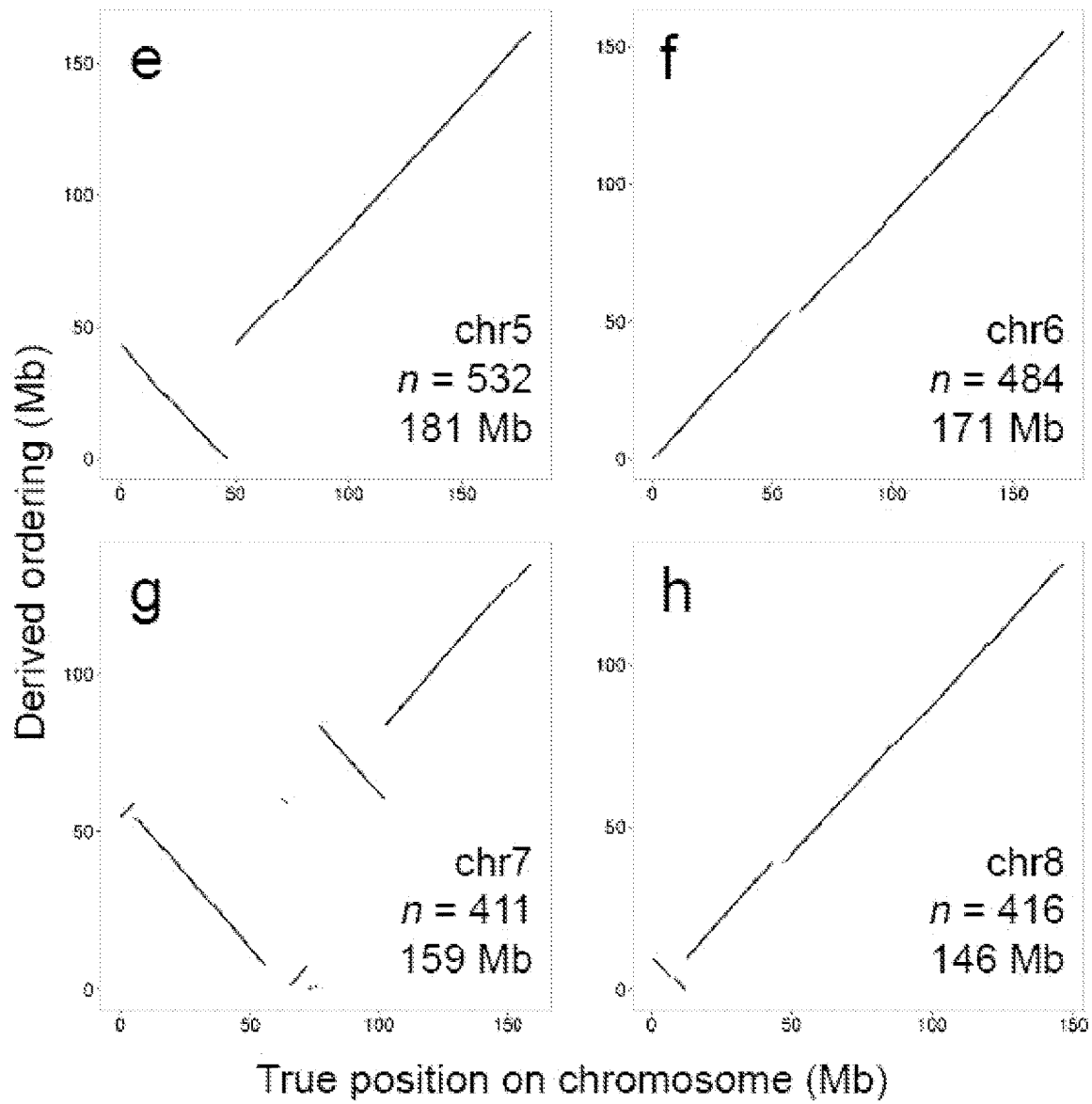
Figure 8:
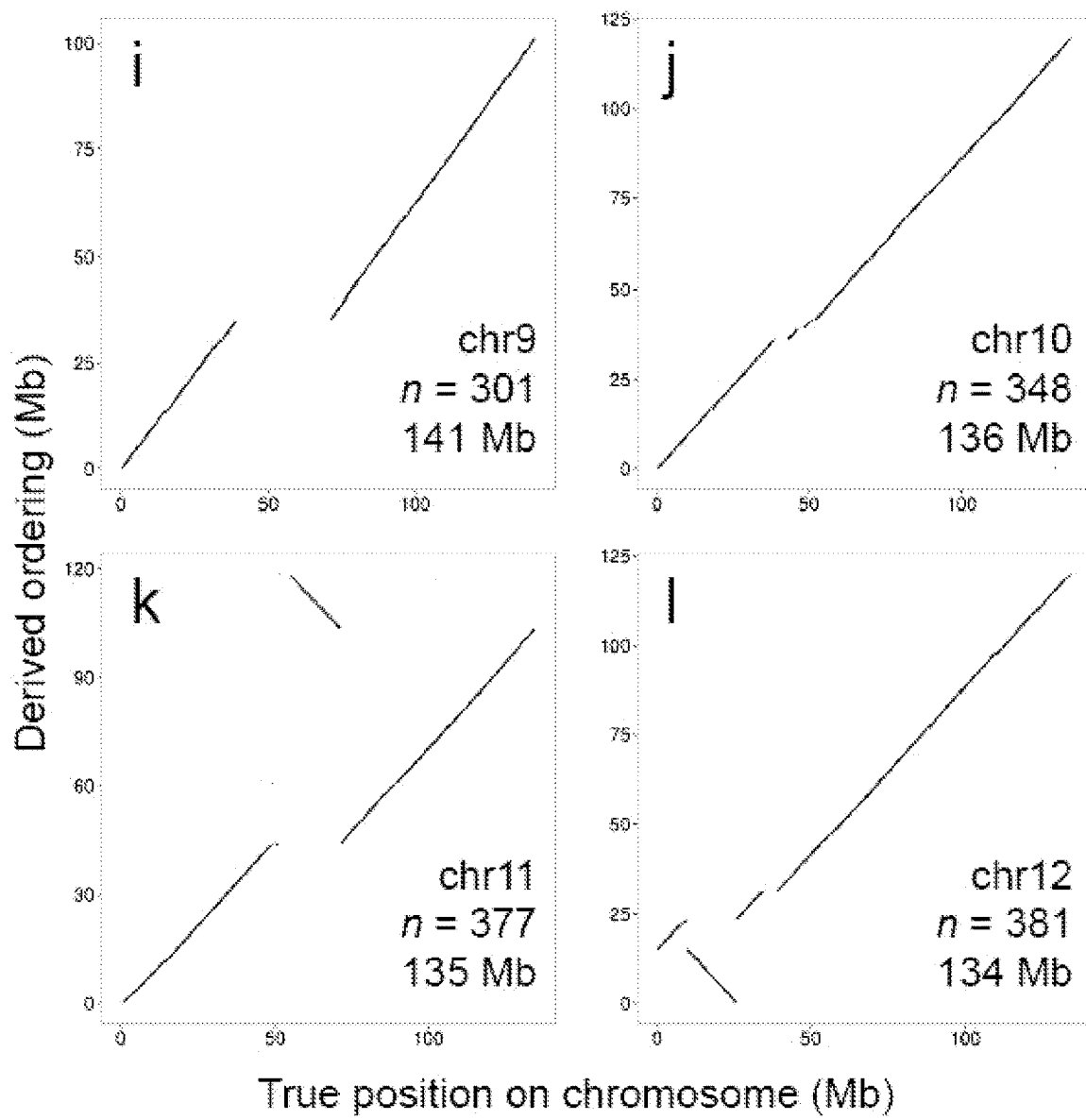
Figure 8:
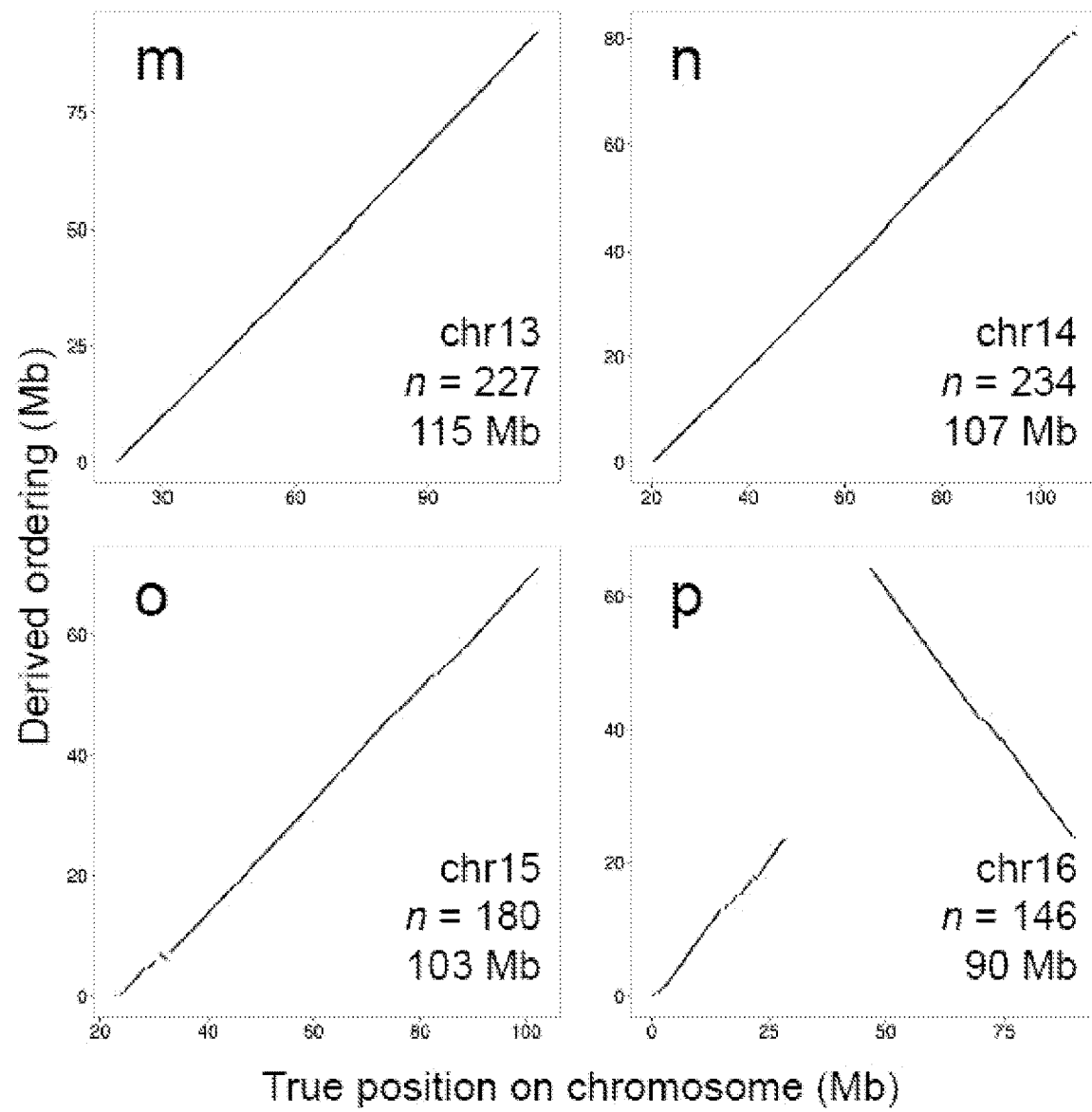
Figure 8:
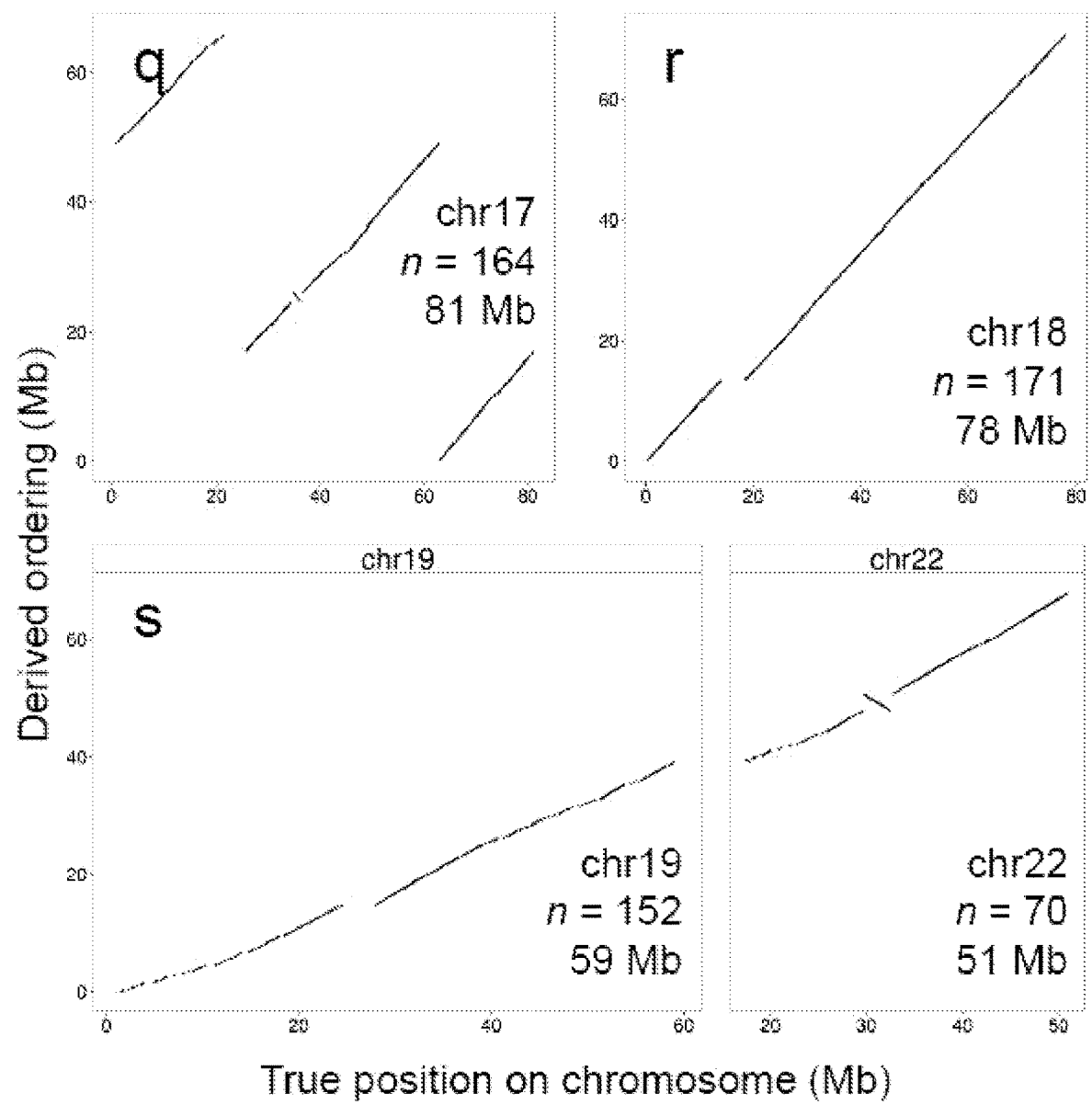
Figure 8:
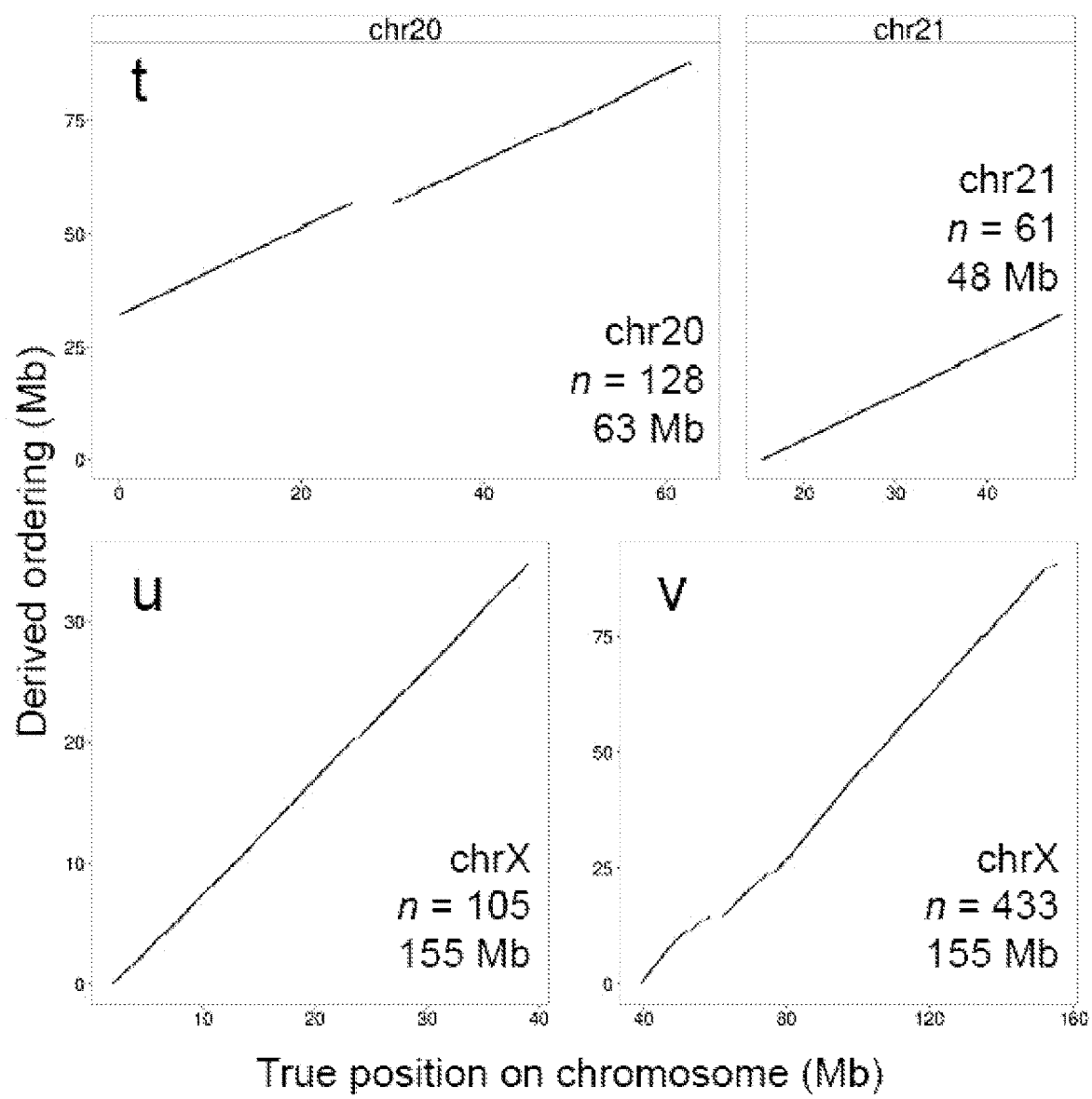
Figure 8:
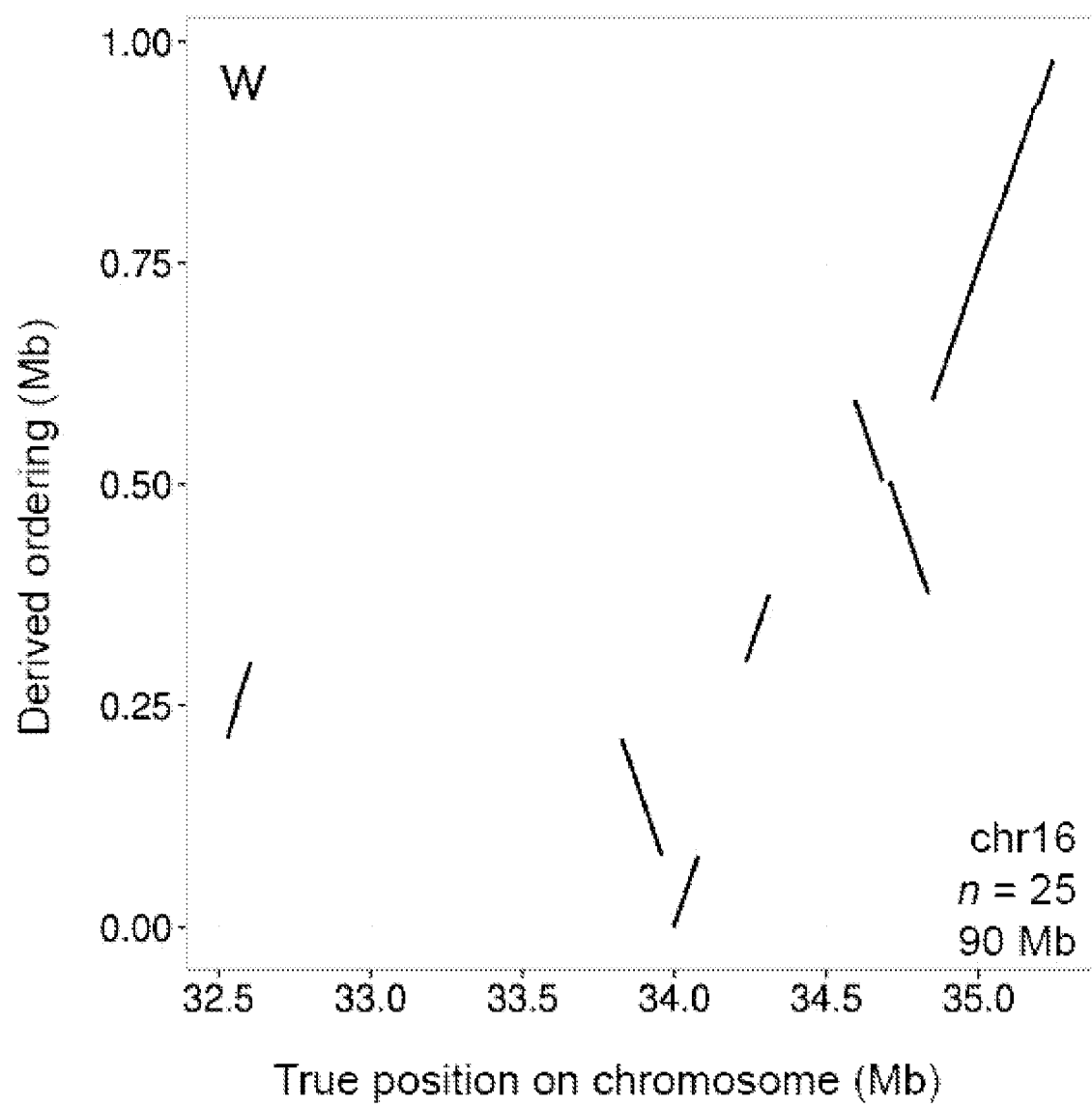

Within each chromosome group, the vast majority of the length of the clustered scaffolds was successfully ordered and oriented by LACHESIS (94.4% or 2.54 Gb; FIG. 38). The predicted orderings are highly concordant with the reference human genome (GRCh37), except for the occasional rearrangement of large segments within which nearly all scaffolds were well-ordered, including across megabase-scale centromere gaps (FIG. 7; FIG. 8). For example, scaffolds corresponding to the long and short arms of chromosome 1 are grouped together and respectively very well-ordered, but the reconstructed arms are joined at their telomeric ends (FIG. 6b). To quantify local errors, ordering errors were defined as instances where a contig or scaffold is not in the expected order with respect to its immediate neighbors, and orientation errors as instances where a contig or scaffold is not in the expected orientation implied by its immediate predecessor in the ordering. By these definitions, 99.2% of clustered scaffolds, representing 99.5% of the sum length, were correctly ordered; 97.5% of clustered scaffolds, representing 98.8% of the sum length, were correctly oriented.

Figure 9:
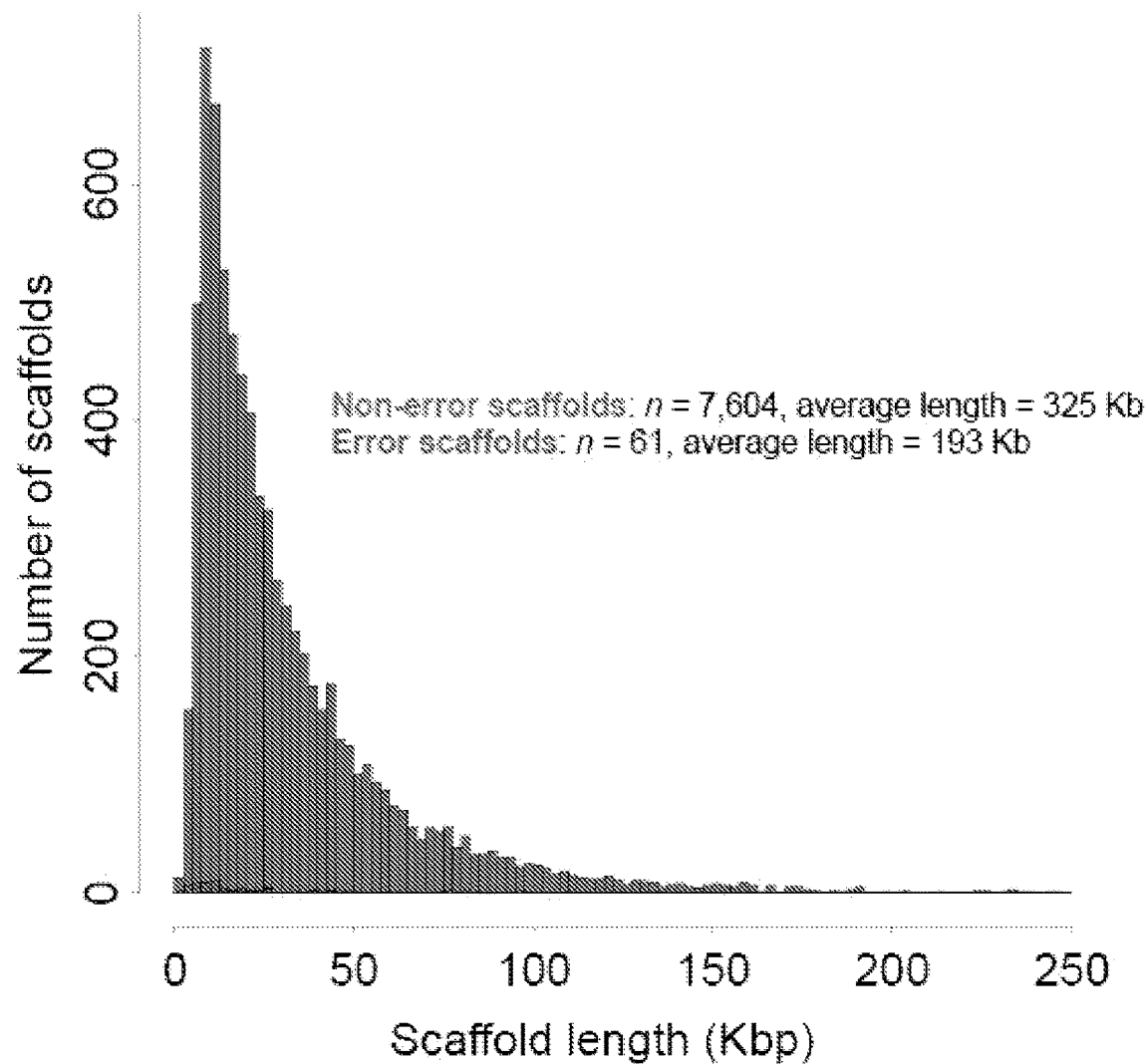
FIG. 9 shows that scaffolds associated with ordering errors tend to be shorter than correctly ordered scaffolds according to some embodiments. A histogram of the lengths of all scaffolds in the de novo human assembly which LACHESIS places in orderings and which map to the human reference. Scaffolds marked with ordering errors are shown in red; all other scaffolds are shown in blue. For clarity, six scaffolds of length >250 Kbp (none of which have ordering errors) are not shown.
Figure 10:
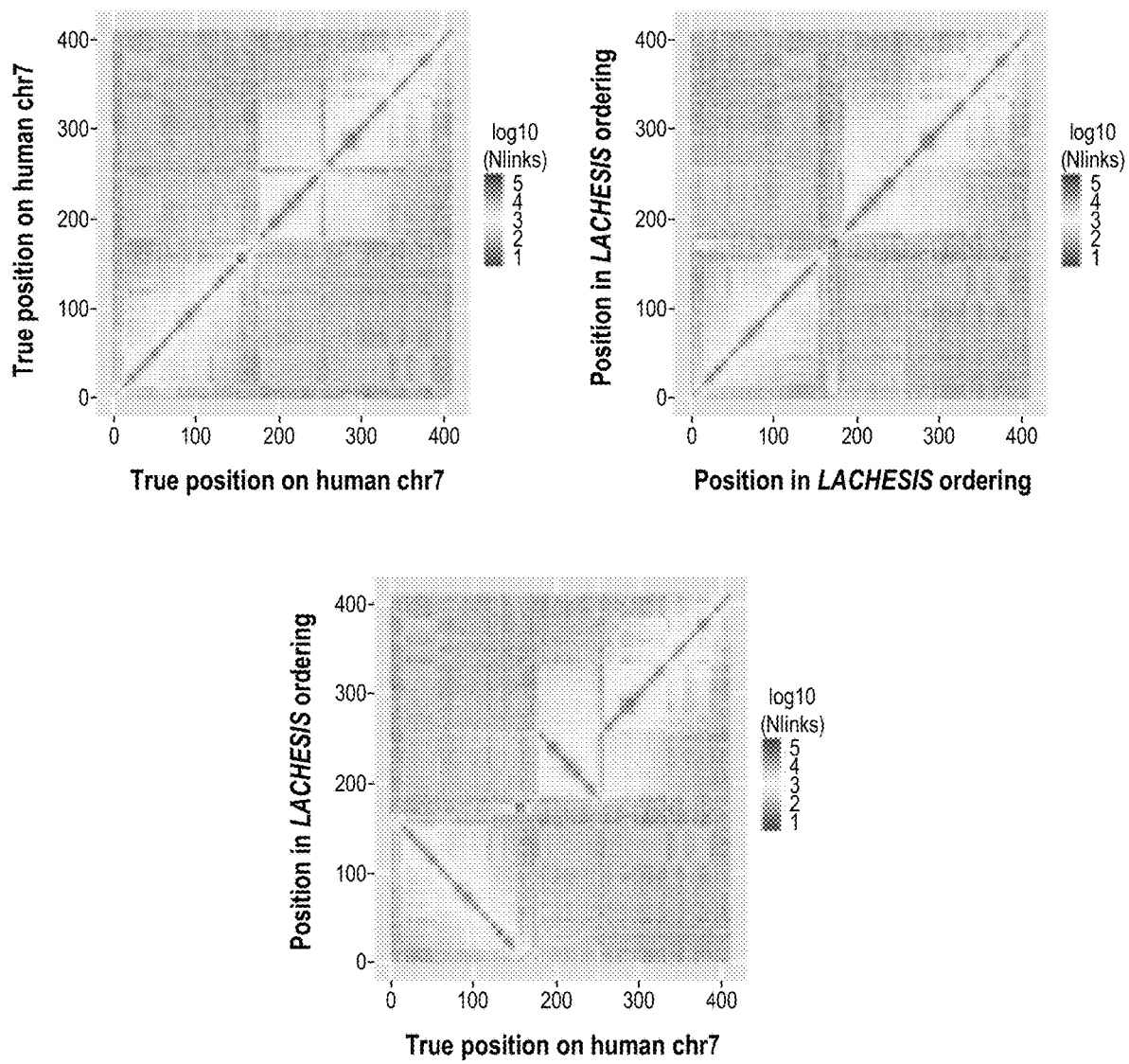
FIG. 10 shows an example of LACHESIS assembly errors due to long-range chromatin interactions according to some embodiments. Shown are three heatmaps of the density of Hi-C links between scaffolds of the de novo human assembly for chromosome 7. Only mapping contigs of length ≥10 Kb are shown. a. The scaffolds are ordered on both axes by their true position on chromosome 7. Note the presence of large domains (squares along diagonal) with far more internal than external interaction. b. The scaffolds are ordered on both axes by their position in the LACHESIS ordering in the group corresponding to chromosome 7. c. The scaffolds are ordered on the x-axis by their true position, and on the y-axis by their position in the LACHESIS ordering, revealing incorrect fusions of domains. Compare to FIG. 8g.

On visual inspection of the predicted versus expected orderings, most of the ordering errors involve the inversion of local segments that have one or several contiguous scaffolds (FIG. 8). Incorrectly ordered scaffolds are relatively short and are enriched for segmental duplications and simple repeats, relative to correctly ordered scaffolds (FIG. 9; FIG. 42). This suggests that complexities in the primary sequence are the source of many ordering errors, possibly via inaccuracies in the shotgun assembly or by confounding the mapping of Hi-C read-pairs. Other errors appear to be associated with the non-uniform distribution of biological interactions, e.g., chromatin domains at various scales (FIG. 10). To address this in part, a quality score was developed for ordering and orientation. Local accuracy was better for scaffolds with high quality scores (FIG. 38). For scaffolds with high quality scores occurring within the assembly trunk, which comprise 2.09 Gb or 76.4% of the overall shotgun assembly, 99.9% of sequence is correctly ordered and 99.7% correctly oriented (FIG. 40).

Figure 11:
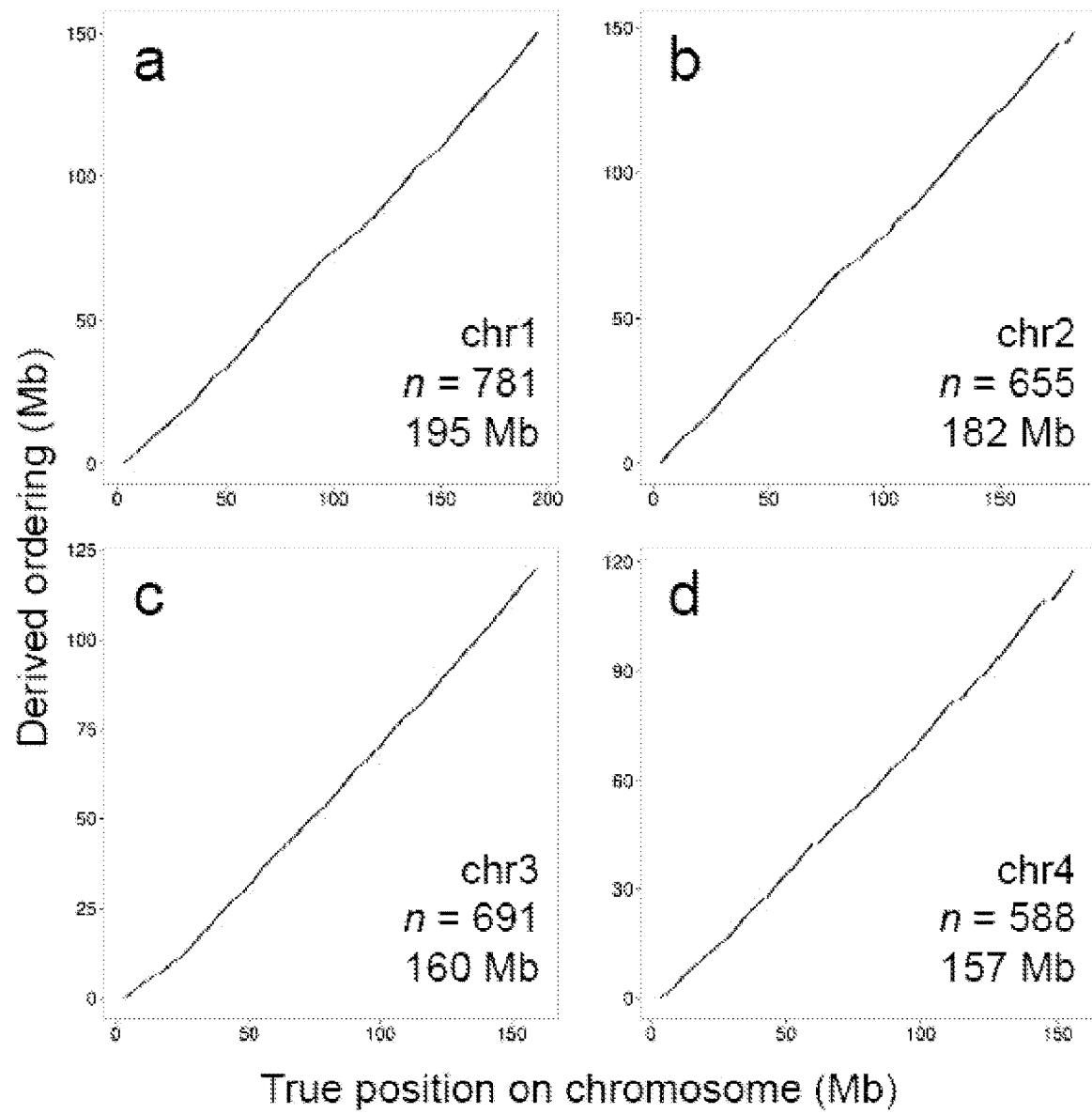
FIG. 11 shows LACHESIS ordering and orienting results on the 20 groups of scaffolds in the mouse de novo assembly according to some embodiments. Listed in each panel are the identity of the dominant chromosome, the number of scaffolds in the derived ordering, and the reference length of the dominant chromosome.
Figure 11:
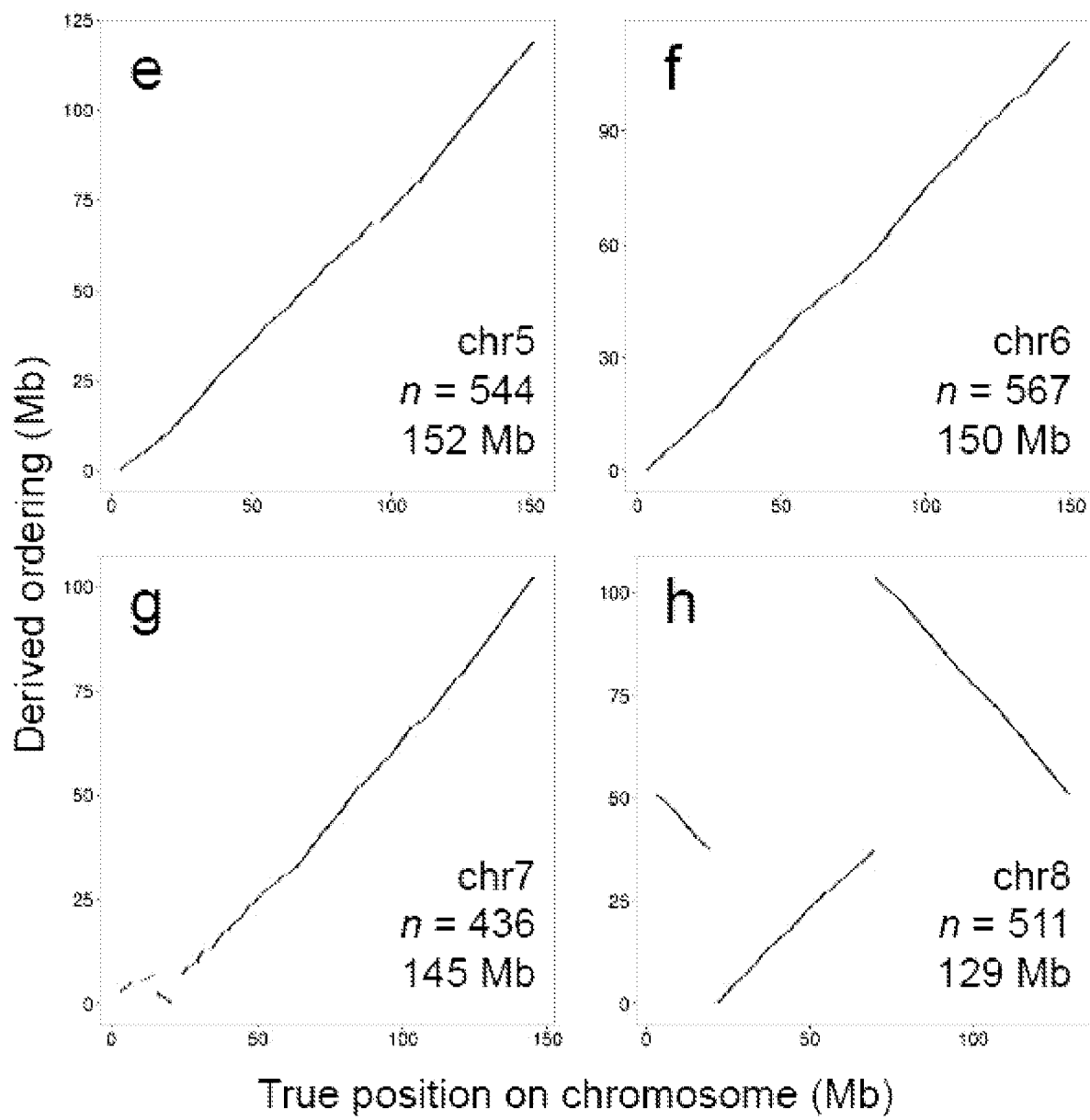
Figure 11:
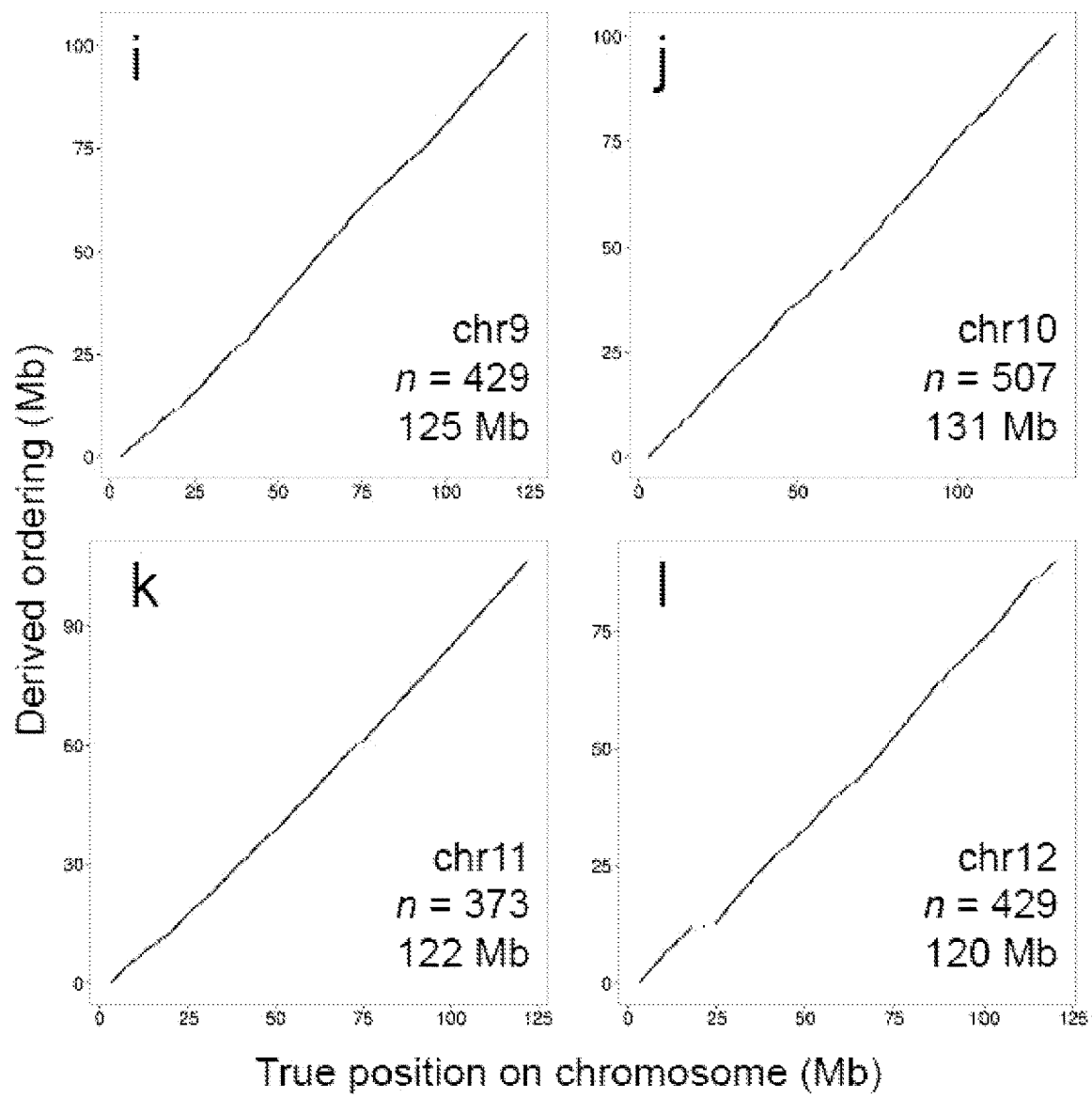
Figure 11:
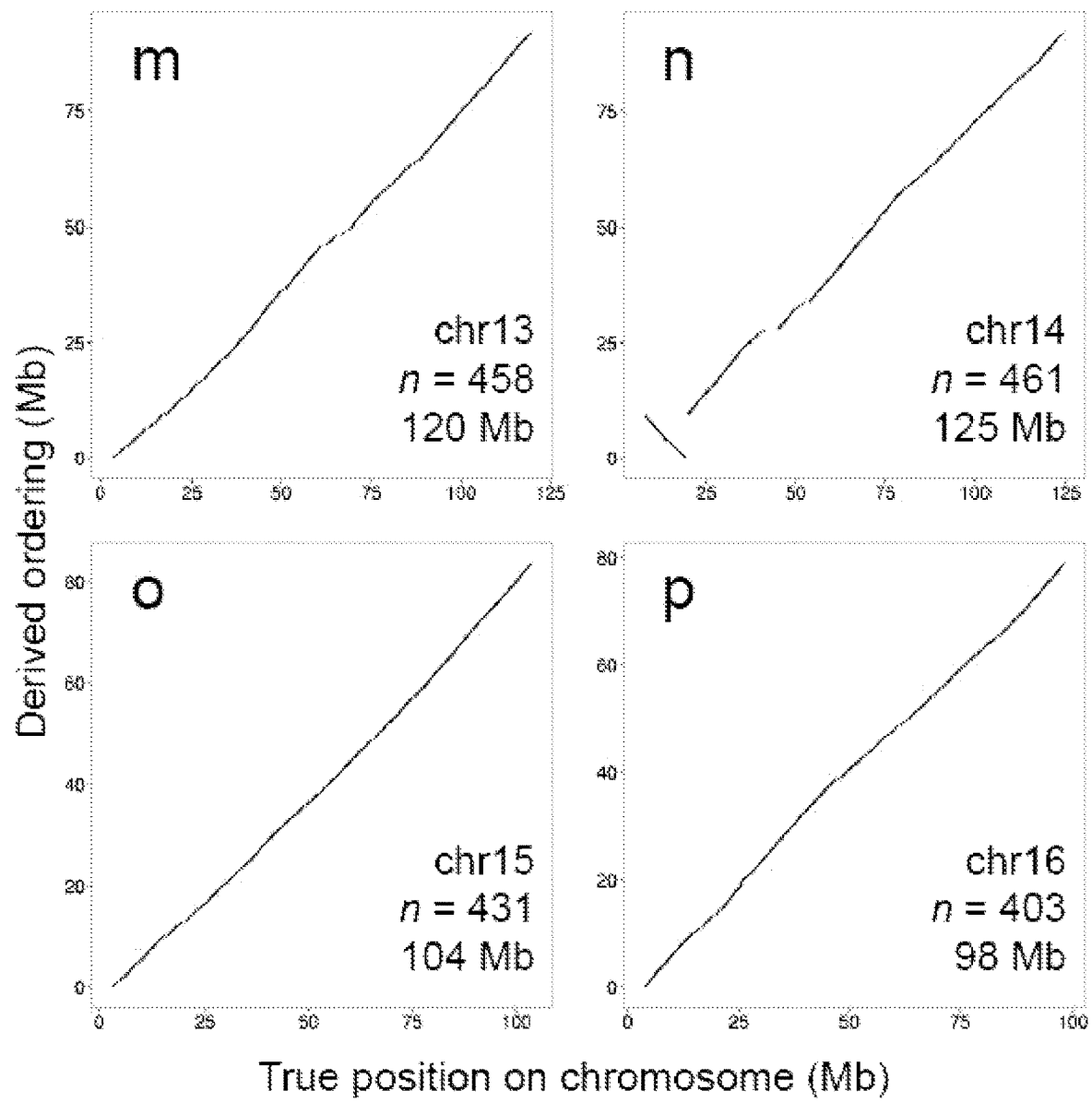
Figure 11:
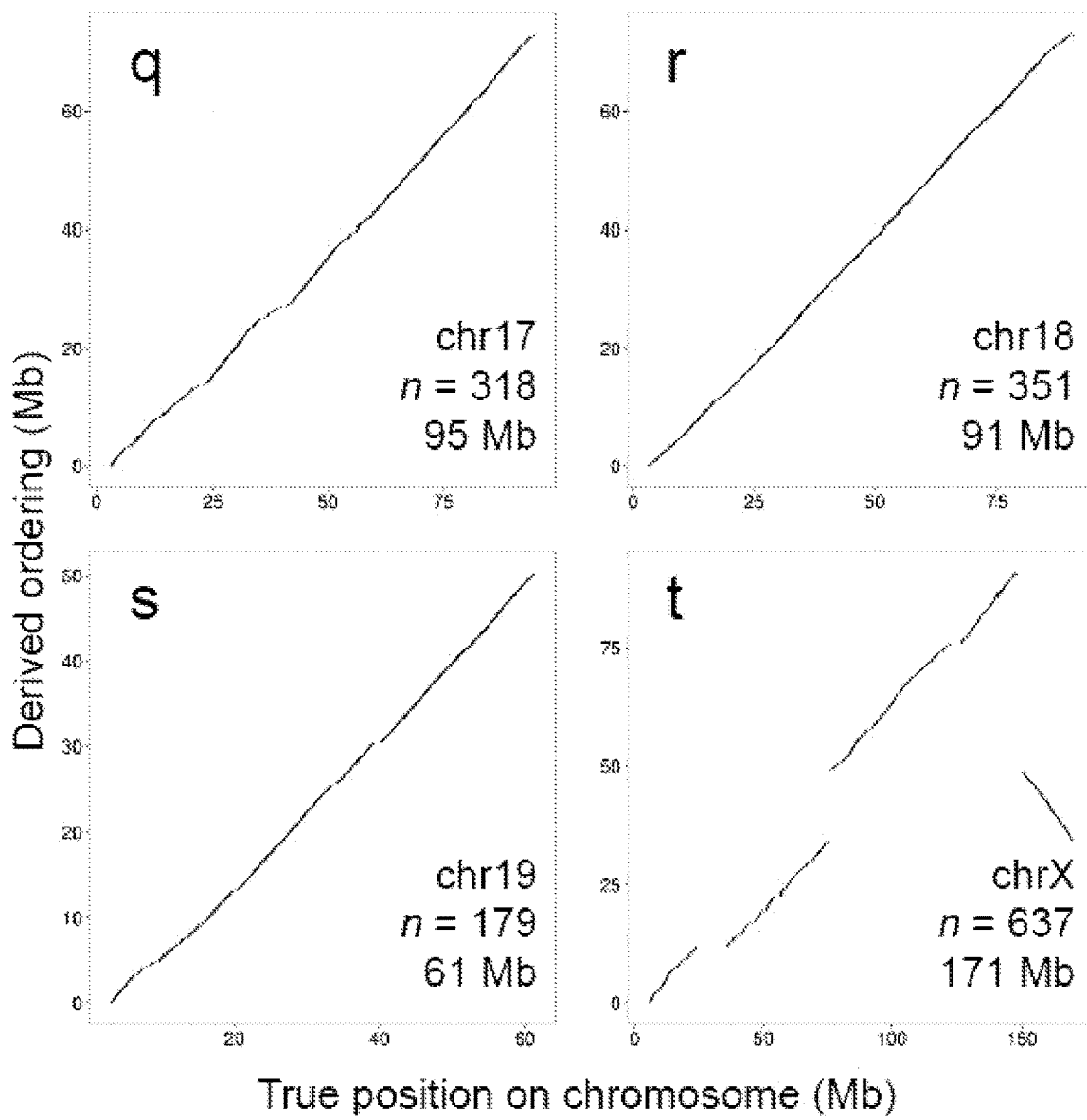

The chromosome-scale de novo assembly of the mouse genome was also performed using an identical approach. ALLPATHS-LG was first used to assemble only shotgun fragment and short jump (~2.2 Kb) matepair sequences (Gnerre et al. 2011) to an N50 scaffold length of 224 Kb and a total length of 2.37 Gb. After aligning Hi-C read-pairs from a mouse ESC line (Dixon et al. 2012) to this shotgun assembly, the LACHESIS method was applied to cluster the scaffolds into 20 chromosome groups, and then to order and orient the scaffolds within each chromosome group (FIG. 6c, 6d; FIG. 38; FIG. 11; FIGS. 40, 43). Most scaffolds (n=22,802, comprising 98.0% of the length of the shotgun assembly) were clustered into one of the 20 groups (FIG. 6c). There was a clear 1-to-1 correspondence between these groups and bona fide chromosomes (GRCm38), although a small part of mouse chromosome 10 (2.6 Mb) was erroneously clustered with chromosome 8 (FIG. 43). 99.5% of clustered scaffolds (comprising 99.76% of their sum length) were correctly grouped (FIG. 38). The majority of the length of the clustered scaffolds was ordered and oriented by LACHESIS (86.7% or 2.02 Gb; FIG. 38). 99.5% of clustered scaffolds, representing 98.9% of the sum length, were correctly ordered; 95.4% of scaffolds, representing 98.1% of the sum length, were correctly oriented. Overall, the results for chromosome-scale de novo assembly of the mouse and human genomes are highly consistent.

Chromosome-Scale De Novo Assembly of the Fruit Fly Genome.

Figure 12:
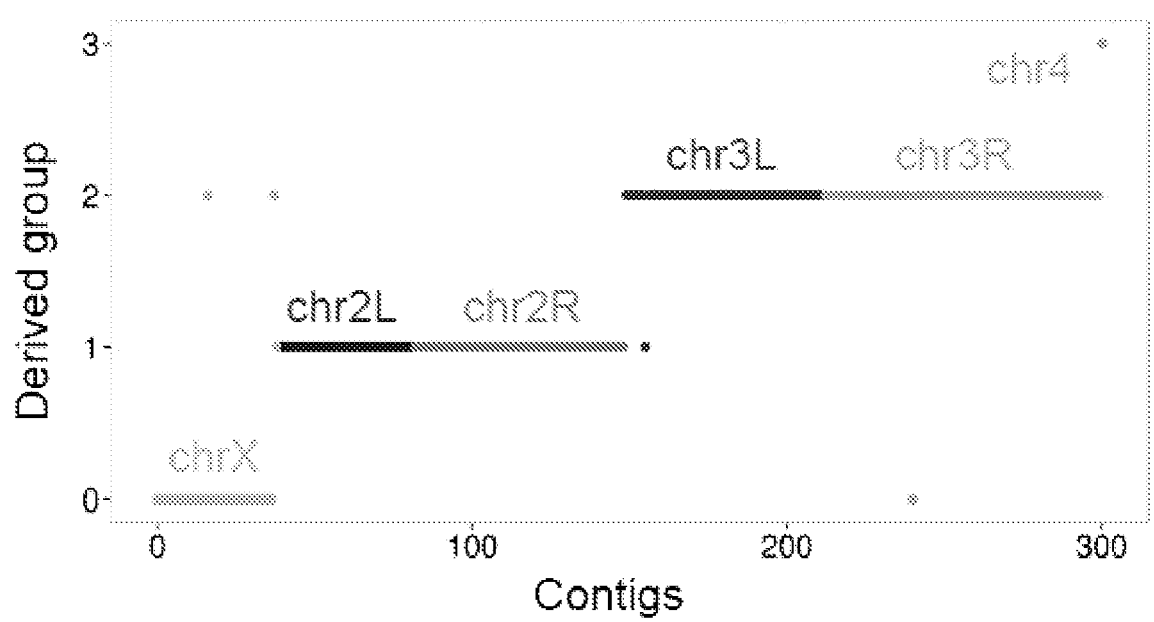
FIG. 12 shows LACHESIS clustering results on the *Drosophila* de novo assembly according to some embodiments. Shown on the x-axis are the 301 contigs (of 4,568 total contigs; total length: 43.8 Mb) that are long (≥250 GATC restriction sites) and not repetitive (Hi-C link density less than 2 times average), which LACHESIS used as informative for clustering. The y-axis shows the four groups created by LACHESIS, with the order chosen for the purposes of clarity. Each contig is shown as a dot, with a color indicating the chromosome to which the contig truly aligns, including the chromosome arm in the case of chromosomes 2 and 3.

To further evaluate the generality of this method, it was then applied to the de novo assembly of *Drosophila melanogaster*, for which a high-quality reference genome is also available as a gold standard for comparison. ALLPATHS-LG was first used to assemble shotgun fragment sequences (without jumping libraries) to an N50 contig length of 68 Kb and a total length of 127 Mb (Gnerre et al. 2011; Mackay et al. 2012). Next, Hi-C read-pairs derived from *D. melanogaster* (Sexton et al. 2012) were aligned to this shotgun assembly and used LACHESIS to cluster the contigs into 4 chromosome groups. Most contigs (81.2% of the length of the shotgun assembly) were clustered into one of the 4 groups (FIG. 12). This proportion is lower than that for the assemblies described above (98% for human and mouse), most likely due to the lower contiguity of the shotgun assembly (N50 contig size of 68 Kb for *Drosophila* vs. N50 scaffold size of 437 Kb and 224 Kb for human and mouse, respectively). Nonetheless, the four groups corresponded well to the four expected chromosomes (X, 2, 3, and 4), even though chromosome 4 is minuscule compared to the others (1.4 Mb or ~1% of the reference genome). 89.5% of the clustered scaffolds, comprising 96.6% of their sum length, were correctly grouped.

Figure 13:
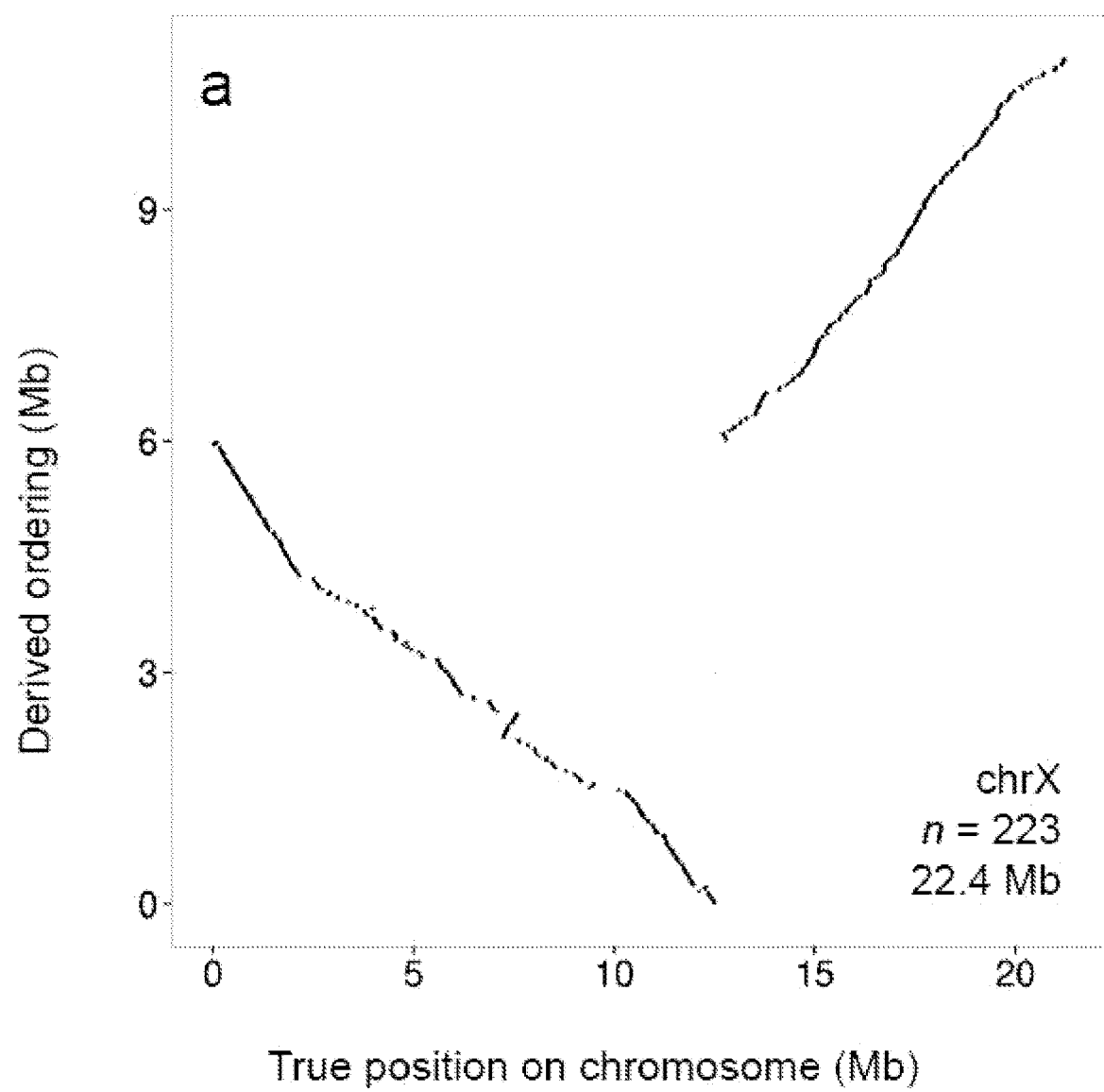
FIG. 13 shows LACHESIS ordering and orienting results on the 4 groups of contigs in the *Drosophila* de novo assembly according to some embodiments. For each ordering, only the contigs on the "dominant chromosome"—that is, the chromosome containing the plurality of aligned sequence—are shown (see FIG. 44). Also listed in each panel are the identity of the dominant chromosome, the number of contigs in the derived ordering, and the reference length of the dominant chromosome.
Figure 13:
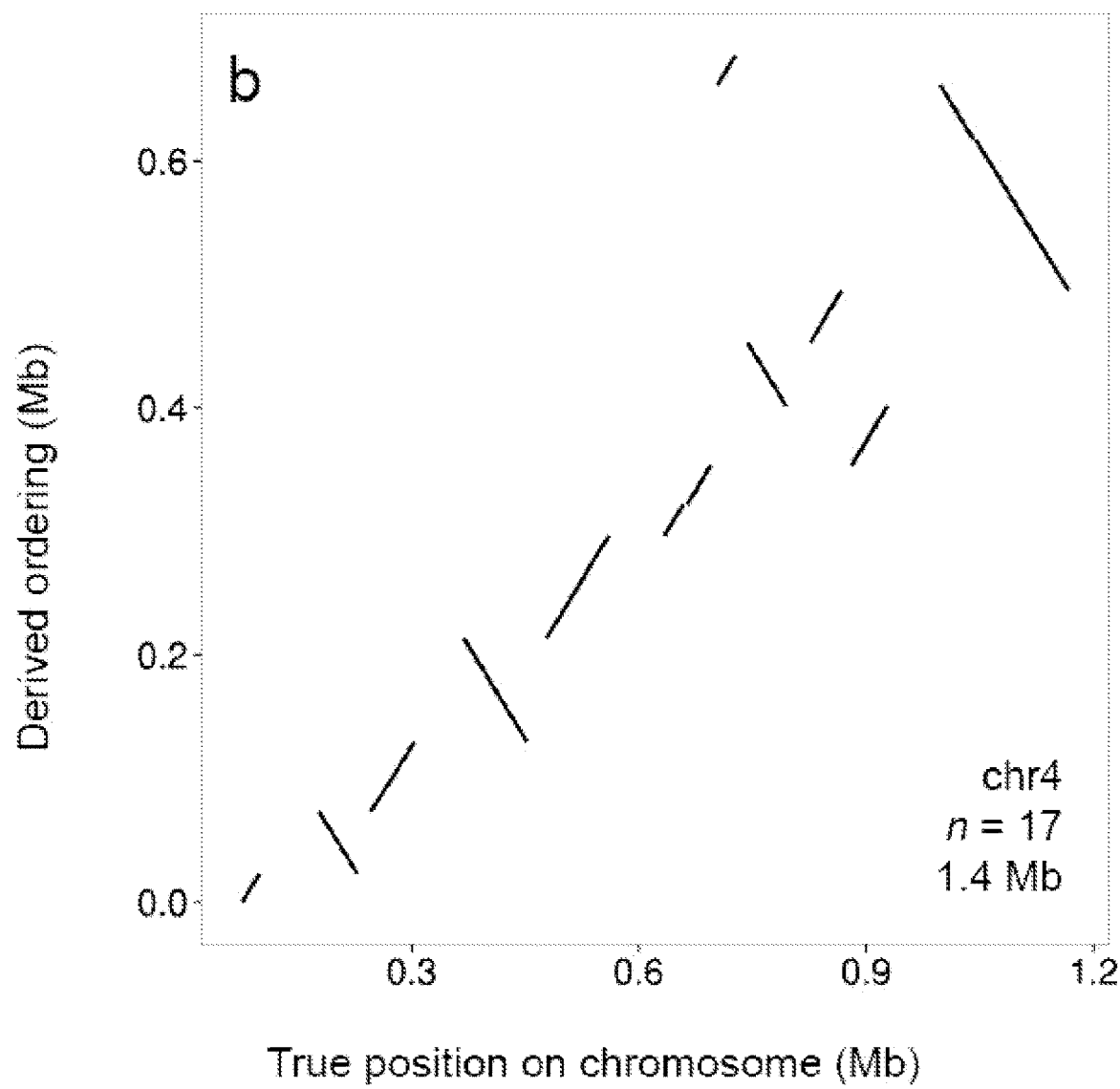
Figure 13:
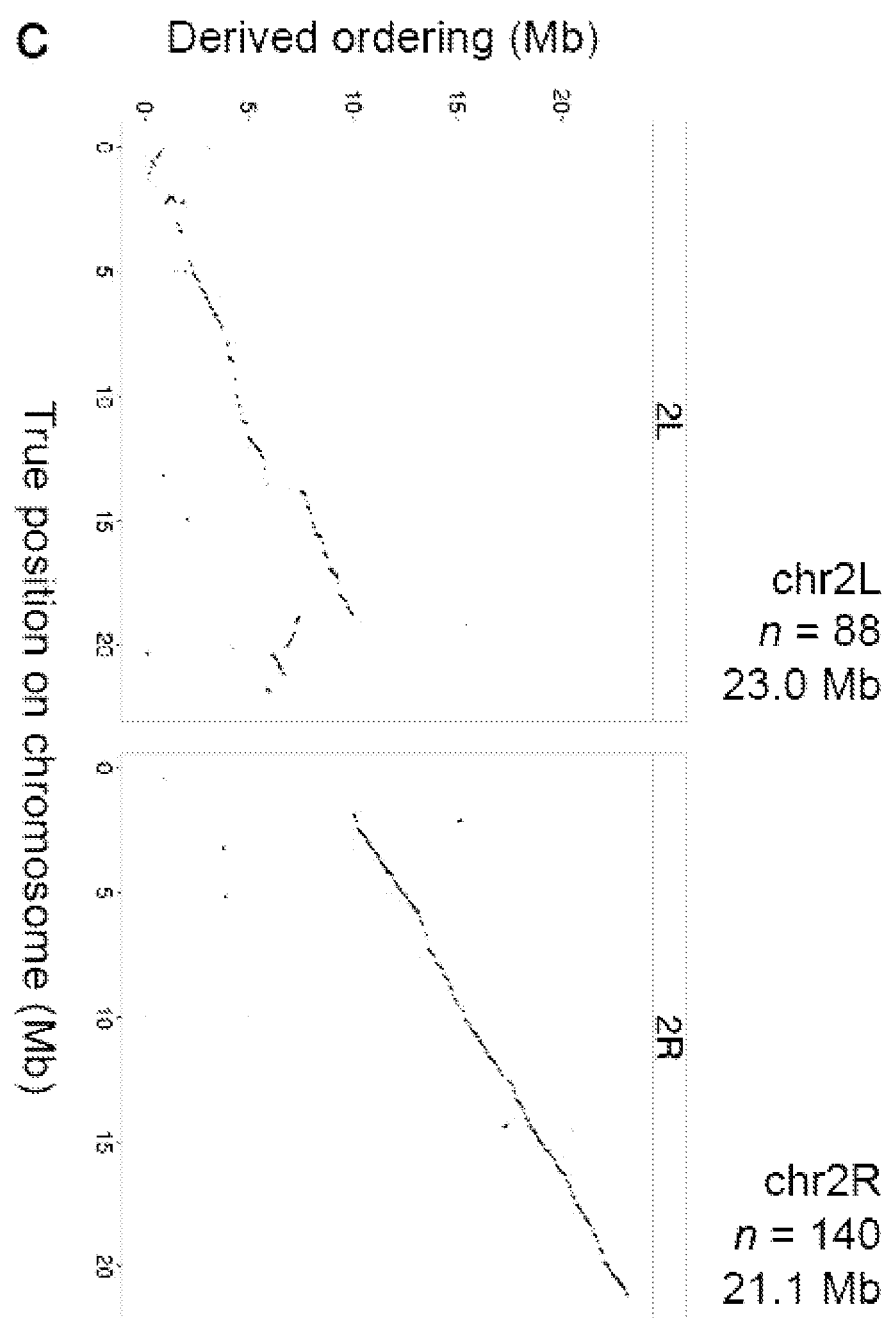
Figure 13:
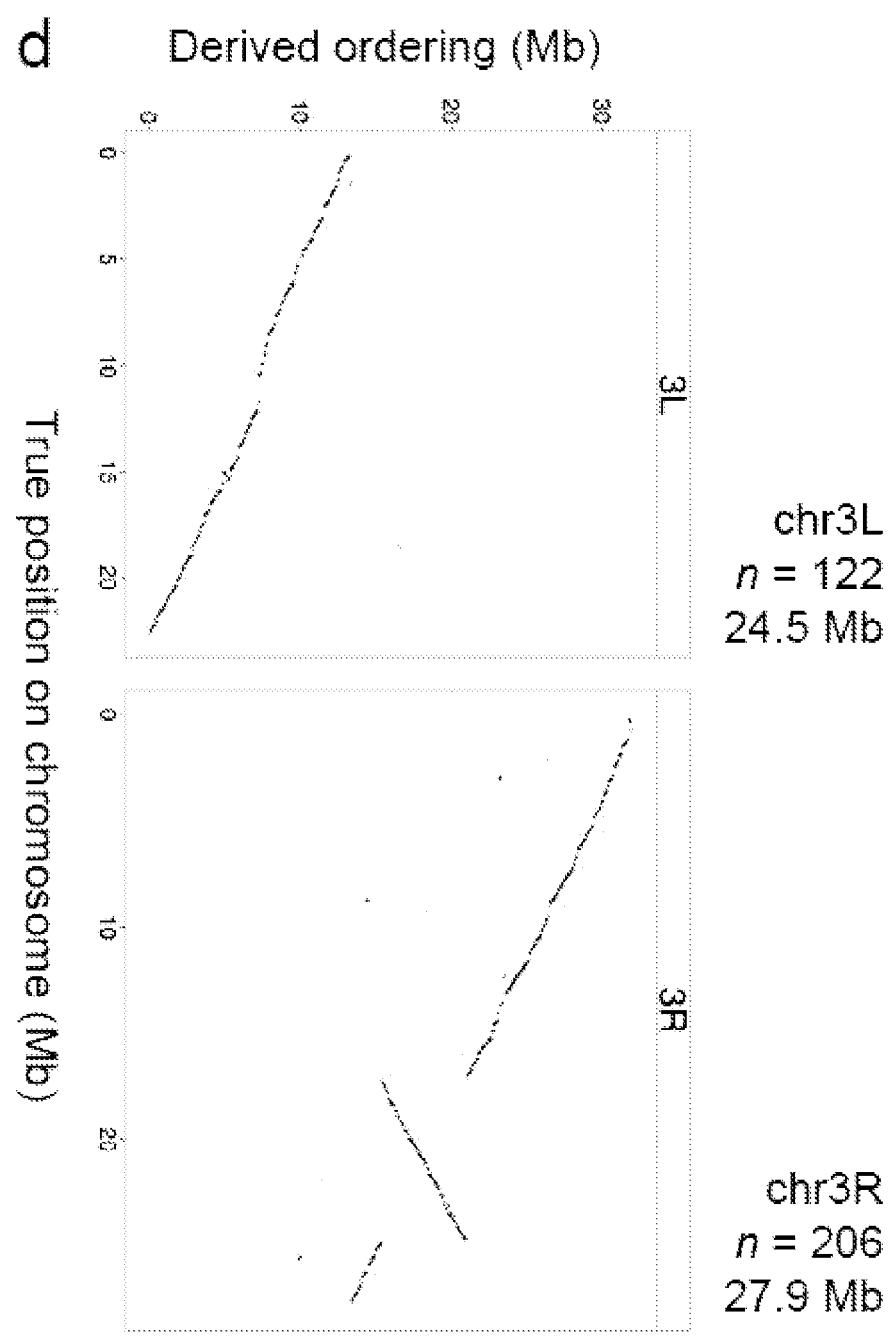

LACHESIS was then applied to order and orient the *Drosophila* contigs within each of the 4 chromosome groups (FIG. 44; FIG. 13). A lower proportion of the shotgun assembly was ordered (82.0% by length for fly versus 94.4% for human), again likely because the *Drosophila* assembly has shorter contigs than the mammalian shotgun assemblies described above. The predicted order corresponded very well with the actual order based on contig alignments to the *D. melanogaster* reference genome (FB2013_02, euchromatic sequences only), and the R and L arms of chromosomes 2 and 3 were well-separated (FIG. 13). Once again, a subset of the chromosome groups contained rearrangements of large segments within which nearly all contigs were well-ordered. At a local scale, 94.8% of clustered contigs (95.4% of sum length) were correctly ordered, and 93.9% of clustered contigs (95.9% of sum length) were correctly oriented (FIG. 38).

Performance as a Function of Contig Size or Quantity of Hi-C Data.

Figure 14:
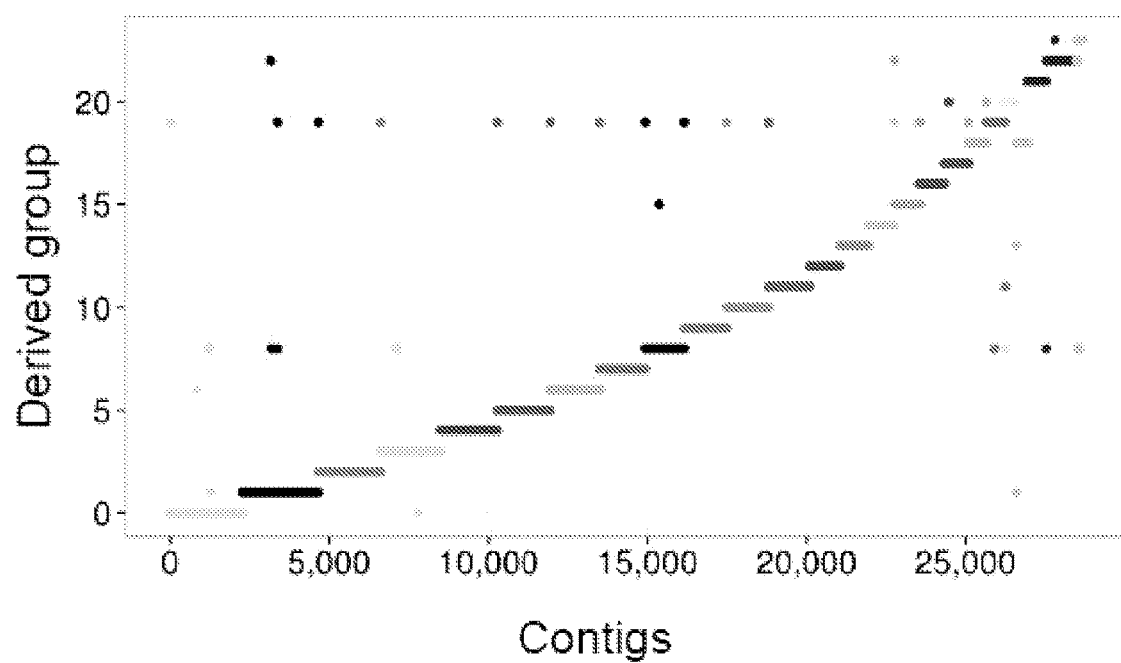
FIG. 14 shows LACHESIS clustering results on simulated 100-Kb contigs of the human reference genome according to some embodiments. The human genome was split into simulated 100-Kb contigs and LACHESIS was used to cluster these contigs into groups. The 28,689 contigs (total length: 2.87 Gb) are ordered on the x-axis in order of ascending chromosome number and then position on the chromosome. The y-axis represents the 24 groups created by LACHESIS, with the order chosen for the purposes of clarity. Each 100-Kb contig is shown as a dot, with a color indicating the chromosome on which it belongs. The color scheme is the standard SKY (spectral karyotyping) color scheme for human. Not shown are the 7.5% of contigs not placed into groups due to lack of unique sequence content, generally corresponding to centromeres.
Figure 15:
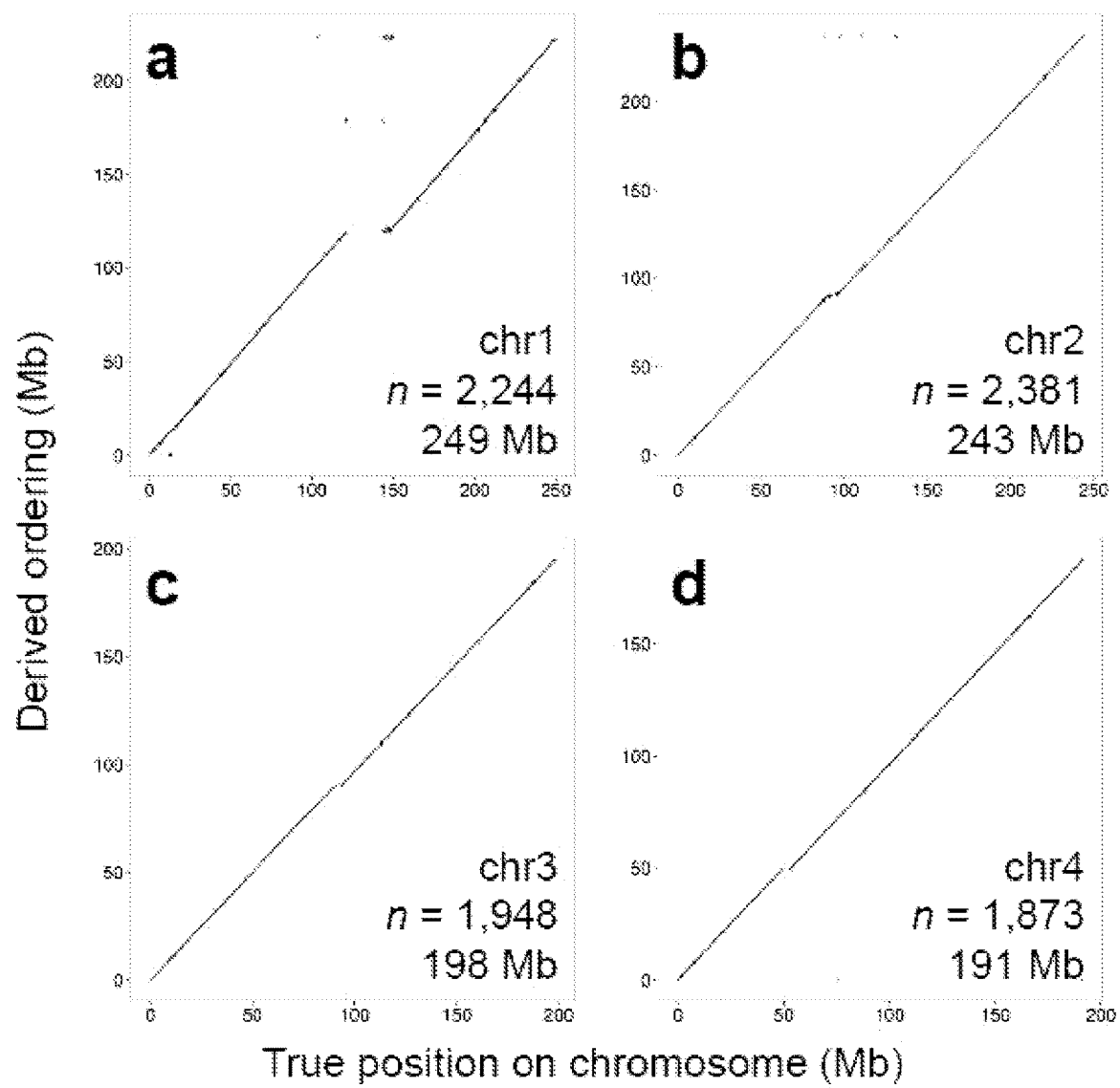
FIG. 15 shows LACHESIS ordering and orienting results on all 23 groups of simulated 100-Kb contigs in the human reference genome according to some embodiments. Listed in each panel are the identity of the dominant chromosome, the number of contigs in the derived ordering, and the reference length of the dominant chromosome.
Figure 15:
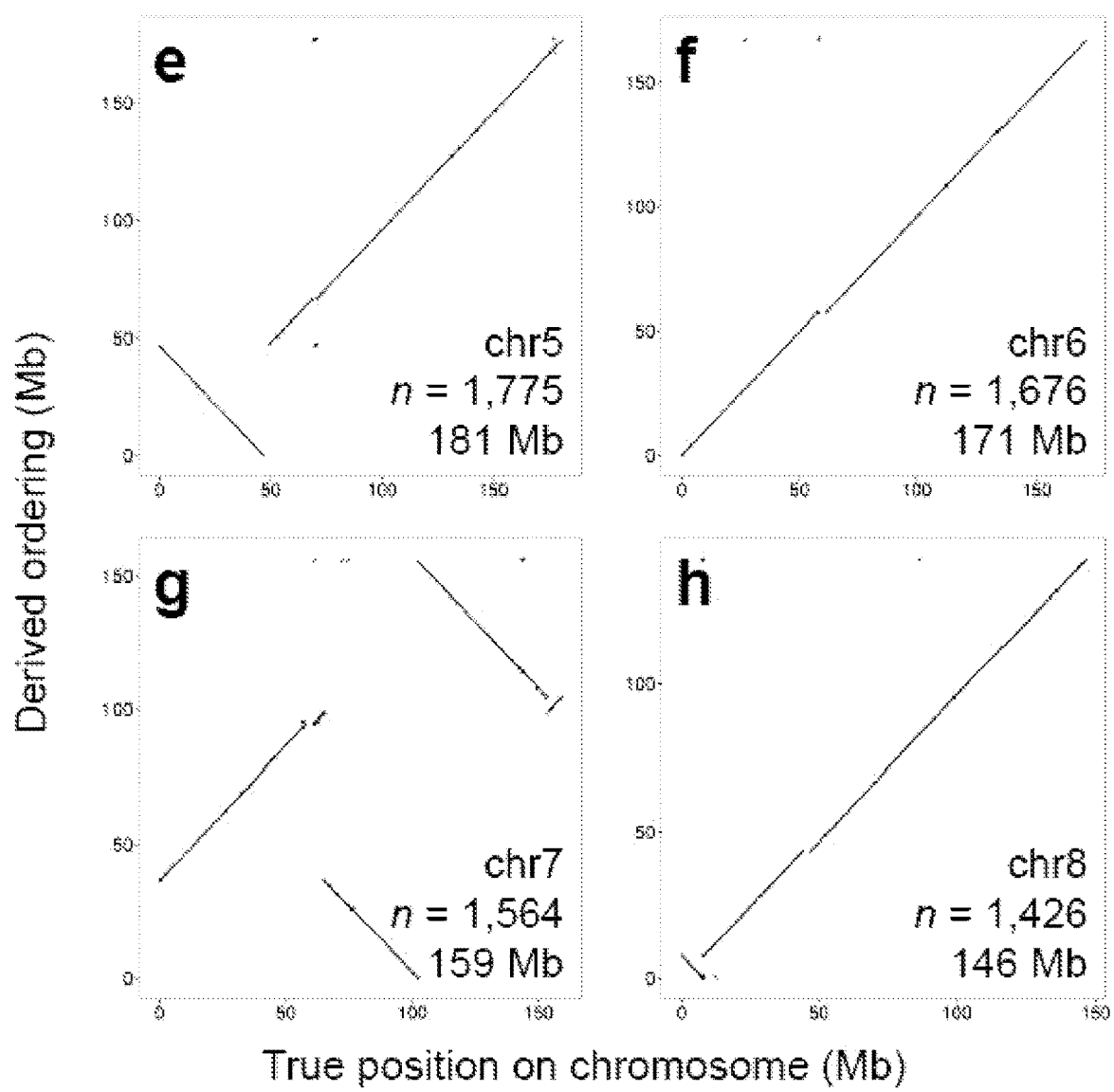
Figure 15:
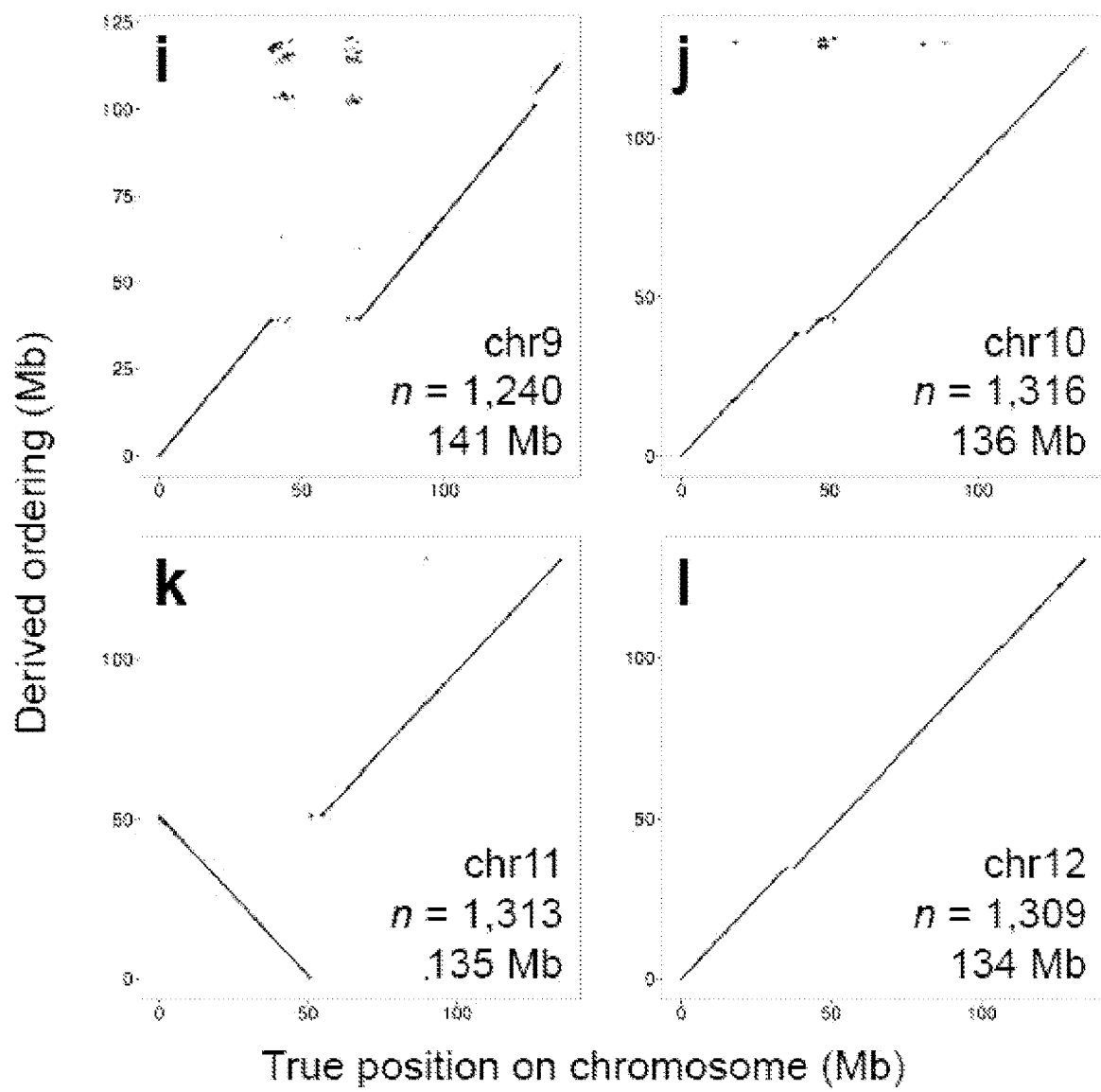
Figure 15:
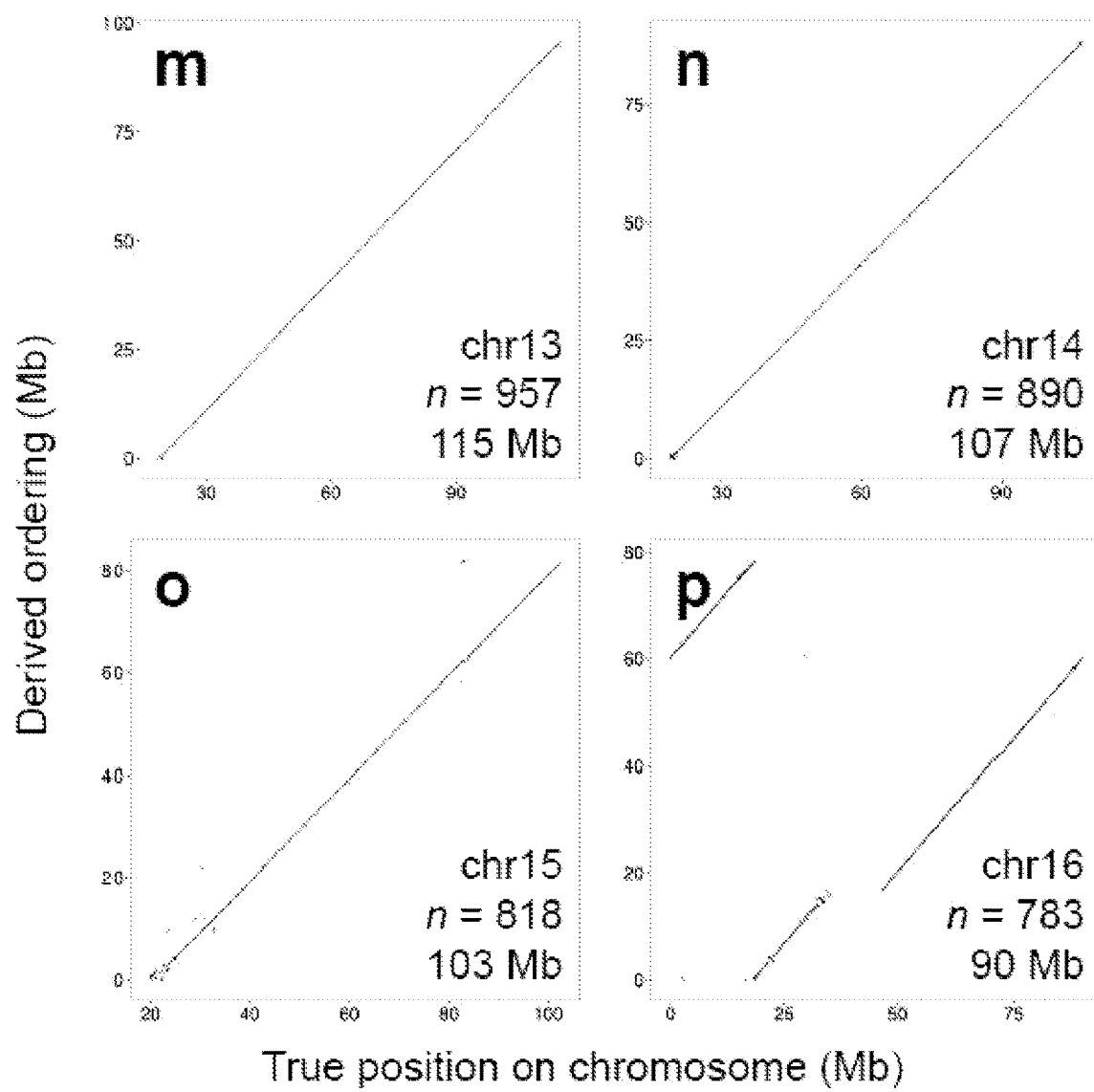
Figure 15:
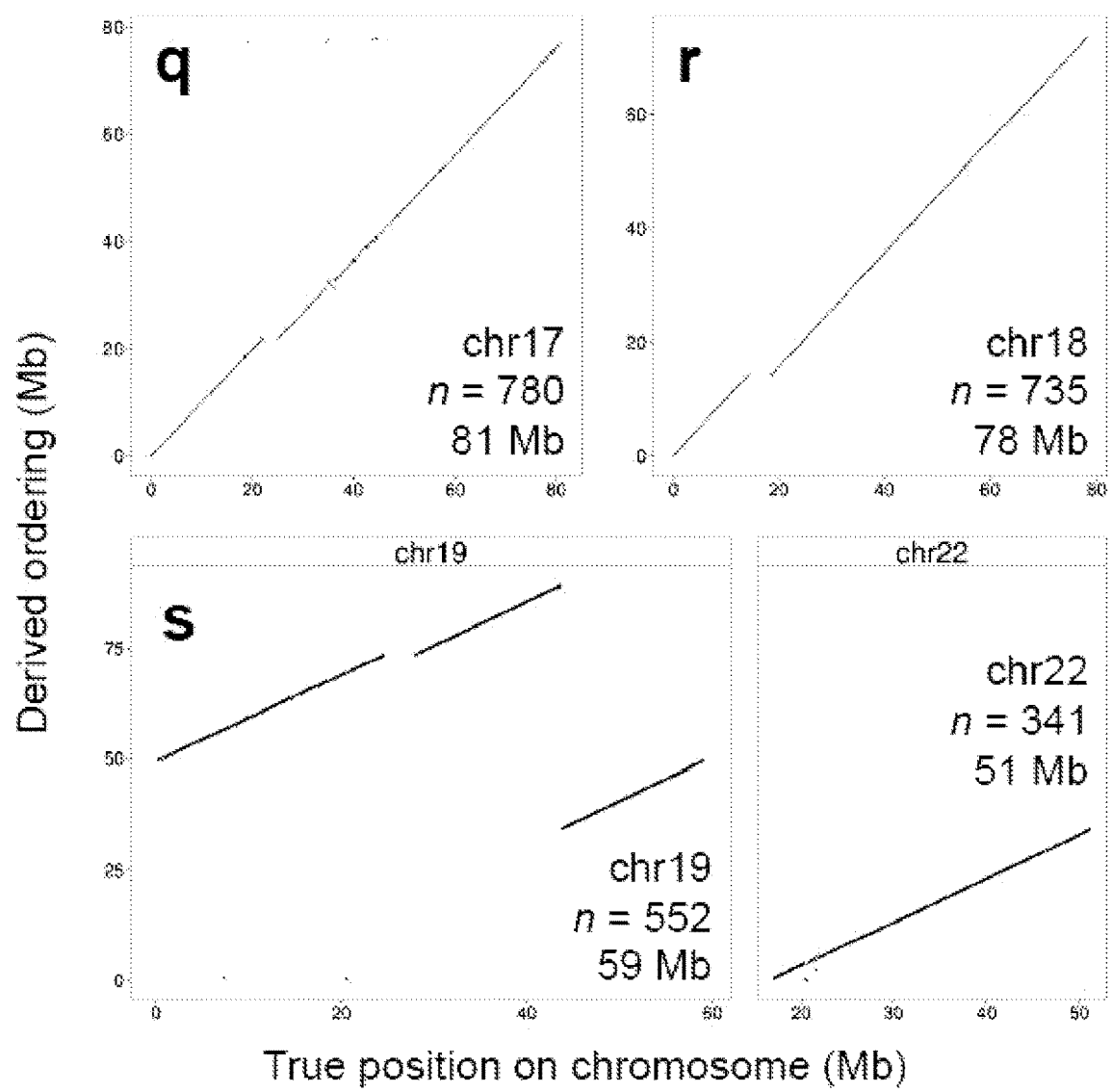
Figure 15:
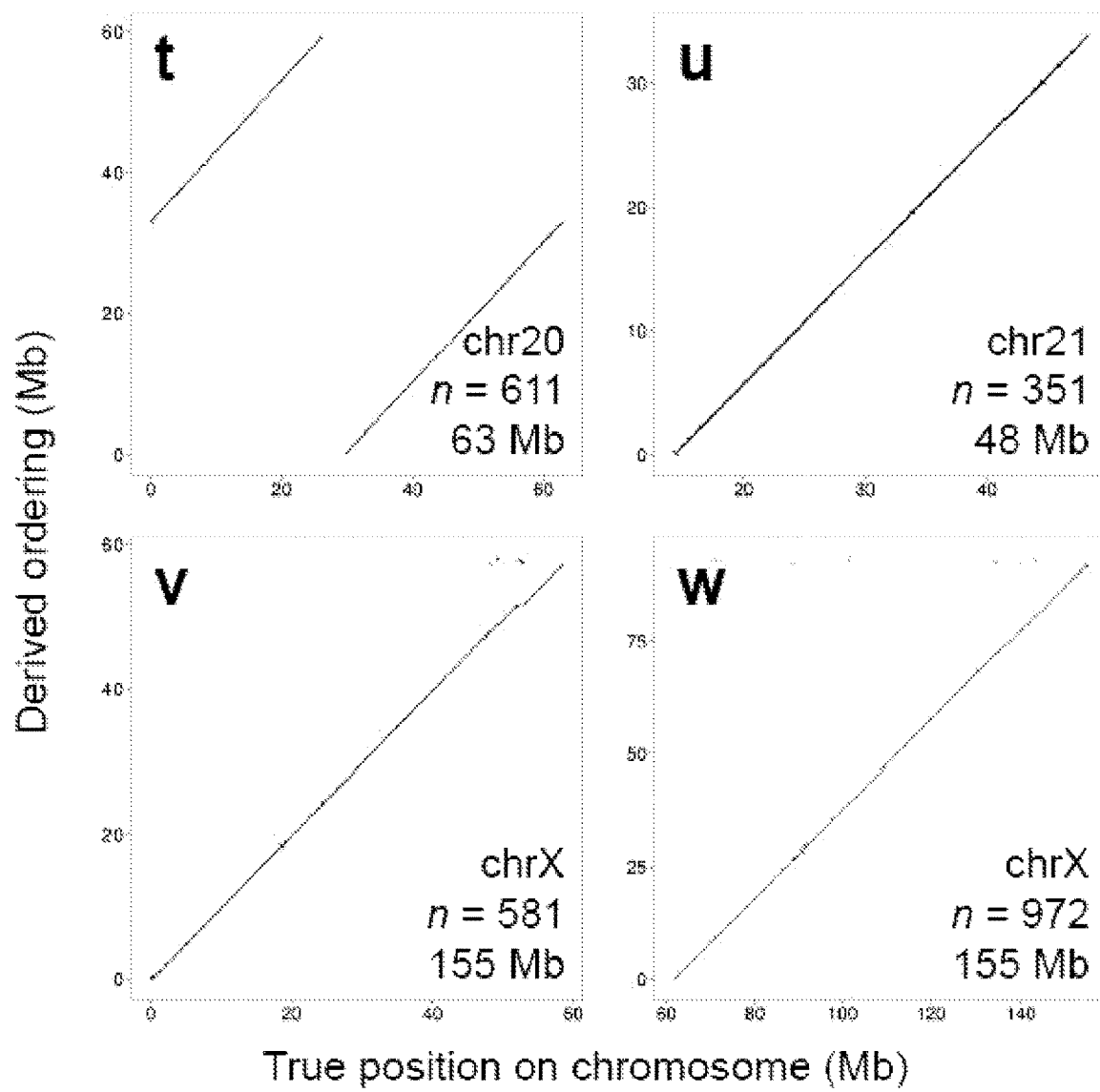

The results for chromosome-scale scaffolding of the human, mouse, and fly genomes were based on initial de novo assemblies with reasonably high N50s, i.e., 68 Kb, 224 Kb, and 437 Kb, respectively. To evaluate the power of this approach as a function of the contiguity of this initial assembly, it was sought to reassemble simulated contigs of varying size derived from the human reference genome (GRCh37). In each iteration, the human reference genome was split into equally sized contigs (10, 20, 50, 100, 200, 500, or 1,000 Kb) and mapped Hi-C read-pairs (Dixon et al. 2012) to these simulated shotgun assemblies. Then, LACHESIS was used to cluster, orient, and order the simulated contigs into chromosome groups (results for 100 Kb simulated contigs are shown in FIGS. 14, 15). As shown in FIG. 39, the performance of the method with respect to completeness and local accuracy is robust above an initial N50 of 50 Kb, but degrades rapidly below this point.

In a separate analysis, the sequencing depth of Hi-C data was down sampled and chromosome-scale scaffolding of the human shotgun assembly (N50=437 Kb) was performed. Although clustering is robust to marked reductions in the amount of Hi-C data, accurate ordering and orienting of scaffolds within chromosome groups requires ~400M read-pairs (FIG. 45). Nonetheless, even the full amount of Hi-C data used here is less than 10% of the amount of sequencing data used to generate the initial shotgun assembly (59 Gb vs. 607 Gb).

Validating or discovering chromosomal rearrangements in cancer genomes. It was also determined that the strong intrachromosomal signal observed in Hi-C data may enable the global discovery or validation of interchromosomal rearrangements in cancer genomes, many of which are challenging to detect with methods other than karyotyping because the breakpoints occur in repetitive regions. For example, recent studies combined several mate-pair sequencing strategies to detect rearranged marker chromosomes in the aneuploid HeLa cancer cell line (Landry et al. 2013; Adey et al. 2013). However, such methods were only successful for a small proportion of rearrangements, and for none of the rearrangements involving centromeric sequences. Of note, the 4C method was previously used to detect chromosomal breakpoints in cancer genomes, but in a targeted rather than global fashion (Simonis et al. 2009).

Figure 16:
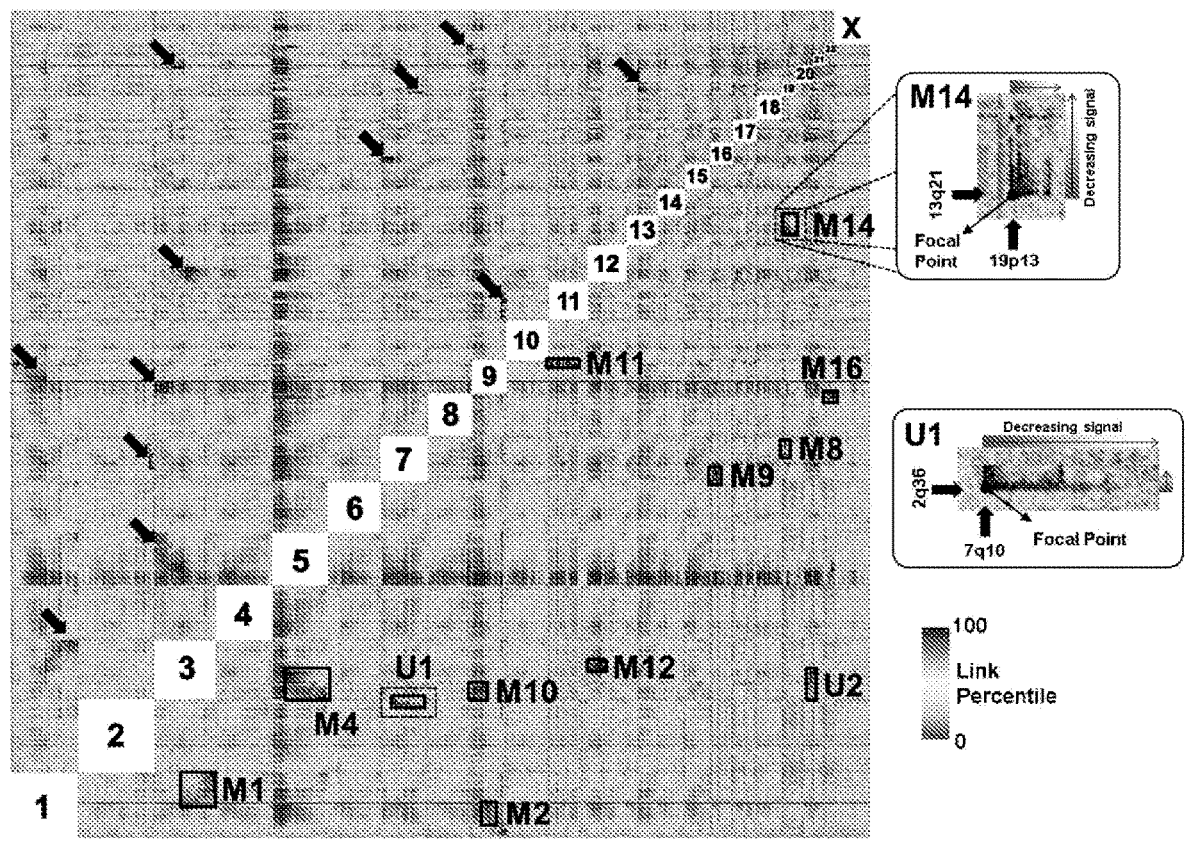
FIG. 16 shows chromosome fusion detection in HeLa S3 using Hi-C data according to some embodiments. Normalized interchromosomal links for a HeLa S3 Hi-C library between megabase windows were derived as described in the methods in the Examples below and are represented as an all-by-all heatmap. For visualization purposes, link weights were ranked and converted to a percentile. Previously identified marker chromosomes were identified (M1, M2, M4, M8, M9, M10, M11, M12, M14, and M16) as well as two additional peaks representing previously undescribed marker chromosomes (U1: der(2;7)(q36;q10) and U2: der (3;20)(q25;q10)). Two rearrangements are highlighted (M14 and U1) to demonstrate the signal focal point at the location of the fusion event with asymmetrical signal decay outward in the direction of the sequence contained in the chromosome fusion, thus allowing breakpoint identification as well as orientation.

To test this, a Hi-C library from HeLa cells was constructed and sequenced to high depth (154 M unique read-pairs). These data were used to generate a matrix of link densities between ~1 Mb windows in the reference human genome. Visual examination of the matrix revealed off-diagonal patches of strong linkage with asymmetric decay, consistent with interchromosomal rearrangements (FIG. 16). Most of these correspond well to previously described marker chromosomes (Macville et al. 1999), although strong evidence for two novel marker chromosomes was also observed (der(2;7)(q36;q10), "U1" and der(3;20)(q25;q10), "U2"). An inclusive rearrangement calling method was implemented that successfully identified all of the suspected marker chromosomes, albeit with limited specificity (FIG. 5). Using chromatin interaction data in this way may enable the validation of candidate chromosomal rearrangements, or the detection of chromosomal rearrangements in heterogeneous cancer cell populations that might not be detected by karyotyping of limited numbers of cells.

Discussion

In the example above, it was demonstrated that genome-wide chromatin interaction datasets such as those generated by Hi-C are a rich source of long-range information for assigning, ordering, and orienting genomic sequences to chromosomes, including across megabase-scale centromere gaps, as well as for validating chromosomal translocations in cancer genomes. There are a number of avenues for the potential improvement of this approach, both experimentally and computationally.

Although the experimental methods for Hi-C are straightforward, current protocols require a large amount of material ($10^6$-$10^8$ cells). As such, reducing the input requirements is an important technical goal. To date, global chromatin interaction datasets have been generated on organisms including yeast (Duan et al. 2010), human (Lieberman-Aiden et al. 2009; Dixon et al. 2012; Yaffe & Tanay 2011), mouse (Dixon et al. 2012), fruit fly (Sexton et al. 2012), and *Arabidopsis thaliana* (Maissiard et al. 2012). This is consistent with broad applicability, but demonstrating these protocols on an even more diverse range of organisms is imperative. On a related point, as the success of this approach depends on chromosomes occupying distinct territories in the nucleus, it will be important to further validate LACHESIS in diverse species to confirm that this is ubiquitously the case. It is also noted that using multiple restriction enzymes (or developing new methods that avoid restriction digestion altogether) will likely improve performance, particularly for smaller contigs or scaffolds. Along the same lines, even if this approach broadly enables chromosome-scale scaffolding, the contiguity required for the initial de novo assembly (~50 Kb) may be challenging to achieve for many organisms. As such, there will remain a strong need for methods delivering "intermediate" contiguity information in a highly cost-effective and scalable manner.

Figure 17:
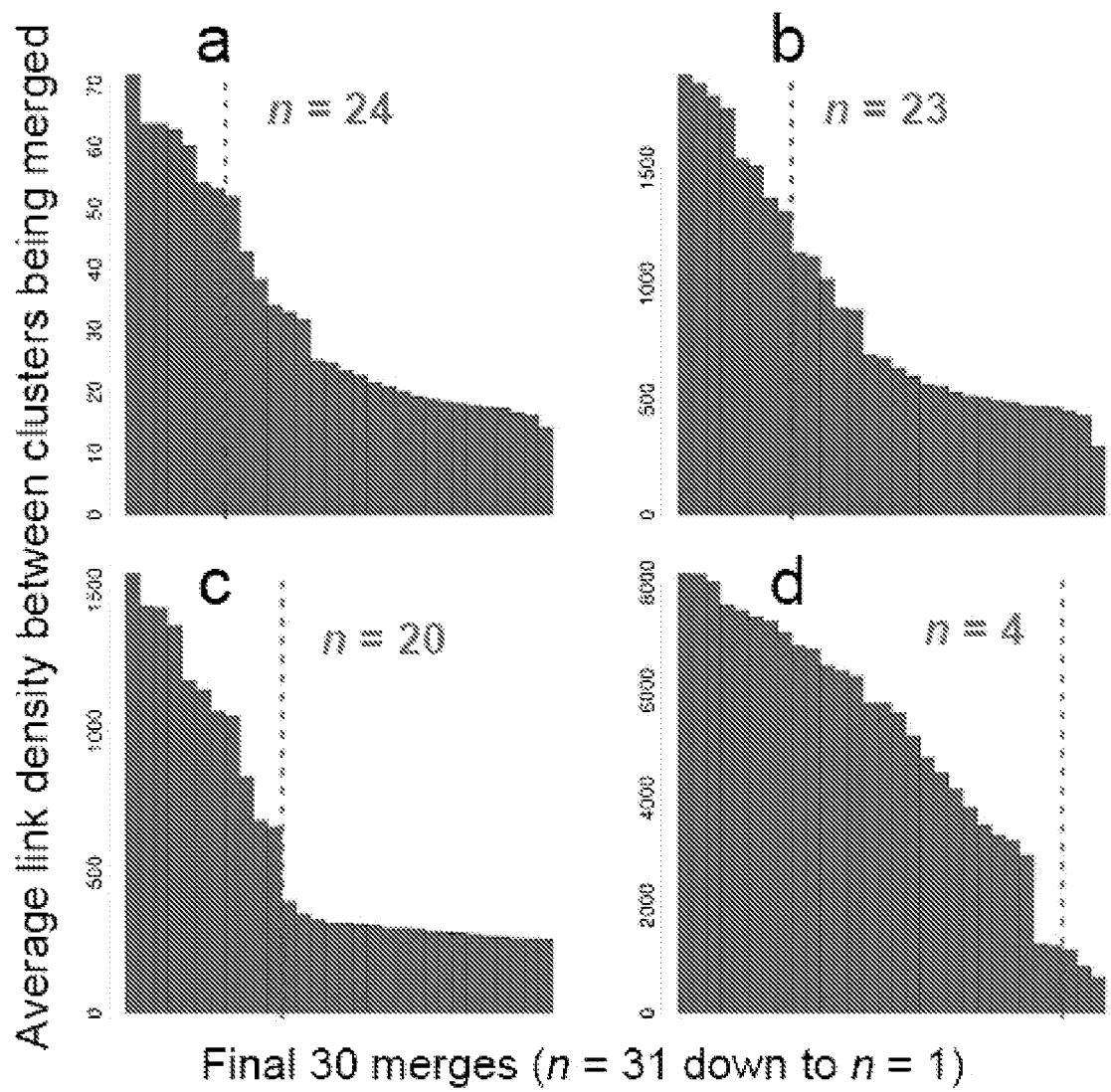
FIG. 17 illustrates the difficulty of calling the number of chromosomes from Hi-C link data alone according to some embodiments. At each step of the LACHESIS clustering algorithm, the two clusters with the highest average link density are found and merged (FIG. 2). x-axis, the final 30 merges; y-axis, average link densities at each merge. The average link density monotonically decreases as merges are made. In practice, merging stops when a predetermined number of clusters is reached (blue line); importantly, this number is determined from a priori knowledge of the chromosome number rather than from the link densities shown here. a. The human simulated assembly with 100-Kb bins. b. The human de novo assembly. Note that the first several merges beyond n=23, corresponding to fusions of the small chromosomes, have fairly high link densities. c. The mouse de novo assembly. d. The *Drosophila* de novo assembly. Note that the link densities imply n=6, corresponding to a split of the arms of fly chromosomes 2 and 3, is a better solution than n=4.

Computationally, the clustering step requires the number of chromosomal groups to be specified a priori. It was assessed whether the scoring metric used during clustering enables reliable inference of chromosome number, but this is not the case (FIG. 17). One potential alternative is to order contigs or scaffolds prior to determining chromosome groups.

Some ordering and orientation errors were associated with short scaffolds, segmental duplications and simple repeats (FIG. 42). It is possible that the full exclusion of ambiguously mapping reads may introduce "gaps" in contiguity information that are increasing the probability of errors in such regions. Alternatively, these errors may be secondary to flaws in the initial shotgun assembly. Consistent with the latter, LACHESIS was also run on a human "shotgun assembly" that has higher contiguity because it used fosmid endpair data (Gnerre et al. 2011) (N50 scaffold length 11.5 Mb vs. 437 Kb). In this case, chromosome-scale scaffolding of this assembly was achieved, but with lower accuracy due to a small fraction of incorrectly joined scaffolds in the input to LACHESIS (FIG. 40). This suggests that conservative de novo assembly prior to using chromatin interaction mapping for long-range scaffolding may be optimal. Lastly, it is noted that the use of chromatin interaction data for long-range scaffolding (via LACHESIS) was entirely separate from the initial assembly of contigs/scaffolds (by ALLPATHS-LG). A more integrated approach might improve accuracy.

Starting from draft human and mouse genome assemblies, each having tens of thousands of scaffolds, nearly all scaffolds were able to be clustered into groups that overwhelmingly corresponded to individual chromosomes. A high fraction of these assignments were correct (comprising >99% of the sum length of clustered scaffolds). Further, contigs within each chromosome group were able to be ordered and oriented, including scaffolding across megabase-scale centromere gaps, with surprisingly few errors. As such, reasonably accurate de novo mammalian genome assemblies with chromosome-scale contiguity were achieved using just three types of libraries, all generated by in vitro methods and sequenced as short read-pairs on a single platform (for human, shotgun fragment (322 Gb); ~2.5 Kb short jump (285 Gb); and Hi-C (59 Gb)). Although its broad applicability beyond the genomes assembled here has still to be demonstrated, this approach may enable next-generation de novo genome assemblies that do not sacrifice the high standards for contiguity set by the HGP.

Example 2

Performing a Lachesis Method Using Computer Software

To create a long-range or ultra-long-range output assembly using the LACHESIS method described in detail above, a software package available at shendurelab.github.io/LACHESIS/ may be used in accordance with certain embodiments described above.

The LACHESIS software may be used to perform the methods described herein as follows.

System Requirements

To setup and run LACHESIS, a computer running in a UNIX environment with at least 16 GB of memory is used, with the following software installed:

gcc, the C++ compiler (gcc.gnu.org/)
The zlib compression library (www.zlib.net/)
The boost C++ libraries (www.boost.org/)
The SAMtools toolkit for handling SAM/BAM files (samtools.sourceforge.net/)

In addition to the aforementioned software, the following software may also be needed:

The short-read aligner BWA (bio-bwa.sourceforge.net/) or another such aligner

The BLAST aligner in command-line form (www.ncbi.nlm.nih.gov/books/NBK1763/)

The bedtools toolkit for handling genomic intervals (code.google.com/p/bedtools/)

Next, the LACHESIS package may be downloaded from shendurelab.github.io/LACHESIS/ into a UNIX filesystem. If the tarball (LACHESIS.tar.gz) is downloaded, unpack it using the following UNIX commands:

```
tar xzvf LACHESIS.tar.gz
cd LACHESIS/
```

Next, the LACHESIS package is compiled. To compile LACHESIS, two other libraries are first downloaded and installed: boost (available at http://www.boost.org/) and SAMtools (available at http://samtools.sourceforge.net/). Once these are installed, set the shell environment variables $LACHESIS_BOOST_DIR and $LACHESIS_SAMTOOLS_DIR to point to the directories containing these packages. The command for setting an environment variable will depend on what Unix shell is being used. Then, to compile LACHESIS, type the word make in the main LACHESIS directory.

Running Lachesis

Figure 18:
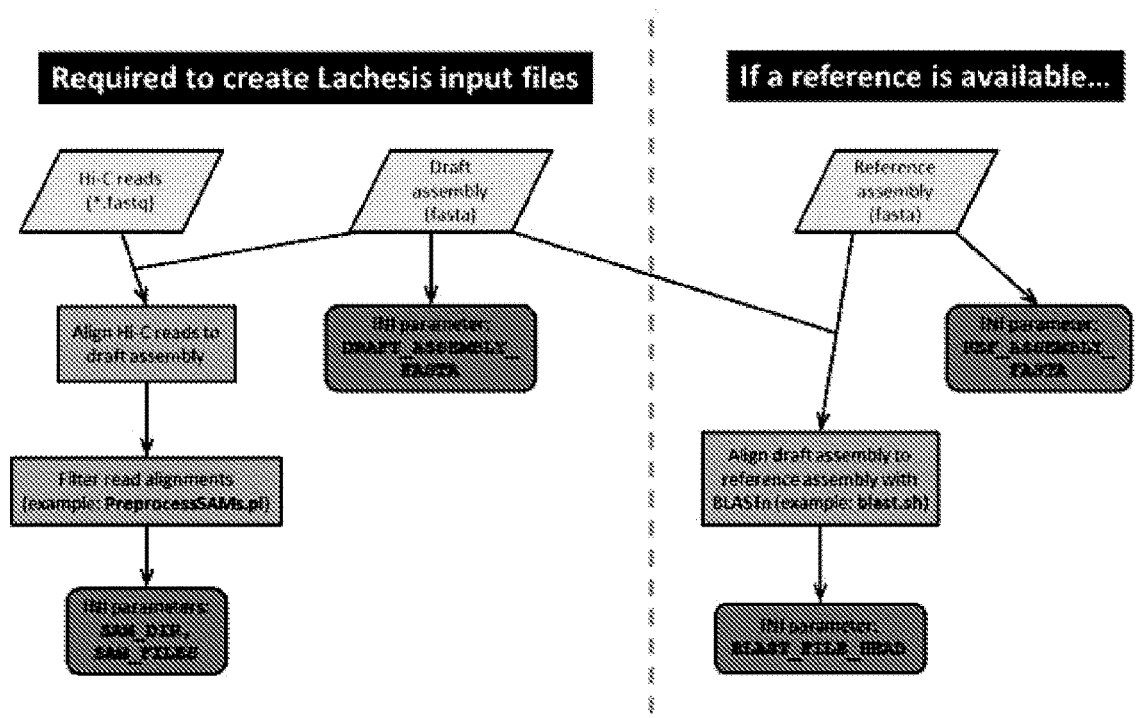
FIG. 18 is a schematic illustrating input file (Hi-C reads in *.fastq, draft assembly in fasta, and if available, a reference assembly in fasta) processing to create INI files according to some embodiments.

Input requirements. To scaffold a de novo assembly using the aforementioned software package to run the LACHESIS method, two or 3 input files are used: (1) a file that contains a set of Hi-C reads, in alignable format, (2) a file that contains a draft de novo assembly, in fasta format, and optionally, (3) a file that contains a reference assembly, in fasta format. See FIG. 18. If no reference assembly is available, the LACHESIS method can be used to scaffold a de novo assembly without a reference assembly, as detailed below. If a reference assembly exists (including a full reference assembly, a partial reference assembly, or a reference assembly of a related species), said reference assembly can be used as an input to LACHESIS to provide a useful reference-based evaluation of the result. However, note that LACHESIS is not an ideal piece of software for performing assisted assembly—that is, a semi-de novo assembly process that relies on the assumption of synteny with an existing reference genome. For more information on assisted assembly, see Gnerre et al, 2009.

If BWA is used to align the Hi-C reads, then the reads must be in a set of fastq or BAM files, and there should be two files for each library: one for the first read in each pair, and one for the second. If another aligner is used, the Hi-C reads may be in another format as required by that aligner.

Creating an INI File.

Before running LACHESIS, an initialization file, or INI file (*.ini) should be created. LACHESIS will parse this file and determine everything it needs to know in order to run, including the locations of all other input files. To create an INI file, make a copy of any of the INI files in the subdirectory INIs/ and edit that copy. The INI file contains several parameters; read through its documentation and set all parameters as one sees fit.

Five of the INI parameters describe files that LACHESIS uses: DRAFT_ASSEMBLY_FASTA, SAM_FILES (in SAM_DIR), RE_SITE_SEQ, BLAST_FILE_HEAD, and REF_ASSEMBLY_FASTA. These all refer to files that will need to be created before running LACHESIS, by processing the input datasets. See FIG. 18 for a visual guide to this process.

Many of the other INI parameters provide heuristic parameters. It's worth the time to examine these parameters to get a better idea of what LACHESIS is doing. But if there is any uncertainty regarding any of them, feel free to use the values in INIs/test_case.ini as defaults.

Aligning the Hi-C Reads to the Draft Assembly.

LACHESIS scaffolds de novo assemblies using the locations of the Hi-C reads on the assembly contigs/scaffolds. Hence the Hi-C reads need to be aligned to the assembly contigs/scaffolds. Ultimately, one needs to produce files containing paired-read alignments in the SAM/BAM format (either SAMs or BAMs are acceptable; see samtools.sourceforge.net/). For each library of Hi-C reads (represented by a pair of fastq files) a single SAM/BAM file describing the read pairs should be created. However, a pair of SAM/BAM files should not be created (i.e., one for each read in the pair).

Aligning is a computationally intensive process and takes far more CPU time than LACHESIS itself. Any aligner that produces SAM or BAM files may be used, but because BWA (bio-bwa.sourceforge.net/), was used during the development of LACHESIS, BWA is a good choice. If BWA is used, the Hi-C reads need to be in fastq format as described above, and the following steps will need to be performed:

Use bwa index to index the draft assembly. If the genome is large (>10 Mb), the flag -a bwtsw should be used. This will create a file <assembly>.fasta.bwt Use bwa aln to align the Hi-C reads to the indexed assembly. Each individual fastq file is aligned separately.

Use bwa sampe to determine the optimal placement of each read pair. This is where the two fastq files from each library are combined. The output of bwa sampe will be a SAM file (*.sam). This file can be compressed to a BAM file (*.bam) using samtools (samtools view -bs <sam-file>) which will use less disk space and less I/O time.

Filtering the Hi-C Reads.

Many of the Hi-C reads can be determined to be noise, rather than signal. It is not strictly necessary to remove these reads from the BAM files before running LACHESIS. But it will reduce the files' size, reduce the I/O time required by LACHESIS to read them in, and may reduce LACHESIS' error rate.

We have included the scripts PreprocessSAMs.pl and PreprocessSAMs.sh, which perform the filtering methods we used. PreprocessSAMs.pl removes all reads that do not map within 500 bp of a restriction enzyme site, following the suggestion of Yaffe & Tanay (Nature Genetics, 2011). To do this, it uses the script make_BED_around_RE_site.pl (also included) and also the bedtools library. PreprocessSAMs.pl also removes unpaired reads, which LACHESIS cannot use. Make sure to set the variable $RE_site in PreprocessSAMs.pl. The script PreprocessSAMs.sh may also be used as a batch script to run PreprocessSAMs.pl on a set of SAM/BAM files (set the variables SAMs and ASSEMBLY). The final set of SAM/BAM files is specified in the INI file as the parameter SAM_FILES, which names the files, and SAM_DIR, which names the directory they are in.

Aligning the Draft Assembly to the Reference Assembly, if there is One. This step may be skipped if no reference assembly is used. LACHESIS needs to know where the contigs/scaffolds from the draft assembly belong on the reference chromosomes. It can process the text output from the blastn command-line program, which is described and can be downloaded at www.ncbi.nlm.nih.gov/books/NBK1763/. To do this, perform the following steps:

Create a BLAST database for the reference assembly: makeblastdb -in <ref-fasta>-dbtype=nucl -out <ref-fasta>.blastdb Run blastn. Make sure the argument 'outfmt -7' is used so that blastn produces output in the format that LACHESIS expects.

If a large (mammalian-scale) draft assembly is used, blastn will take a long time to align it. Such a large draft assembly may be split up into separate fasta files and run blastn on each file separately. To see how this was done on the human assembly, see the included scripts blast.sh and blast.qsub.sh and the output files in test_case/draft_assembly/. The blastn output files from each chunk should be named <BLAST_FILE_HEAD>.NNN.blast.out, where NNN=1, 2, 3, . . . .

The blastn output file(s) are specified in the INI file by the parameter BLAST_FILE_HEAD. Note that LACHESIS parses the BLAST output the first time it runs, then creates a cached file so that it doesn't have to take the time to parse the BLAST output again. This means that if the set of BLAST files is changed, the file at <OUTPUT_DIR>/cached_data/TrueMapping.assembly.txt needs to be deleted in order to get LACHESIS to load the new set of BLAST files.

Running LACHESIS.

If steps 2-5 above are completed, and an INI file with the appropriate input file names has been created, everything should be ready to go. Try running LACHESIS with the command: Lachesis <your-INI-file>. If there are any problems with the INI file, including missing input files, LACHESIS will immediately abort and will explain what went wrong. If not, then LACHESIS will begin loading in files, and all that needs to be done is wait and see what it does.

There are many parameters in the INI file beyond the inputs to LACHESIS. Some of these parameters may need to be tweaked in order to get an optimal assembly. Be sure to read the documentation in the INI file carefully.

Interpreting the LACHESIS Results.

LACHESIS will create a set of output files in the directory OUTPUT_DIR that have been specified in the INI file. This directory contains a file REPORT.txt that will give a topline summary of LACHESIS' performance. It also contains two subdirectories, main_results/ and cached_data/. The main_results/directory will contain the following files:

1. clusters.txt and clusters.by_name.txt: These files indicate the clustering results. Each of LACHESIS' chromosome group is shown as a line, and the input contigs/scaffolds in that group are listed on the line, either by ID clusters.txt) or by contig name (clusters.by_name.txt).
2. group*.ordering: These files indicate the ordering and orienting results. There is one file for each group. In each file is a list of input contigs/scaffolds in order, with their orientations, orientation quality scores, and gap sizes.

To create the final assembly fasta, run the included script CreateScaffoldedFasta.pl. After this has been run, OUTPUT_DIR will contain the file Lachesis_assembly.fasta. This fasta file will contain the output assembly, in three sections of successive contigs:

1. One large scaffold for each of the ordered and oriented chromosome groups predicted by LACHESIS (i.e., each of the group*.ordering files.)
2. All of the input contigs/scaffolds that have been clustered into a chromosome group by LACHESIS, but were not ordered within that group. They will be given names indicating what chromosome group they belong in.
3. All of the input contigs/scaffolds that were not clustered at all by LACHESIS.

Example 3

Species-Level Deconvolution of Metagenome Assemblies with Hi-C-Based Contact Probability Maps All ecosystems on this planet include communities of microbial organisms (Howe et al. 2014, Xin, Glawe, and Doty 2009, Hug et al. 2013, Venter et al. 2004, Renouf, Claisse, and Lonvaud-Funel 2007), including our own bodies (Qin et al. 2010, Huttenhower et al. 2012). However, our understanding of microbial communities is limited by the ability to discern which microbial taxa they contain and how these taxa contribute to community-scale phenotypes. Most microbial taxa cannot be cultured independently of their native communities (Rinke et al. 2013) and therefore are not readily isolated for individual analysis, e.g., by genome sequencing. Such unculturable taxa may be difficult to study even if they are abundant (Iverson et al. 2012). Consequently, many analyses of microbial communities must treat them as a single sample, for example by shotgun sequencing of a metagenome (Iverson et al. 2012, Huttenhower et al. 2012, Venter et al. 2004, Howe et al. 2014) or metatranscriptome (Frias-Lopez et al. 2008, David et al. 2014).

A central challenge in analyzing a metagenome involves determining which sequence reads and/or sequence contigs originated from the same taxon (Carr, Shen-Orr, and Borenstein 2013). Many computational methods have been developed to deconvolute metagenomic assemblies by mapping reads or contigs to assembled microbial genomes (Wood and Salzberg 2014) or by analyzing base composition (Saeed, Tang, and Halgamuge 2012) or gene abundance (Hug et al. 2013, Carr, Shen-Orr, and Borenstein 2013). However, these strategies are handicapped by the remarkable variety of unculturable species in virtually all microbial communities and the fact that most of these species have not yet been sequenced in isolation (Howe et al. 2014). Individual microbial genomes have been deconvoluted from shotgun metagenome reads using methods such as mate-pair libraries (Iverson et al. 2012, Mitra et al. 2013), lineage-specific probes (Narasingarao et al. 2012), single-cell sequencing (Rinke et al. 2013), neural networks (Dick et al. 2009, Hug et al. 2013, Sharon et al. 2013), and differential coverage binning (Sharon et al. 2013, Albertsen et al. 2013). Some de novo assembly software has also been adapted to anticipate metagenomic shotgun sequence data (Peng et al. 2012, Namiki et al. 2012). These methods have succeeded in isolating whole genomes from abundant organisms in some communities, but they are specific to the communities for which they have been devised and often require prior knowledge of the community's composition (Iverson et al. 2012). Metagenomic analyses would benefit greatly from a more generalizable methodology that can identify the sequence content belonging to each taxon without any a priori knowledge of the genomes of these organisms, especially the genomes of low-abundance taxa. Related to the challenge of determining which contigs belong to the same species are the problems of how to further define and assemble the one or multiple chromosomes that comprise each species' genome, and how to define and assign plasmid content to one or multiple species.

To enable robust reconstruction of individual genomes from within a complex microbial community, additional information beyond standard shotgun sequencing libraries is needed. To that end contact probability maps generated through chromosome conformation capture methods (Dekker, Marti-Renom, and Mirny 2013) were generated and used in a novel way to inform the species-level deconvolution of metagenome assemblies, as described in detail in the Examples below. In one embodiment, Hi-C may be used. Hi-C uses proximity ligation and massively parallel sequencing to generate paired-end sequence reads that capture three-dimensional genomic interactions within a cell (Lieberman-Aiden et al. 2009). As described in the Examples above, the distance dependence of intrachromosomal interactions in Hi-C datasets was exploited to facilitate chromosome-scale de novo assembly of complex genomes. Further, because crosslinking occurs prior to cell lysis in the Hi-C protocol, each Hi-C interaction involves a pair of reads originating from within the same cell. In the context of heterogeneous cell populations (e.g., microbial communities), such pairings may inform the clustering of genome sequences originating from the same species. In addition, because the efficacy of the Hi-C protocol has been demonstrated in bacteria (Umbarger et al. 2011, Le et al. 2013), the methods described herein may also be used to inform the clustering of genome sequences originating from metagenome samples containing both prokaryotic and eukaryotic cells.

Figure 19:
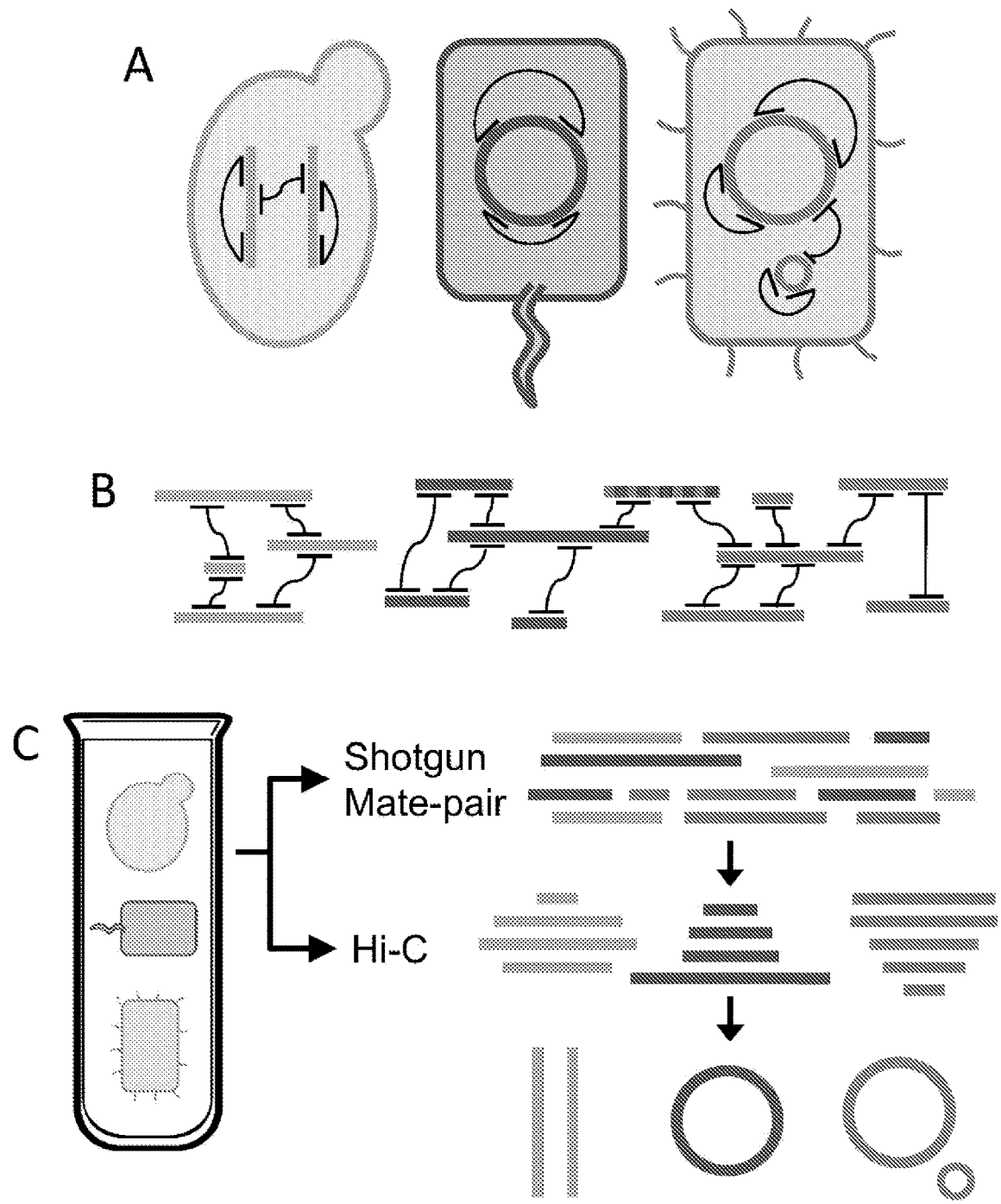
FIG. 19 is an overview of MetaPhase methodology according to some embodiments. (A) Performing Hi-C on a mixed cell population. Shown are three microbial cells of different species (green, red, blue) with their genomes (thick colored lines or circles), which may or may not include multiple chromosomes or plasmids. A Hi-C library is prepared and sequenced from this sample. The Hi-C read pairs from this library (black lines) represent pairs of sequences that necessarily occur within the same cell. (B) Using Hi-C reads to deconvolute individual species' genomes. A shotgun sequencing library from the same sample is used to create a draft de novo metagenome assembly, which contains contigs from all species (thick lines). The Hi-C reads are then aligned to this assembly. Because sequences connected by Hi-C links must appear in the same species, the contigs form clusters representing each species. Note that some sequences (e.g., blue/red dotted line) may appear in multiple species, confounding the clustering. (C) MetaPhase workflow. A single metagenome sample is used to create shotgun, Hi-C, and (optionally) mate-pair libraries, which are used together to create individual species assemblies.

Here experimental proof of concept for this strategy is provided in several contexts, while also describing an algorithm for this task, MetaPhase (FIG. 19). The genomes of as many as 18 species were reconstructed from a single synthetic mixture of eukaryotes and/or prokaryotes, including some species with as much as 90% sequence identity to one another, and high-contiguity de novo assemblies were generated for individual eukaryotic species present within the synthetic microbial community. In the process, the first demonstration of Hi-C in an archaeal species was also shown.

Materials and Methods

Sample collection: Cultures of individual strains listed in FIG. 46 (M-Y) and FIG. 47 (M-3D) were grown to saturation in rich media (YPD for yeasts, LB for bacteria, McCas media for *M. maripaludis*, PMsul media for *R. palustris*). Culture densities were measured by spectrophotometry and FACS. After mixing the strains, cultures were diluted with YPD media (M-Y) or with LB media (M-3D) to a final OD600 of 1.0 in a final volume of 500 mL. Formaldehyde was added to a final concentration of 1% and cultures were incubated at room temperature for 30 minutes. To quench the crosslinker, 5 grams of glycine was added to each 500 mL culture and the cultures were incubated for 30 minutes at room temperature. Cultures were centrifuged to pellet all cells. Cell pellets were frozen at −20° C. until further processing.

Shotgun and Mate-Pair libraries: Total DNA was isolated from cultures using a standard phenol/chloroform glass bead purification followed by ethanol precipitation and subsequent cleanup using the DNA Clean and Concentrator-5 Kit (Zymo Research). Shotgun libraries were prepared using the Nextera DNA Sample Preparation Kit (Illumina). Mate-pair libraries were constructed using the Nextera Mate Pair Sample Preparation Kit (Illumina).

Hi-C libraries: Cell pellets (~100 μL volume each) were resuspended in 2 mL of 1×TBS buffer containing 1% Triton-X and Protease Inhibitors (Roche, cOmplete, EDTA-free) and split equally into 2 separate 2 mL tubes. 300-500 μL of 0.5 mm diameter glass beads were added to each tube and tubes were vortexed on the highest setting in four 5 minute increments, each separated by 2 minute incubations on ice. Lysate was transferred to fresh tubes. Crosslinked chromatin was recovered by centrifugation at 13 KRPM in an accuSpin Micro17 centrifuge (Fisher) and rinsed with 1×TBS buffer. Chromatin from each tube was digested overnight with 100 units of either HindIII or NcoI restriction endonuclease (NEB) at 37° C. in a total volume of 200 μL. To enrich for long-range interactions (M-3D library only), digested chromatin was centrifuged for 10 minutes at 13 KRPM, rinsed in 200 μL of 1×NEBuffer 2 (NEB), centrifuged again and resuspended in 200 μL of 1×NEBuffer 2 (NEB). Restriction fragment overhangs were filled in using biotinylated dCTP (Invitrogen) and Klenow (NEB) as described (van Berkum et al. 2010). DNA concentration within the chromatin suspension was quantitated using the QuBit fluorometer (Invitrogen) and for each sample an 8 mL ligation reaction was set up at final DNA concentration of 0.5 ng/μL using T4 DNA Ligase (NEB). Ligation reactions were incubated at room temperature for 4 hours and then overnight at 70° C. to reverse crosslinks. DNA was purified using a standard phenol/chloroform purification followed by ethanol precipitation and resuspended in 600 μL of water with 1×NEBuffer 2 (NEB) and 1×BSA (NEB). To remove biotin from unligated DNA ends, 20 units of T4 Polymerase (NEB) were added to each 600 μL DNA sample and incubated at 25° C. for 10 minutes followed by 12° C. for 1 hour. DNA was purified using the DNA Clean and Concentrator-5 Kit (Zymo Research). Illumina libraries were constructed as described (van Berkum et al. 2010) using reagents from the Illumina Mate Pair Sample Preparation Kit. Paired-end sequencing was performed using the HiSeq and MiSeq Illumina platforms (Table 2).

Draft metagenome assembly for M-Y and M-3D: To create draft metagenome assemblies for the synthetic samples, the fragment library was assembled using the IDBA-UD assembler (Peng et al. 2012). IDBA-UD was run with the --read option set to the fragment reads and the following additional parameters: '--pre_correction --mink 20--maxk 60--step 10'. The assembly in contig.fa was used rather than scaffold.fa to reduce the risk of false joins made at the scaffolding stage.

Aligning Hi-C reads: The Hi-C reads were aligned to the draft metagenome assembly in a multi-step process. First the reads were aligned using BWA (Li and Durbin 2009) with the option '-n 0', requiring a perfect match of the entire 100-bp read. For read pairs in which an alignment was not found for both reads, the reads were trimmed from 100 bp to 75 bp and were aligned using '-n 0' again. For read pairs in which alignment was still not found for both reads, the reads were trimmed to 50 bp and aligned using '-n 0' again. All read pairs for which no alignment was found were discarded from further analysis. Read pairs were also discarded if the reads did not both align within 500 bp of a restriction site, as recommended by Yaffe & Tanay (Yaffe and Tanay 2011).

Clustering contigs by species: To cluster the contigs of the draft metagenome assembly into individual species, a hybrid clustering algorithm was used. A graph was built, with each node representing one contig, and each edge between nodes having a weight equal to the number of Hi-C read-pairs linking the two contigs, normalized by the number of restriction sites on the contigs. Only the single largest component in the graph was used; the other components, generally comprising isolated contigs containing a small fraction of the total sequence length, were discarded and the contigs were not clustered. Within this component, the Jarvis-Patrick nearest-neighbor clustering algorithm (Jarvis and Patrick 1973) was applied with k=100, removing some edges and reweighting all other edge weights by the frequency of their nodes' shared nearest neighbors. This nearest-neighbor approach accounts for the likely possibility that the clusters representing each species will have different internal densities of Hi-C links, due to species' differing abundances in the sample or differing susceptibility to the cell lysis step of Hi-C. Finally, the nodes were merged together using hierarchical agglomerative clustering with an average-linkage metric (Eisen et al. 1998), which was applied until the number of clusters was reduced to the expected or predicted number of individual species (12 for M-Y, not including *P. pastoris*; 18 for M-3D).

Scaffolding of genomic content within individual clusters: To scaffold the individual species' genomes represented in each cluster of contigs, the Hi-C reads were aligned to these contigs and ran them through the Lachesis software described in the Examples above (Burton et al. 2013) to create chromosome-scale scaffolds. The number of chromosomes in each species (10 for *N. castellii* (Gordon, Byrne, and Wolfe 2011); 7 for *K. wickerhamii* (Belloch et al. 1998); 8 for *S. stipitis* (Jeffries et al. 2007)) was provided as an input to Lachesis.

Validation: To determine the true species identity of the contigs in the draft metagenome assembly, the contigs were aligned to a combined reference genome that included the reference genomes of all strains known to be in the metagenome sample (16 strains for M-Y; 18 species for M-3D). The alignment was performed by BLASTn (Altschul et al. 1990) with the following stringent parameters '-perc_identity 95-evalue 1e-30-word_size 50'. A contig was defined as aligning to a species if any alignment of the contig to the species' reference genome was found; the placement of the alignment was ignored.

Results

Figure 20:
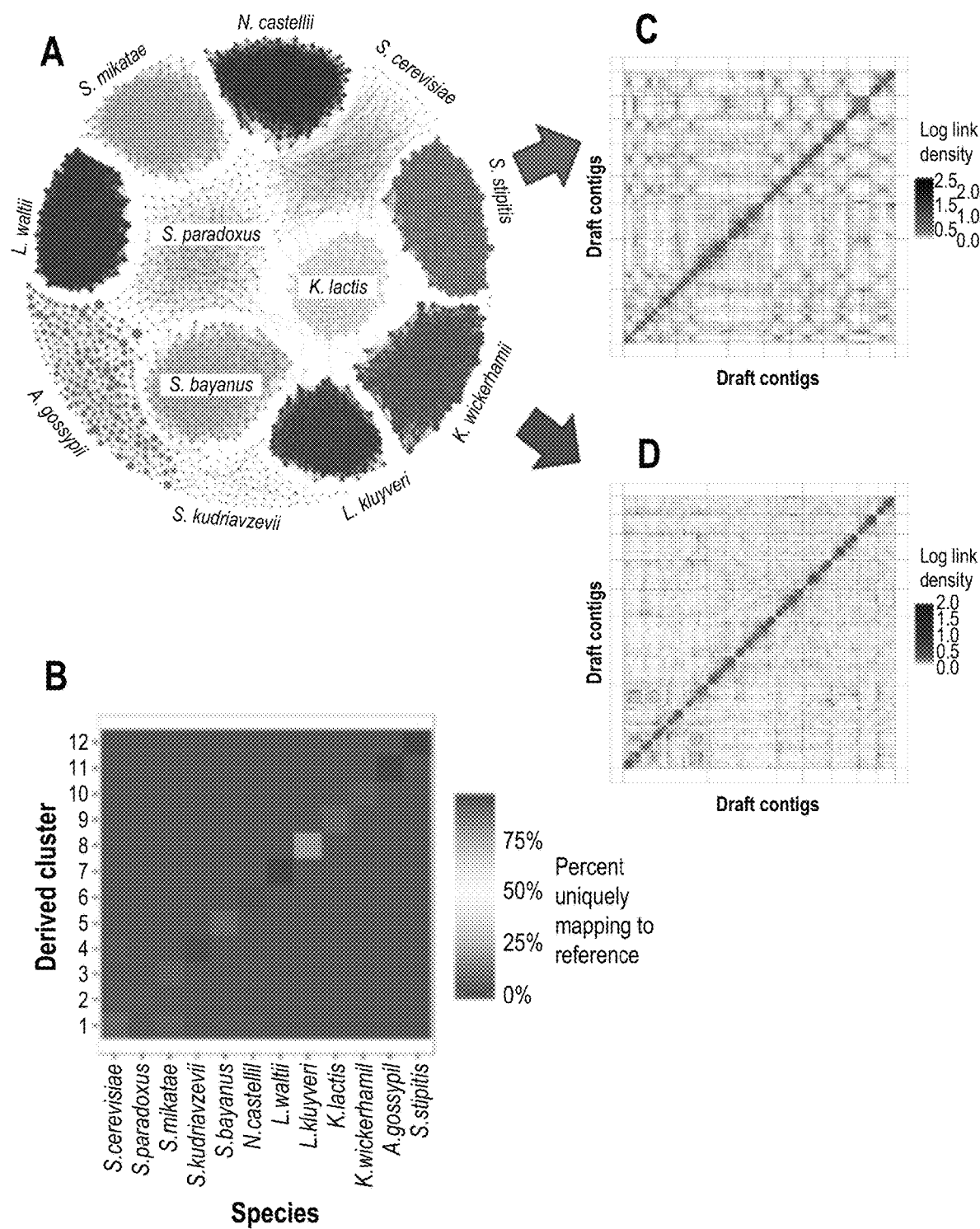
FIG. 20 shows MetaPhase clustering results on the M-Y draft metagenome assembly according to some embodiments. (A) Using Hi-C links to cluster contigs into 12 clusters, one for every species with a substantial presence in the draft assembly. Each contig is shown as a dot, with size indicating contig length, colored by species. Edge widths represent the densities of Hi-C links between the contigs shown. Only 2400 contigs are shown: the 200 largest contigs that map uniquely to each species. (B) Validation. This heatmap indicates what fraction of the sequence in each MetaPhase cluster maps uniquely to each of the reference genomes of the 12 present yeast species. Note that not all sequence is expected to map uniquely to one species. x-axis: the 12 yeast species. y-axis: the MetaPhase clusters. (C,D) Lachesis (Burton et al. 2013) reconstruction of individual species' genomes within the M-Y metagenome assembly. These heatmaps show the Hi-C link density among the contigs in the MetaPhase clusters corresponding to *S. stipitis* (C) and *K. wickerhamii* (D). x,y-axes: the clustering and ordering of contigs by Lachesis. Dotted black lines demarcate chromosomal clusters. Note the expected signals of enrichment within each chromosome and on the main diagonal. The assembly in (C) is similar to the *S. stipitis* reference genome (FIG. 27), while the assembly in (D) has far higher chromosome-scale contiguity than the best available *K. wickerhamii* reference (Baker, Tuch, and Johnson 2011).

Deconvoluting yeast genomes from a synthetic mixture: To evaluate the effectiveness of the proposed strategy, it was first applied to a sample of defined, exclusively eukaryotic composition. Specifically, as shown in Table 1 below, synthetic metagenome samples having sixteen yeast strains ("M-Y"; FIG. 20, Table 1) were created.

TABLE 1

Contents of the Metagenome samples analyzed

| Acronym | Description | No. of Species | Species |
| --- | --- | --- | --- |
| M-Y | Mixture of Yeasts | 16 | *S. cerevisiae*, other *Saccharomyces*; *Lachancea*, *Kluyveromyces*, etc. (see FIG. 46) |
| M-3D | Mixture of 3 Domains | 18 | 8 yeasts (Dikarya); 9 bacteria; 1 archaeon (see FIG. 47) |

Figure 21:
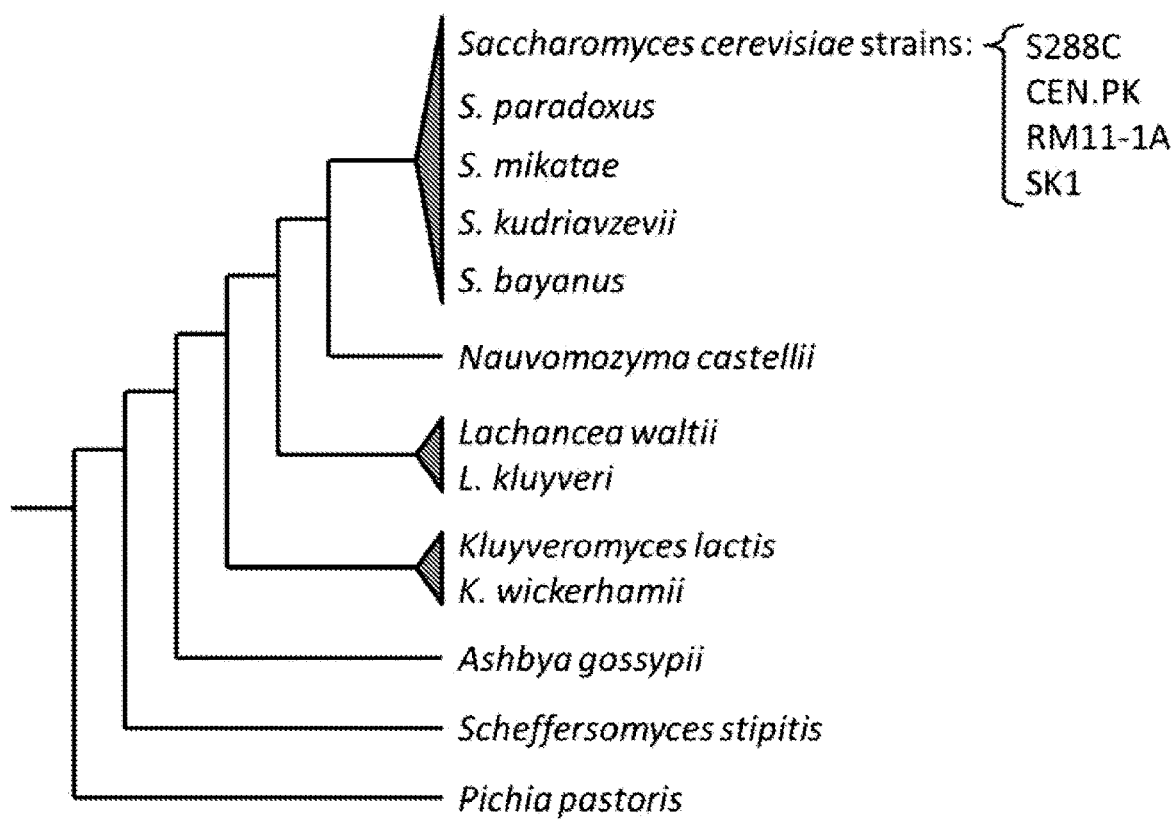
FIG. 21 shows M-Y species phylogeny according to some embodiments. Phylogenetic tree of the 16 Ascomycetes yeast strains used in the M-Y sample (FIG. 46).
Figure 22:
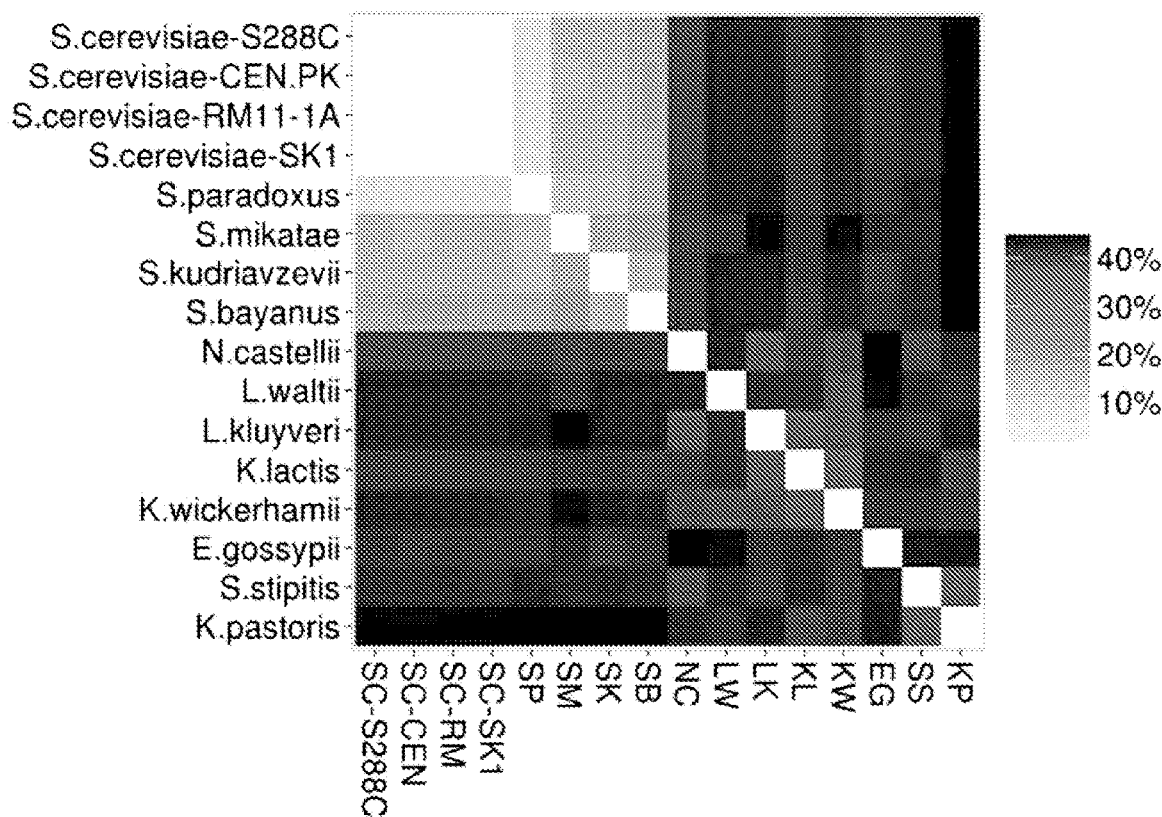
FIG. 22 shows M-Y sequence divergences between species according to some embodiments. Divergence rates were calculated as follows: First, a set of essential ORFs in the *Saccharomyces cerevisiae* genome was downloaded from the Yeast Deletion Website. For each essential ORF, orthologous sequences in every other species were found via BLASTn alignment (Altschul et al. 1990), and these sequences were all aligned together using Clustal Omega (Sievers et al. 2011). Pairwise divergences were calculated by counting the frequency of mismatches among aligned base pairs in the Clustal Omega alignments. This analysis was repeated using essential ORFs from *K. lactis* instead of *S. cerevisiae*, with very similar results (data not shown).

The strains for the M-Y sample include four strains of *Saccharomyces cerevisiae* as well as twelve other species of Ascomycetes at varying genetic distances from *S. cerevisiae*, all of which have publicly available reference genomes (FIG. 46; FIGS. 21, 22) These strains were grown individually to saturation in YPD medium and mixed in roughly similar proportions (with the exceptions of *S. kudriavzevii* and *P. pastoris*, which were mixed in at a much lower proportion to test the sensitivity of this approach). The mixed cell culture was treated with the cross-linking agent, formaldehyde, immediately after mixing the individual strains. Total DNA was isolated from the mixed population culture and prepared for sequencing. This resulted in 92.1 M Illumina read pairs from one shotgun library, 9.2 M Illumina read pairs from one mate-pair library, and 81.0 M read pairs from one Hi-C library (Table 2).

TABLE 2

Sequencing Libraries used in Metaphase Analyses

| Sample | Library type | Read length, bp | Read pairs, millions |
| --- | --- | --- | --- |
| M-Y | Shotgun | 101 | 85.7 |
| M-Y | Mate-pair | 100 | 9.2 |
| M-Y | Hi-C | 100 | 81.0 |
| M-3D | Hi-C | 101 | 14.3 |

Figure 23:
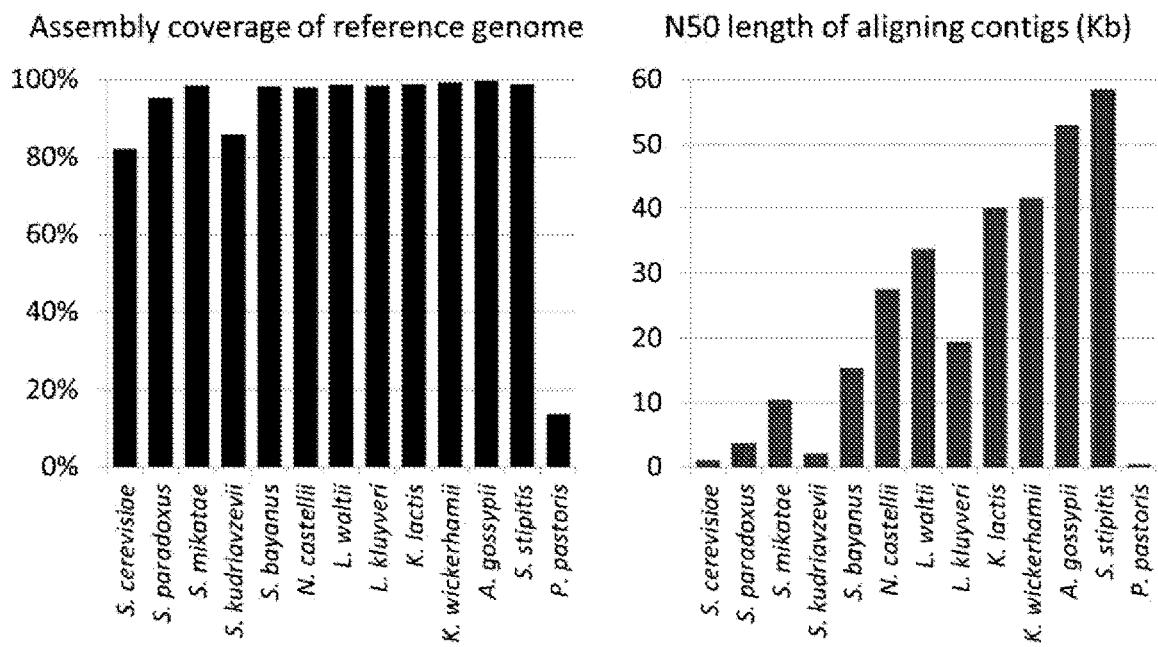
FIG. 23 shows coverage of M-Y reference genomes by draft metagenome assembly according to some embodiments. Contigs from the M-Y draft metagenome assembly were aligned to the reference genomes of each species with BLASTn (Altschul et al. 1990) using the following parameters: '-perc_identity 95-evalue 1e-30 -word_size 50'. The restrictiveness of these parameters ensured that all alignments generated were greater than 70 bp. Left: The fraction of each reference genome covered by BLASTn alignments. Right: For each reference genome, the N50 length of draft contigs aligning to that genome.

The shotgun and mate-pair (~4 Kb) read pairs were used to generate a draft de novo metagenome assembly using IDBA-UD (Peng et al. 2012) (see Methods). This assembly had 48,511 contigs with a total length of 136 Mb and an N50 contig length of 17.3 Kb. Contigs from this assembly covered most of the reference genomes of all 13 yeast species present (average=96.0%), with the exception of *P. pastoris* (13.7%), which also had a very low fraction of shotgun reads aligning to it (1.2%), confirming its low abundance in the sample (FIG. 23).

Figure 24:
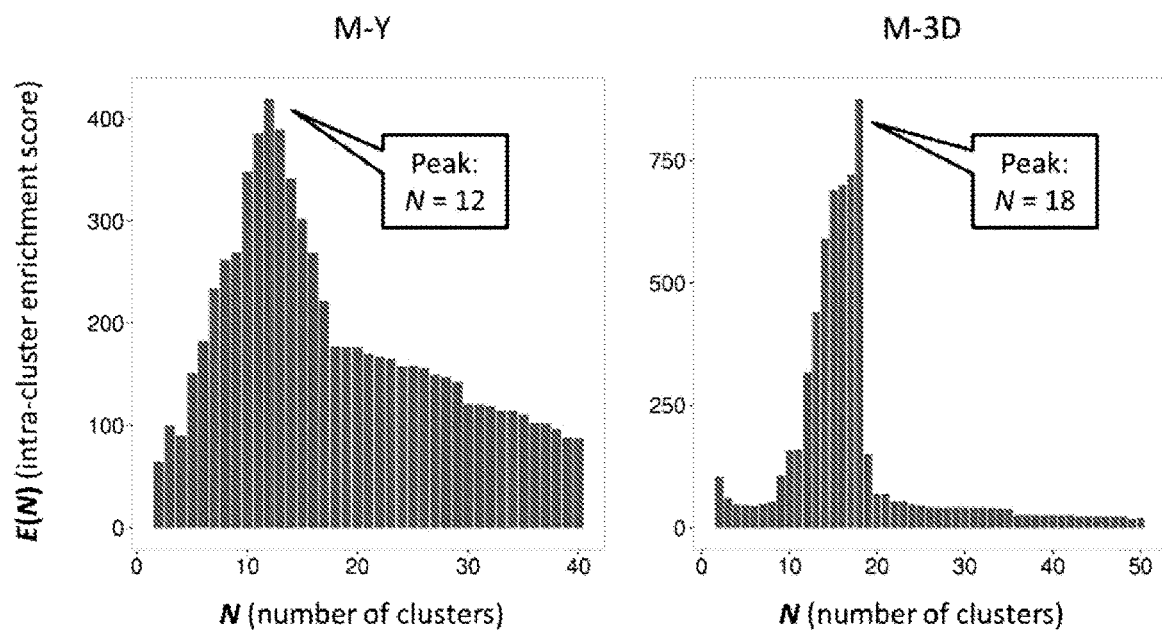
FIG. 24 shows intra-cluster link enrichment as a function of cluster number in M-Y and M-3D according to some embodiments. The hierarchical agglomerative clustering algorithm was run on the M-Y and M-3D datasets. In this algorithm, the number of clusters gradually decreases as clusters are merged together; to generate this data, clustering was continued all the way down to N=1. Shown is the metric E, or intra-cluster link enrichment, at each value of N. Note that for both M-Y and M-3D the maximum value of E(N) occurs when N is equal to the true number of distinct species present in the draft assembly.
Figure 25:
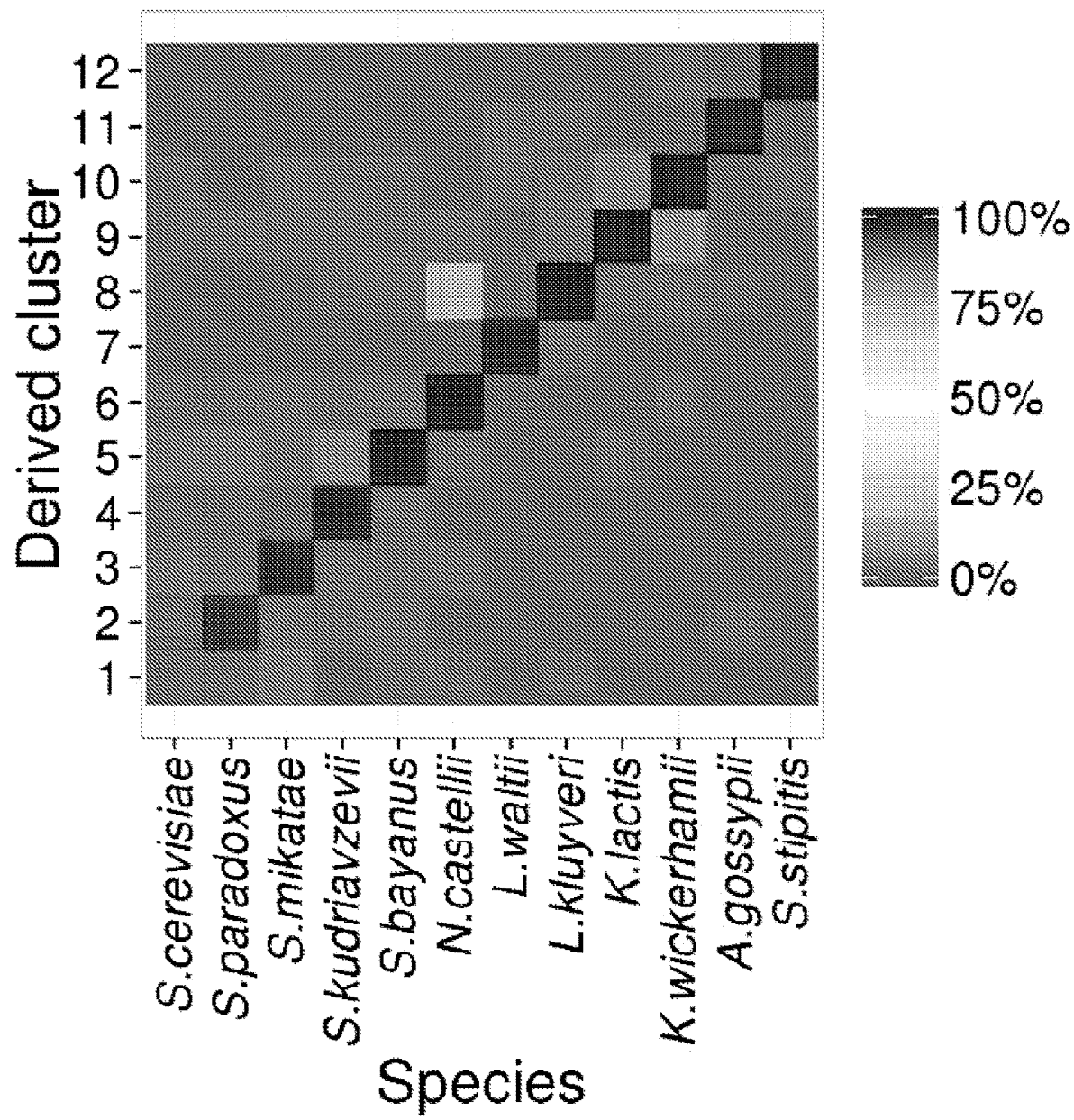
FIG. 25 is a heatmap of non-unique reference alignments of contigs in each M-Y cluster according to some embodiments. This is identical to FIG. 20B, except that all contig alignments to all genomes are shown here, whereas in FIG. 20B only contigs that align uniquely to a single reference genome are shown.

Next, the Hi-C read pairs were aligned to the M-Y metagenome assembly, yielding a network of contigs joined by Hi-C links (FIG. 20A). Then, exploiting the fact that sequences connected by Hi-C links are overwhelmingly expected to derive from the same cell, the links were used to cluster these contigs, applying a novel algorithm that combines the steps of Jarvis-Patrick clustering (Jarvis and Patrick 1973) and agglomerative hierarchical clustering (Eisen et al. 1998) (see Methods). This algorithm suggested the presence of 12 distinct clusters in the sample, based on the metric of intra-cluster link enrichment (FIG. 24). It clustered the majority of the metagenome assembly (111 Mb or 82.2% of total sequence length) into these 12 clusters. Of the remaining 24.1 Mb of sequence not clustered, the vast majority (99.7%) belonged to contigs that contained no HindIII sites and thus are not expected to produce a Hi-C signal in this experiment. Bootstrapping tests confirmed the robustness of the clustering method described above (FIG. 48). The 12 clusters match up closely with the 12 distinct species present in the draft assembly (excluding *P. pastoris*), and 99.2% of sequence was placed into the cluster representing a species to which it truly belongs (FIG. 20B, FIG. 25), allowing for the possibility of a given contig belonging to multiple species.

Figure 26:
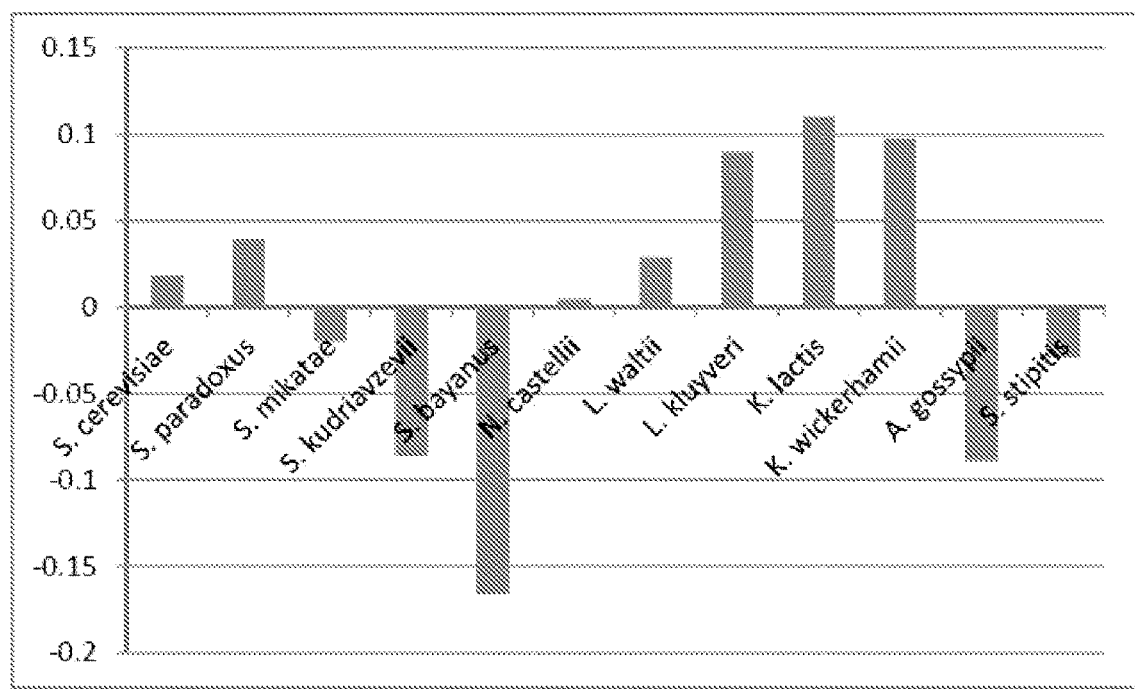
FIG. 26 shows differential Hi-C efficiency rates by species for the M-Y sample according to some embodiments. For each species, the Hi-C efficiency rate was calculated as $$E_{species} = \frac{f_{species}(Hi-C)}{f_{species}(\text{shotgun})},$$

Further analysis of the clusters demonstrated several strengths and limitations of the method described above. Some species had greater Hi-C link densities than others, after correcting for differences in species abundances (FIG. 26). This suggests that some species' cells are more susceptible to lysis during Hi-C than others', and MetaPhase is robust to these differences. However, distantly related species proved easier to separate than closely related species. For example, in the cluster representing *Scheffersomyces stipitis*, 99.88% of the contigs (by length) matched the *S. stipitis* reference genome, whereas in the cluster representing *S. cerevisiae*, 3.3% of the contigs (by length) instead aligned uniquely to the genome of closely related *S. mikatae*. It was also noted that the sequence content in the *S. cerevisiae* cluster included the contigs that aligned to any of the four *S. cerevisiae* strains' reference genomes. This indicates that, although this method is generally successful in merging closely related strains of the same species into a single cluster, genetic variation between strains causes fragmentation of the species' sequence contigs in the metagenome assembly (FIG. 23), which in turn hampers the ability to delineate this cluster correctly because smaller contigs produce a weaker and noisier Hi-C signal. Separating this cluster into sub-clusters representing each *S. cerevisiae* strain represents an additional challenge that will require further algorithmic development.

Next, the genomic content of individual yeast species was scaffolded from the clusters of contigs representing each species. The contigs in each cluster were run through the Lachesis software described in the Examples above (Burton et al. 2013) to create chromosome-scale scaffolds. With the *S. stipitis* contig cluster, this approach yielded a scaffold for each of the eight *S. stipitis* chromosomes, with a total scaffolded sequence length of 14.2 Mb (91.7% of the *S. stipitis* reference genome, and 95.1% of the portion of the *S. stipites* genome that appeared in the draft metagenome assembly) (FIG. 20C). These scaffolds matched the reference *S. stipitis* genome assembly fairly well (FIG. 27). There were a number of clustering errors, including one chromosomal cluster containing telomeric sequence from four other chromosomes, but the local misassembly rates were quite low: 0.9% and 1.1% for ordering and orientation errors, respectively. This same method was applied to the contig cluster representing *K. wickerhamii*, producing chromosome-scale scaffolds for each of the seven *K. wickerhamii* chromosomes, with a total length of 9.4 Mb (FIG. 20*d*). These scaffolds may represent a draft assembly with far higher contiguity than the existing *K. wickerhamii* reference genome (Baker, Tuch, and Johnson 2011), which has an N50 contig size of only 36.7 Kb. Thus, the MetaPhase approach can be combined with Lachesis to create high-contiguity de novo genome assemblies of individual eukaryotic species within metagenome samples.

Concurrently deconvoluting eukaryotic, bacterial, and archaeal genomes: Next, it was determined whether Meta-Phase could be applied to deconvolute a metagenome consisting of both eukaryotic and prokaryotic species. Towards a proof of concept, samples of eighteen species were gathered, including eight yeasts, nine bacteria, and one archaeon, thus representing all three domains of life ("M-3D"; Table 1, FIG. 28). The species were grown in appropriate rich media and mixed together in similar proportions. The proportions were estimated by a combination of spectrophotometric, flow sorting, and counting approaches and were later confirmed by sequence coverage (FIG. 47).

A simulated draft de novo metagenome assembly was created for M-3D by splitting the reference genomes of the 18 species into 10-Kb contigs. In addition, a Hi-C sequencing library was experimentally generated for the M-3D sample (Table 2), and these reads were aligned to the simulated contigs of the draft assembly, and the contigs were clustered using Hi-C link frequencies (FIG. 29A). This algorithm (described in the Examples above) predicted the presence of 18 distinct clusters, consistent with the actual content of the simulated draft assembly and experimental Hi-C data (FIG. S4). It clustered 89.1% of the simulated contigs into these 18 clusters; of the unclustered contigs, 85.8% contained no HindIII restriction sites and thus are not expected to produce a Hi-C signal in this experiment. The 18 clusters clearly matched the 18 species in the sample, with 99.6% of contigs clustered correctly (FIG. 29B, FIG. 30). The clusters corresponding to archaeal and bacterial species had a particularly high accuracy rate of 99.87%. Bootstrapping tests confirmed the robustness of the method (FIG. 48).

Thus, the approach described herein can simultaneously deconvolute the genomes of microbes belonging to all three domains of life, making it applicable to real and complex microbial communities.

Lastly, Hi-C was used to scaffold the genomic content of prokaryotic species from clustered contigs. Consistent with previous findings (Umbarger et al. 2011), it was observed in the M-3D sample that both bacterial and archaeal genomes contain a substantially weaker signal of genomic proximity in Hi-C data than do eukaryotic genomes (FIG. 31). This suggests that in prokaryotic species, in sharp contrast with eukaryotic species, Hi-C is not very useful for ordering or orienting genomic content within chromosomes. However, Lachesis' clustering algorithm can still be used to deconvolute chromosomes, including plasmids, inside prokaryotic cells. This algorithm was applied to the genome of *Vibrio fischeri* ES114, a bacterial strain present in M-3D that contains two chromosomes and one plasmid, pES100 (FIG. 29C). The chromosomal architecture of *V. fischeri* prevented a complete merging of its chromosome I, but chromosome II and pES100 both formed distinct clusters (FIG. 29*d*). Thus, MetaPhase and Lachesis are capable of using Hi-C signal not only to deconvolute prokaryotic genomes, but also to separate plasmid-derived sequence from chromosomal sequence within clusters corresponding to individual species.

Discussion

Here it was demonstrated that contact probability maps such as those generated by Hi-C may be used to deconvolute shotgun metagenome assemblies and the reconstruction of individual genomes from mixed cell populations. Using only a single Hi-C library taken from a metagenome sample, two different signals inherent to Hi-C read pairing were exploited in ways not previously contemplated: the intracellularity of each pair, which enables species-level deconvolution, and the correlation of Hi-C linkage with chromosomal distance, which enables scaffolding of the de novo assemblies of at least eukaryotic species, as described in the Examples above (Burton et al. 2013). All of the sequencing libraries used here were generated by in vitro methods and were sequenced on a single cost-effective sequencing platform.

The MetaPhase method is straightforward enough to be applicable to any metagenome sample from which a sufficient number of intact microbial cells can be isolated (105-108). Furthermore, this approach can be applied to microbial communities containing both prokaryotes and eukaryotes. The application of MetaPhase to diverse microbial communities may permit the discovery and genome assembly of many unculturable and currently unknown microbial species. Additionally, the use of the intra-cluster enrichment metric (FIG. 24) permits a rough estimate of the species diversity within a draft metagenome assembly, a useful piece of information that is not easily measured. However, as with all shotgun metagenomic sequencing, low-abundance species—such as *P. pastoris* in the M-Y sample—will remain challenging to assemble into contigs without very deep sequencing. Additionally, in samples containing species such as dinoflagellates with unusually large genomes (Moustafa et al. 2010), even deeper sequencing of both shotgun and Hi-C libraries may be necessary.

It is noted that as MetaPhase delineates genomic content corresponding to individual microbial species, it also informs the chromosome and plasmid structure of these genomes, and in the case of eukaryotic species it is capable of facilitating high contiguity draft genome assemblies. Thus it makes new species immediately amenable to phylogenetic and functional analysis while concomitantly increasing the power of existing genome databases to classify metagenomic reads via non-de novo methods. This method need not be limited to metagenome samples, as any complex cell mixture may be deconvoluted into individual genomes assuming enough genomic diversity is present that reads can be accurately mapped.

The computational portions of the MetaPhase method include software written in C++ using Boost (www.boost.org) with auxiliary scripts written in Perl and bash in accordance with certain embodiments. Such embodiments run in a Unix environment.

Example 4

Species-Level Deconvolution of Metagenome Samples Derived from Open Air Inoculated Craft Beer Fermentation The MetaPhase method described in Example 3 above may be applied to a sample derived from open-air inoculated craft beer fermentation. The sample was determined to have 8 species present (FIG. 32). Using BlastX, the species in the sample were identified as *Saccharomyces cerevisiae* (the canonical brewing yeast); *Dekkera bruxellensis* (a.k.a. Brett, common brewing yeast); *Pichia kudriavzevii* (a ubiquitous spoilage yeast); An unknown yeast species (distantly related to *Hansenula*); *Acetobacter pomorum* (spoilage bacterium, makes vinegar); a novel strain in *Acetobacter*, which was also isolated and sequenced; a novel species in *Lactobacillus*, another genus of spoilage bacteria, which was also isolated and sequenced; and an unknown bacterial species (distant relative to *Pediococcus*) (FIG. 33).

Most clusters contain 1 known species, and the accuracy of this method to mapping contigs to the correct species is >99.7% (FIG. 34). This method assembles known species to 65%-87% completion.

Example 5

Species-Level Deconvolution of Metagenome Samples Derived from a Clinical Sample The MetaPhase method described in Example 3 above may be applied to a sample derived from a clinical sample, specifically, a human vaginal microbiome with bacterial vaginosis infection (BV+). The sample was determined to have 25 species present (FIG. 35). The most well-defined clusters represent abundant species (FIG. 36). The species abundances shown match closely with a prior survey of this sample using 16S rRNA sequencing.

The correspondence between species and clusters is mostly not one-to-one due to many factors, including the presence of multiple closely related strains in the sample (e.g., of *Gardnerella vaginalis*); sequence differences between the strains in the sample and the reference strains; and especially the presence of novel species in the sample that are only distantly related to any species for which reference genomes exist. (FIG. 37).

REFERENCES

The references, patents and published patent applications listed below, and all references cited in the specification above are hereby incorporated by reference in their entirety, as if fully set forth herein.

Adey, A. et al. The haplotype-resolved genome and epigenome of the aneuploid HeLa cancer cell line. Nature 500, 207-211 (2013).

Albertsen M., Hugenholtz P., Skarshewski A., Nielsen K. L., Tyson G. W., et al., 2013. "Genome sequences of rare, uncultured bacteria obtained by differential coverage binning of multiple metagenomes." Nat. Biotech. 31 (6):533-538.

Altschul, S. F., Gish, W., Miller, W., Myers, E. W. & Lipman, D. J. Basic local alignment search tool. Journal of Molecular Biology 215, 403-10 (1990).

Baird, N. A. et al. Rapid SNP discovery and genetic mapping using sequenced RAD markers. PLoS One 3, e3376 (2008).

Baker C. R., Tuch B. B., Johnson A. D., 2011. "Extensive DNA-binding specificity divergence of a conserved transcription regulator." PNAS 108 (18):7493-7498.

Beitel C. W., Froenicke L., Lang J. M., Korf I. F., Michelmore R. W., et al., 2014. "Strain- and plasmid-level deconvolution of a synthetic metagenome by sequencing proximity ligation products". PeerJ PrePrints 2:e260v1.

Belloch C., Barrio E., Garcia M. D., Querol A., 1998. "Inter- and intraspecific chromosome pattern variation in the yeast genus *Kluyveromyces*." Yeast 14 (15):1341-1354.

Burton J. N., Adey A., Patwardhan R. P., Qiu R. L., Kitzman J. O., Shendure J., 2013. "Chromosome-scale scaffolding of de novo genome assemblies based on chromatin interactions." Nat. Biotech. 31 (12):1119-1125.

Carr R., Shen-Orr S. S., Borenstein E., 2013. "Reconstructing the Genomic Content of Microbiome Taxa through Shotgun Metagenomic Deconvolution." PLoS Comp. Biol. 9 (10).

Compeau, P., Pevzner, P. & Tesler, G. How to apply de Bruijn graphs to genome assembly. Nature Biotechnology 29, 987-91 (2011).

David L. A., Maurice C. F., Carmody R. N., Gootenberg D. B., Button J. E., et al., 2014. "Diet rapidly and reproducibly alters the human gut microbiome." Nature 505 (7484):559-563.

Dekker J., Marti-Renom M. A., Mirny L. A., 2013. "Exploring the three-dimensional organization of genomes: interpreting chromatin interaction data." Nat. Rev. Gen. 14 (6):390-403

Dick G. J., Andersson A. F., Baker B. J., Simmons S. L., Yelton A. P., et al., 2009. "Community-wide analysis of microbial genome sequence signatures." Genome Biol. 10 (8).

Dixon, J. et al. Topological domains in mammalian genomes identified by analysis of chromatin interactions. Nature 485, 376-80 (2012).

Dong, Y. et al. Sequencing and automated whole-genome optical mapping of the genome of a domestic goat (Capra-hircus). Nature Biotechnology 31, 135-41 (2013).

Duan, Z. et al. A three-dimensional model of the yeast genome. Nature 465, 363-7 (2010).

Eisen, M., Spellman, P., Brown, P. & Botstein, D. Cluster analysis and display of genome-wide expression patterns. Proceedings of the National Academy of Sciences of the United States of America 95, 14863-8 (1998).

Fraley, C & Raftery, A. E. How Many Clusters? Which Clustering Method? Answers Via Model-Based Cluster Analysis. The Computer Journal 41, 578-588 (1998).

Frias-Lopez J., Shi Y., Tyson G. W., Coleman M. L., Schuster S. C., et al., 2008. "Microbial community gene expression in ocean surface waters." PNAS 105 (10): 3805-3810.

Genome 10K Community of Scientists. Genome 10K: a proposal to obtain whole-genome sequence for 10,000 vertebrate species. The Journal of Heredity 100, 659-74 (2009).

Gnerre, S. et al. High-quality draft assemblies of mammalian genomes from massively parallel sequence data. Proceedings of the National Academy of Sciences of the United States of America 108, 1-6 (2011).

Gordon J. L., Byrne K. P., Wolfe K. H., 2011. "Mechanisms of Chromosome Number Evolution in Yeast." PLoS Genetics 7 (7).

Howe A. C., Jansson J. K., Malfatti S. A., Tringe S. G., Tiedje J. M., et al., 2014. "Tackling soil diversity with the assembly of large, complex metagenomes." PNAS 111 (13):4904-4909.

Hug L. A., Castelle C. J., Wrighton K. C., Thomas B. C., Sharon I, et al., 2013. "Community genomic analyses constrain the distribution of metabolic traits across the Chloroflexi phylum and indicate roles in sediment carbon cycling." Microbiome 1 (1):22.

Huttenhower C. D., Human Microbiome Project Consortium, et al., 2012. "Structure, function and diversity of the healthy human microbiome." Nature 486 (7402):207-214.

International Human Genome Sequencing Consortium. Finishing the euchromatic sequence of the human genome. Nature 431, 931-945 (2004).

International Human Genome Sequencing Consortium. Initial sequencing and analysis of the human genome. Nature 409, 1-62 (2001).

Iverson V., Morris R. M., Frazar C. D., Berthiaume C. T., Morales R. L., et al., 2012. "Untangling Genomes from Metagenomes: Revealing an Uncultured Class of Marine Euryarchaeota." Science 335 (6068):587-590.

Jarvis R. A., Patrick E. A., 1973. "Clustering Using a Similarity Measure Based on Shared near Neighbors." IEEE Transactions on Computers C-22 (11):1025-1034.

Jeffries T. W., Grigoriev I. V., Grimwood J., Laplaza J. M., Aerts A., et al., 2007. "Genome sequence of the lignocellulose-bioconverting and xylose-fermenting yeast *Pichia stipitis*." Nat. Biotech. 25 (3):319-326.

Jung, Y., Park, H., Du, D. Z. & Drake, B. A decision criterion for the optimal number of clusters in hierarchical clustering. Journal of Global Optimization 1-21 (2003).

Kaplan N., and Dekker J., 2013. "High-throughput genome scaffolding from in vivo DNA interaction frequency." Nat. Biotech. 31 (12):1143-1147.

Kitzman, J. O. et al. Haplotype-resolved genome sequencing of a Gujarati Indian individual. Nature Biotechnology 29, 1-6 (2011).

Lam, E. et al. Genome mapping on nanochannel arrays for structural variation analysis and sequence assembly. Nature Biotechnology 30, 771-6 (2012).

Landry, J. et al. The genomic and transcriptomic landscape of a HeLa cell line. Genes Genomes I Genetics 1-27 (2013).

Le T. B. K., Imakaev M. V., Mirny L. A., Laub M. T., 2013. "High-Resolution Mapping of the Spatial Organization of a Bacterial Chromosome." Science 342 (6159):731-734.

Li H., Durbin R., 2009. "Fast and accurate short read alignment with Burrows-Wheeler transform." Bioinformatics 25 (14):1754-1760.

Li, H. & Durbin, R. Fast and accurate long-read alignment with Burrows-Wheeler transform. Bioinformatics 26, 589-95 (2010).

Li, R. et al. De novo assembly of human genomes with massively parallel short read sequencing. Genome Research 20, 265-272 (2010).

Lieberman-Aiden, E. et al. Comprehensive mapping of long-range interactions reveals folding principles of the human genome. Science 326, 289-293 (2009).

Mackay, T. et al. The *Drosophila melanogaster* Genetic Reference Panel. Nature 482, 173-8 (2012).

Macville, M. et al. Comprehensive and definitive molecular cytogenetic characterization of HeLa cells by spectral karyotyping. Cancer Research 59, 1-11 (1999).

Mitra S., Forster-Fromme K., Damms-Machado A., Scheurenbrand T., Biskup S., et al., 2013. "Analysis of the intestinal microbiota using SOLiD 16S rRNA gene sequencing and SOLiD shotgun sequencing." BMC Genomics 14.

Moissiard, G. et al. MORC family ATPases required for heterochromatin condensation and gene silencing. Science 336, 1448-51 (2012).

Mouse Genome Sequencing Consortium. Initial sequencing and comparative analysis of the mouse genome. Nature 420, 1-43 (2002).

Moustafa A., Evans A. N., Kulis D. M., Hackett J. D., Erdner D. L., et al., 2010. "Transcriptome profiling of a toxic dinoflagellate reveals a gene-rich protist and a potential impact on gene expression due to bacterial presence." PLoS One 5 (3):e9688.

Namiki T., Hachiya T., Tanaka H., Sakakibara Y., 2012. "MetaVelvet: an extension of Velvet assembler to de novo metagenome assembly from short sequence reads." Nucleic Acids Res. 40 (20).

Narasingarao P., Podell S., Ugalde J. A., Brochier-Armanet C., Emerson J. B., et al., 2012. "De novo metagenomic assembly reveals abundant novel major lineage of Archaea in hypersaline microbial communities." ISME Journal 6 (1):81-93.

Peng Y., Leung H. C. M., Yiu S. M., Chin F. Y. L., 2012. "IDBA-UD: a de novo assembler for single-cell and metagenomic sequencing data with highly uneven depth." Bioinformatics 28 (11):1420-1428.

Qin J. J., MetaHIT Consortium, et al., 2010. "A human gut microbial gene catalogue established by metagenomic sequencing." Nature 464 (7285):59-U70.

Renouf V., Claisse O., Lonvaud-Funel A., 2007. "Inventory and monitoring of wine microbial consortia." Appl. Microbiol. and Biotech. 75 (1):149-164.

Rinke C., Schwientek P., Sczyrba A., Ivanova N. N., Anderson I. J., et al., 2013. "Insights into the phylogeny and coding potential of microbial dark matter." Nature 499 (7459):431-437.

Saeed I., Tang S. L., Halgamuge S. K., 2012. "Unsupervised discovery of microbial population structure within metagenomes using nucleotide base composition." Nucleic Acids Res. 40 (5): e34.

Schwartz, D. C. et al. Ordered restriction maps of *Saccharomyces cerevisiae* chromosomes constructed by optical mapping. Science 262, 110-4 (1993).

Sexton, T. et al. Three-dimensional folding and functional organization principles of the *Drosophila* genome. Cell 148, 458-72 (2012).

Sharon I., Morowitz M. J., Thomas B. C., Costello E. K., Relman D. A., et al., 2013. "Time series community genomics analysis reveals rapid shifts in bacterial species, strains, and phage during infant gut colonization." Genome Res. 23 (1):111-120.

Shendure, J. & Ji, H. Next-generation DNA sequencing. Nature Biotechnology 26, 1-11 (2008).

Shendure, J. & Lieberman-Aiden, E. The expanding scope of DNA sequencing. Nature Biotechnology 30, 1084-94 (2012).

Sievers F., Wilm A., Dineen D., Gibson T. J., Karplus K., et al., 2011. "Fast, scalable generation of highquality protein multiple sequence alignments using Clustal Omega". Mol. Syst. Biol. 7:539.

Simonis, M. et al. High-resolution identification of balanced and complex chromosomal rearrangements by 4C technology. Nature Methods 6, 837-42 (2009).

Umbarger M. A., Toro E., Wright M. A., Porreca G. J., Bau D., et al., 2011. "The Three-Dimensional Architecture of a Bacterial Genome and Its Alteration by Genetic Perturbation." Mol. Cell 44 (2):252-264.

van Berkum, N. L. et al. Hi-C: a method to study the three-dimensional architecture of genomes. Journal of Visualized Experiments 1-7 (2010).

Venter J. C., Remington K., Heidelberg J. F., Halpern A. L., Rusch D., et al., 2004. "Environmental genome shotgun sequencing of the Sargasso Sea." Science 304 (5667):66-74.

Wood D. E., Salzberg S. L., 2014. "Kraken: ultrafast metagenomic sequence classification using exact alignments." Genome Biol. 15 (3):R46.

Xin G., Glawe D., Doty S. L., 2009. "Characterization of three endophytic, indole-3-acetic acid-producing yeasts occurring in *Populus* trees." Mycological Res. 113:973-980.

Yaffe, E. & Tanay, A. Probabilistic modeling of Hi-C contact maps eliminates systematic biases to characterize global chromosomal architecture. Nature Genetics 43, 1059-65 (2011).

Zhang, G. et al. The oyster genome reveals stress adaptation and complexity of shell formation. Nature 490, 49-54 (2012a).

Zhang, Q. et al. The genome of *Prunus mume*. Nature Communications 3, 1318 (2012b).

What is claimed is:

1. A method for large scale scaffolding of a genome assembly from a set of reads comprising:
    generating a chromosome interaction dataset from the set of reads from a genome of interest lacking a reference genome, wherein the chromosome interaction dataset includes intrachromosomal and interchromosomal contact information for the reads that provides long-range information for scaffolding the genome assembly, and wherein chromosome interaction dataset is generated by a chromosome conformation analysis technique selected from Chromatin Conformation Capture (3C), Circularized Chromatin Conformation Capture (4C), Carbon Copy Chromosome Conformation Capture (5C), Chromatin Immunoprecipitation (ChIP), ChIP-Loop, Hi-C, combined 3C-ChIP-cloning (6C), or Capture-C;
    aligning the set of reads with a draft assembly sequence, a shotgun assembly sequence, or a reference assembly sequence, wherein the alignment results in a test set of contigs;
    generating a de novo genome assembly to establish long range or chromosome-scale contiguity of the genome of interest from the draft assembly sequence, the shotgun assembly sequence, or the reference assembly sequence by subjecting the chromosome interaction dataset and the test set of contigs to a scaffolding method performed by a computing system, the scaffolding method comprising:
        clustering the test set of contigs to form two or more location cluster groups by performing a hierarchical agglomerative clustering algorithm on a clustering graph to generate an agglomerated clustering graph, each location cluster group comprising one or more location-clustered contigs;
        ordering the one or more location-clustered contigs within each of the two or more location cluster groups to form an ordered set of one or more location-clustered contigs within each cluster group by determining a minimum spanning tree of the agglomerated clustering graph and finding the longest path in the minimum spanning tree for each location cluster group;
        orienting each ordered set of one or more location-clustered contigs to assign a relative orientation to each of the location-clustered contigs within each location cluster group by performing an orienting algorithm on a weighted directed acyclic graph (WDAG).

2. The method of claim 1, wherein the two or more location cluster groups are two or more chromosome groups, each chromosome group comprising one or more contigs derived from the same chromosome.

3. The method of claim 1, wherein the test set of contigs comprises at least 10 contigs.

4. The method of claim 1, wherein test set of contigs comprises at least 46 contigs and the scaffolding method performed by a computing system comprises clustering the test set of contigs to form 23 location cluster groups.

* * * * *